US007255993B1

(12) United States Patent
Young et al.

(10) Patent No.: US 7,255,993 B1
(45) Date of Patent: Aug. 14, 2007

(54) DETECTION OF MUTATIONAL FREQUENCY AND RELATED METHODS

(75) Inventors: Neal S. Young, Washington, DC (US); Sachiko Kajigaya, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 27 days.

(21) Appl. No.: 10/704,283

(22) Filed: Nov. 6, 2003

Related U.S. Application Data

(60) Provisional application No. 60/463,077, filed on Apr. 14, 2003, provisional application No. 60/424,515, filed on Nov. 6, 2002.

(51) Int. Cl.
*C12Q 1/68* (2006.01)
*C12P 19/34* (2006.01)
*C07H 21/04* (2006.01)

(52) U.S. Cl. ....................... 435/6; 435/91.2; 536/24.33

(58) Field of Classification Search ............... 536/23.1, 536/24.33; 425/6, 91.2
See application file for complete search history.

(56) References Cited

U.S. PATENT DOCUMENTS

| | | | | |
|---|---|---|---|---|
| 5,948,624 | A * | 9/1999 | Rothschild et al. | 435/6 |
| 5,976,798 | A | 11/1999 | Parker | |
| 6,322,974 | B1 | 11/2001 | Runge | |
| 6,344,322 | B1 | 2/2002 | Polyak | |
| 6,462,190 | B1 | 10/2002 | Michikawa | |

OTHER PUBLICATIONS

Gattwemann et al. Heteroplasmic point mutations of mitochondrial DNA affecting subunit I of cytocrome c oxidase in two patients with aquired idiopathic sideroblastic anemia. Blood, vol. 90, No. 12, pp. 4961-4972, 1997.*

Chinnery and Turnbull, "Mitochondrial DNA mutations in the pathogenesis of human disease," *Mol. Med. Today* 6(11):425-432, 2000.

Coller et al., "Frequent intracellular clonal expansions of somatic mtDNA mutations," *Ann. N.Y. Acad. Sci.* 959:434-447, 2002.

Coller et al., "High frequency of homoplasmic mitochondrial DNA mutations in human tumors can be explained without selection," *Nature Genetics* 28:147-150, 2001.

Elson et al., "Random intracellular drift explains the clonal expansion of mitochondrial DNA mutations with age," *Am. J. Hum. Genet.* 68(3):802-6, 2001, Epub 2001.

Gattermann et al., "Heteroplasmic point mutations of mitochondrial DNA affecting subunit I of cytochrome c oxidase in two patients with acquired idiopathic sideroblastic anemia," *Blood* 90(12):4961-4972, 1997.

Gerhard et al., "Mitochondrial DNA mutation analysis in human skin fibroblasts from fetal, young, and old donors," *Mech. Ageing Dev.* 123(2-3):155-166, 2002.

Golden and Melov, "Mitochondrial DNA mutations, oxidative stress, and aging," *Mech. Ageing Dev.* 122(14):1577-1589, 2001.

Gyllensten et al., "Paternal inheritance of mitochondrial DNA in mice," *Nature* 352(6332):255-257, 1991.

He et al., "Detection and quantification of mitochondrial DNA deletions in individual cells by real-time PCR," *Nucleic Acids Res.* 30(14):e68, 2002.

Howell and Smejkal, "Persistent heteroplasmy of a mutation in the human mtDNA control region: hypermutation as an apparent consequence of simple-repeat expansion/contraction," *Am. J. Hum. Genet.* 66(5):1589-1598, 2000, Epub 2000.

Jenuth et al., "Tissue-specific selection for different mtDNa genotypes in heteroplasmic mice," *Nat. Genet.* 16(1):93-5, 1997.

Jones et al., "Detection of mitochondrial DNA mutations in pancreatic cancer offers a "mass"-ive advantage over detection of nuclear DNA mutations," *Cancer Res.* 61(4):1299-1304, 2001.

Khrapko et al., "Cell-by-cell scanning of whole mitochondrial genomes in aged human heart reveals a significant fraction of myocytes with clonally expanded deletions," *Nucleic Acids Res.* 27(11):2434-2441, 1999.

Malik et al., "Evidence for the de novo regeneration of the pattern of the length heteroplasmy associated with the T16189C variant in the control (D-loop) region of mitochondrial DNA," *J. Hum. Genet.* 47(3):122-130, 2002.

Naviaux, "Mitochondrial DNA disorders," *Eur. J. Pediatr.* 159 Suppl. 3:S219-226, 2000.

Nekhaeva, et al., "Clonally expanded mtDNA point mutations are abundant in individual cells of human tissues," *Proc. Natl. Acad. Sci. U.S.A.* 99(8):5521-6, 2002, Epub 2002.

Penta et al., "Mitochondrial DNA in human malignancy," *Mutat. Res.* 488(2):119-133, 2001.

Reddy et al., "Increased incidence of mitochondrial cytochrome c-oxidase gene mutations in patients with myelodysplastic syndromes," *British Journal of Haematology* 116(3):564-575, 2002.

(Continued)

*Primary Examiner*—Suryaprabha Chunduru
(74) *Attorney, Agent, or Firm*—Klarquist Sparkman, LLP

(57) ABSTRACT

Methods are provided herein for measuring the mutational frequency of a DNA molecule in cells, for example stem cells or hematopoietic cells such as $CD34^+$ cells or granulocytes. The method includes sequencing corresponding regions of mtDNA from a set of hematopoietic cells, or a set of clonal populations of hematopoietic cells, and comparing the sequence of the corresponding regions of mtDNA from the cells, or clonal populations of cells. The method also includes the comparison of mtDNA sequences with genomic DNA sequences. Also provided are methods for screening for an agent that has a mutagenic effect on a cell. The method includes contacting, or treating, clonal populations of cells with an agent and comparing the sequence of the mtDNA obtained from the treated clonal populations of cells, with the sequence of the corresponding region of mtDNA obtained from a control clonal populations of cells.

32 Claims, 3 Drawing Sheets

OTHER PUBLICATIONS

Shin et al., "Marked mitochondrial DNA sequence heterogeneity in single CD34+ cell clones from normal adult bone marrow," *Blood* 103(2):553-561, 2004, Epub 2003.

Shin et al., "Mitochondrial DNA mutations in patients with myelodysplastic syndromes," *Blood* 101(8):3118-3125, 2003, Epub 2002.

Shin et al., "Unexpected mitochondrial DNA heterogeneity in single CD34+ cell clones from normal bone marrow," 44th American Society for Hematology Annual Meeting, Nov. 6, 2002.

Shoubridge et al., "Deletion mutants are functionally dominant over wild-type mitochondrial genomes in skeletal muscle fiber segments in mitochondrial disease," *Cell* 62(1):43-49, 1990.

Stoneking, "Hypervariable sites in the mtDNA control region are mutational hotspots," *Am. J. Hum. Genet.* 67:1029-1032, 2000.

Zhang et al., "Strikingly higher frequency in centenarians and twins of mtDNA mutation causing redmodeling of replication origin in leukocytes," *Proc. Natl. Acad. Sci. U.S.A.* 100(3):1116-21, 2003, Epub 2003.

http://www.mitotypingcom/dna.htm, "About mitochondrial DNA," Nov. 6, 2002.

* cited by examiner

DETECTION OF MUTATIONAL FREQUENCY AND RELATED METHODS

PRIORITY CLAIM

This application claims the benefit of U.S. Provisional Application No. 60/424,515, filed Nov. 6, 2002, and U.S. Provisional Application No. 60/463,077, filed Apr. 14, 2003, both of which are incorporated herein by reference.

FIELD OF THE DISCLOSURE

This disclosure relates to the field of detection of genetic mutations, more specifically to the mutational frequency of genomic and mitochondrial DNA (mt DNA) in hematopoietic cells, such as hematopoietic stem cells.

BACKGROUND OF THE DISCLOSURE

The human mitochondrial genome is an approximately 16 kilobase circular, double stranded DNA that encodes 13 polypeptides of the mitochondrial respiratory chain, 22 transfer RNAs, and two ribosomal RNAs required for protein synthesis. Multiple copies of mtDNA exist in a single cell.

The mitochondrial genome is particularly susceptible to mutations. It is believed that the elevated mtDNA mutation rate is a result of the high level of reactive oxygen species generated in the organelle, coupled with a low level of DNA repair. Mutations in the mtDNA sequence that affect all copies of mtDNA in an individual are known as homoplasmic. Mutations that affect only some copies of mtDNA are known as heteroplasmic, thus cells can contain a mixture of both mutant and wildtype mtDNA species. Since multiple copies of mtDNA exist in a single cell, a mtDNA mutation may only become physiologically relevant once the particular mtDNA mutation accumulates in the cell and exceeds a certain threshold.

Somatic cell mtDNA mutations have been intensely studied because of their proposed involvement in the development of diseases. For example, large heteroplasmic deletions of mtDNA have been identified in muscle biopsies from patients suffering from a relatively common mitochondrial myopathy. Missense and silent mutations in the genes encoding cytochrome c oxidase subunits have been shown to segregate with Alzheimer's disease and it has been demonstrated that a high proportion of human tumors contain one or more mtDNA mutations. It is known that the Pearson marrow-pancreas syndrome involves hematopoietic, as well as pancreatic, abnormalities arising from a defect of oxidative phosphorylation which is associated with deletions in the mtDNA. Finally, it is believed that the number of somatic mtDNA mutations in humans increases with the age of the individual and thus mtDNA mutations may be involved in the aging process.

Currently, there is no adequate method that allows the measurement of the mutational frequency in the mitochondrial or genomic (nuclear) DNA of intact animals, including humans. Thus, there remains a need in the art to develop methods for measuring and monitoring the mutational frequency of DNA in cells.

SUMMARY OF THE DISCLOSURE

It is now surprisingly revealed that mtDNA mutations can be used to measure the mutational frequency of a mitochondrial DNA sequence. For instance, the frequency can be determined by measuring the number (or percent or proportion) of cells, or clonal populations of cells, with at least one mutation in a corresponding region of mtDNA within a set of test cells, or within a set of clonal populations of test cells. The mtDNA mutations can also be used to estimate (by correlation) the mutational frequency of a genomic (nuclear) DNA sequence. It is also surprisingly revealed that the measurement of a mtDNA mutational frequency can be used to screen for agents that increase the mutational frequency of a cell, such as a hematopoietic cell. In addition, the measurement of mtDNA mutational frequency can be used to track mtDNA and genomic DNA mutagenesis, for instance mutagenesis caused by disease, therapeutic treatments, environmental exposure, and other influences, using hematopoietic cells, such as $CD34^+$ cells, granulocytes, monocytes, or macrophages.

A first embodiment is a method of measuring the mutational frequency of a mtDNA sequence, which method involves isolating a set (for example two or more) of test cells (such as hematopoietic cells), for example test cells from a subject; sequencing a region of the mtDNA; and determining the proportion of test cells exhibiting mtDNA heterogeneity within the sequenced region of the mtDNA, thereby measuring the mutational frequency of the mtDNA sequence in the subject.

In specific examples of this method, the cells are hematopoietic cells, for example isolated $CD34^+$ cells, granulocytes, monocytes, or macrophages. In particular examples, the cells are hematopoietic stem cells, such as $CD34^+$ cells. The hematopoietic cell is in some embodiments isolated from a bone marrow aspirate, from umbilical cord blood, or from peripheral blood.

In other examples, the cells are non-tumor cells, such as skin cells or intestinal epithelial cells, particularly relatively undifferentiated skin cells or intestinal epithelial cells.

In more specific embodiments, the cells are each expanded into a separate clonal population of cells. In such an embodiment, mtDNA is extracted from each of the clonal populations, a corresponding region of the mtDNA of each population is sequenced, and the proportion of clonal populations (or colonies) exhibiting mtDNA heterogeneity within the sequenced region is determined. Other specific, non-limiting examples of the method further involve amplification of the mtDNA prior to determining the proportion of cells possessing at least one mtDNA mutation that distinguishes it from cells with a mtDNA sequence containing only polymorphisms.

In any of the provided methods, the subject from whom the cells (for example the hematopoietic cells) are isolated can be a subject who has a disease, or who is suspected of having a disease in which mtDNA mutations are present or more prevalent. In other embodiments, the subject has been subjected to a mutagenic treatment, for instance a treatment that involves chemotherapy or radiation, such that mutagenic damage from the treatment may be assessed. Alternatively, the subject in some examples is exposed to a man-made or a natural mutagenic agent, for instance an agent found in the environment. Alternatively, a relative increase in mtDNA mutations is used as an indicator that a subject has been exposed to a suspected or known mutagenic agent, or than an environment is contaminated with mutagens. In still other embodiments, the subject has (or is suspected of having) a genetic defect, for instance a defect in a component of a DNA repair mechanism or DNA replication mechanism. Optionally, the subject has (or is suspected of having) a genetic disease, such as Fanconi anemia, Bloom's syndrome, or certain types of tumors of the colon. Hence the method can be used as a diagnostic test to screen for or supplement other diagnostic tests in the evaluation of a disease in which mtDNA mutations have an increased prevalence.

Another embodiment is a method of estimating the mutational frequency of a genomic DNA sequence, which method involves isolating the cells (such as hematopoietic cells) from a subject; sequencing a corresponding region of the mtDNA in multiple of the isolated cells; determining the proportion of the cells exhibiting mtDNA heterogeneity within the sequenced region; and correlating the mutational frequency of the mtDNA to an estimated mutational frequency of genomic DNA from the same subject, thereby estimating the mutational frequency of the genomic DNA sequence. Optionally, the cells are expanded into multiple clonal populations of cells. In such an embodiment, mtDNA is extracted from each of the clonal populations, a corresponding region of the mtDNA of each population is sequenced, and the proportion of clonal populations (or colonies) possessing at least one mtDNA mutation within the sequenced region that distinguishes it from clonal populations with a mtDNA sequence containing only polymorphisms is determined. Other specific, non-limiting examples of the method further involve amplification of the mtDNA prior to determining the proportion of cells possessing at least one mtDNA mutation.

Yet another specific embodiment is a method of screening for an agent that has a mutagenic effect on a cell. Examples of such methods include contacting, or treating, the isolated cells with an agent. A region of the mtDNA, for example the mtDNA control region or another region in which mitochondrial mutations are known to frequently occur, is sequenced. In a further embodiment, the mtDNA is amplified prior to sequencing. The sequence of the mtDNA from the treated cells (such as hematopoietic cells) is compared to the sequence of a corresponding region of a control mtDNA from cells that were not contacted with the agent, thereby determining a proportion of treated cells exhibiting mtDNA heterogeneity in the sequenced region of the mitochondrial DNA and comparing it to a proportion of cells that were not contacted with the agent exhibiting mtDNA heterogeneity in the sequenced corresponding region in the control mitochondrial DNA. An increase in the proportion of treated cells exhibiting mtDNA heterogeneity, compared to the proportion of cells that were not contacted with the agent, indicates that the agent increases the mutational frequency of the cell. In one embodiment, isolated hematopoietic cells are expanded into multiple clonal populations of hematopoietic cells. In such an embodiment, the mtDNA is extracted from the clonal populations of hematopoietic cells.

The foregoing and other features and advantages will become more apparent from the following detailed description of several embodiments, which proceeds with reference to the accompanying figures.

BRIEF DESCRIPTION OF THE DRAWINGS

FIG. 3A is a flow chart showing the steps involved in the isolation and analysis of $CD34^+$ cells and mononuclear cells from peripheral blood. FIG. 3B is a schematic drawing of a mtDNA, including the control region, the CO1 and Cytb genes, as well as a linearized map and function location of the mtDNA control region between nucleotide 16,024 and nucleotide 16569 and between nucleotide 1 and nucleotide 576 (D-loop). FIG. 3C is a series of digital images showing the number and morphology of circulating $CD34^+$ clones after 5 day-suspension culture. Each image shows a different grade: image 1, less than 5 cells per well (grade 1); image 2, between 6 and 10 cells per well (grade 2); image 3, 11 to 20 cells per well (grade 3); image 4, more than 21 cells per well (grade 4).

SEQUENCE LISTING

Figure 1:
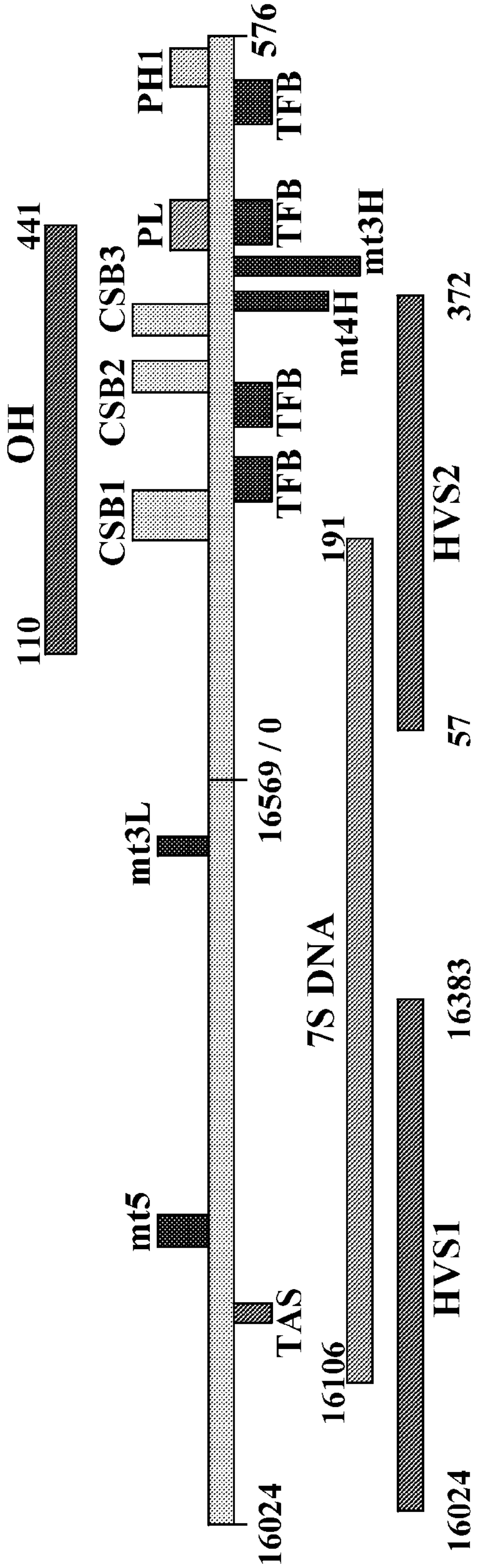
FIG. 1 is a schematic drawing of a linearized map, including the location of certain functional domains, of a human mtDNA control region.

The nucleic and amino acid sequences listed in the accompanying sequence listing are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NO: 1 is an upstream PCR primer of an outer nested primer pair for a control region of human mtDNA.

SEQ ID NO: 2 is a downstream PCR primer of an outer nested primer pair for a control region of human mtDNA.

SEQ ID NO: 3 is an upstream PCR primer of an inner nested primer pair for a control region of human mtDNA.

SEQ ID NO: 4 is a downstream PCR primer of an inner nested primer pair for a control region of human mtDNA.

SEQ ID NO: 5 is an upstream sequencing primer for the control region of human mtDNA.

SEQ ID NO: 6 is a downstream sequencing primer for the control region of human mtDNA.

SEQ ID NO: 7 is an upstream sequencing primer for the control region of human mtDNA.

SEQ ID NO: 8 is a downstream sequencing primer for the control region of human mtDNA.

SEQ ID NO: 9 is an upstream sequencing primer for the control region of human mtDNA.

SEQ ID NO: 10 is a downstream sequencing primer for the control region of human mtDNA.

SEQ ID NO: 11 is an upstream PCR primer of an outer nested primer pair for the Cytb gene of human mtDNA.

SEQ ID NO: 12 is a downstream PCR primer of an outer nested primer pair for the Cytb gene of human mtDNA.

SEQ ID NO: 13 is an upstream PCR primer of an inner nested primer pair for the Cytb gene of human mtDNA.

SEQ ID NO: 14 is a downstream PCR primer of an inner nested primer pair for the Cytb gene of human mtDNA.

SEQ ID NO: 15 is an upstream PCR primer of an outer nested primer pair for the CO1 gene of human mtDNA.

SEQ ID NO: 16 is a downstream PCR primer of an outer nested primer pair for the CO1 gene of human mtDNA.

SEQ ID NO: 17 is an upstream PCR primer of an inner nested primer pair for the CO1 gene of human mtDNA.

SEQ ID NO: 18 is a downstream PCR primer of an inner nested primer pair for the CO1 gene of human mtDNA.

SEQ ID NO: 19 is a downstream sequencing primer for the control region of human mtDNA.

SEQ ID NO: 20 is an upstream sequencing primer for the Cytb gene of human mtDNA.

SEQ ID NO: 21 is a downstream sequencing primer for the Cytb gene of human mtDNA.

SEQ ID NO: 22 is an upstream sequencing primer for the CO1 gene of human mtDNA.

SEQ ID NO: 23 is a downstream sequencing primer for the CO1 gene of human mtDNA.

DETAILED DESCRIPTION

I. Abbreviations

| | |
|---|---|
| AA | amino acid |
| Ala | Alanine |
| BM | bone marrow |
| CB | cord blood |
| CH | constant heavy |
| CL | constant light |
| CO1 | cytochrome c oxidase 1 |
| CSB | conserved sequence block |
| C tract | cytosine tract |
| Cytb | cytochrome b |
| F | forward primer |
| FACS | fluorescence activated cell sorting |
| G | grade |
| G-CSF | granulocyte-colony stimulating factor |
| HVS | hypervariable segment |
| I | inner primer |
| Ile | isoleucine |
| Leu | leucine |
| M | mutation |
| mtDNA | mitochondrial DNA |
| NC | nucleotide change |
| np | nucleotide position |
| O | outer primer |
| OH | H-strand origin |
| P | polymorphism |
| PB | peripheral blood |
| PBS | phosphate buffered saline |
| PCR | polymerase chain reaction |
| PE | phycoerythrin |
| PEf | plating efficiency |
| PH1 | major H-strand promoter |
| PL | L-strand promoter |
| R | reverse primer |
| SCF | stem cell factor |
| TAS | termination-associated sequence |
| TFB | transcription factor binding site |
| Thr | threonine |
| TPO | thrombopoeitin |
| TS | transition |
| TV | transversion |
| Val | valine |
| VH | variable heavy |
| VL | variable light |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Agent: Any substance, including, but not limited to, a chemical compound, small molecule, peptide mimetic, peptide or protein. An agent can be a mutagen and thus will have a mutagenic effect on a cell by causing mutations in the mtDNA or the genomic DNA of the cell.

Amplification: An increase in the amount of (number of copies of) nucleic acid sequence, wherein the increased sequence is the same as or complementary to the existing nucleic acid template. An example of amplification is the polymerase chain reaction (PCR), in which a biological sample collected from a subject is contacted with a pair of oligonucleotide primers, under conditions that allow for the hybridization (annealing) of the primers to nucleic acid template in the sample. The primers are extended under suitable conditions (though nucleic acid polymerization). If additional copies of the nucleic acid are desired, the first copy is dissociated from the template, and additional copies of the primers (usually contained in the same reaction mixture) are annealed to the template, extended, and dissociated repeatedly to amplify the desired number of copies of the nucleic acid.

The products of amplification may be characterized by electrophoresis, restriction endonuclease cleavage patterns, hybridization, ligation, and/or nucleic acid sequencing, using standard techniques.

Other examples of in vitro amplification techniques include reverse-transcription PCR (RT-PCR), strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Animal: Living multicellular organisms, a category which includes, for example, mammals and birds.

Antibody: Immunoglobulin (Ig) molecules and immunologically active portions of Ig molecules, for instance, molecules that contain an antigen binding site which specifically binds (immunoreacts with) an antigen. In one embodiment the antigen is CD34. Monoclonal and polyclonal immunoglobulins are encompassed by the disclosure.

A naturally occurring antibody (for example, IgG) includes four polypeptide chains, two heavy chains and two light chains inter-connected by disulfide bonds. However, it has been shown that the antigen-binding function of an antibody can be performed by fragments of a naturally occurring antibody. Thus, these antigen-binding fragments are also intended to be designated by the term "antibody". Examples of binding fragments encompassed within the term antibody include (i) an Fab fragment consisting of the variable light (VL), variable heavy (VH), constant light (CL) and constant heavy (CH)1 domains; (ii) an Fd fragment consisting of the VH and CH1 domains; (iii) an Fv fragment consisting of the VL and VH domains of a single arm of an antibody, (iv) a dAb fragment (Ward et al., (1989) *Nature* 341:544–546) which consists of a VH domain; and (v) an $F(ab')_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) *Science* 242:423–426; and Huston et al. (1988) *Proc. Natl. Acad. Sci.* 85:5879–5883) by recombinant methods. Such single chain antibodies, as well as dsFv, a disulfide stabilized Fv (Bera et al. (1998) *J. Mol. Biol.* 281:475–483), and dimeric Fvs (diabodies), that are generated by pairing different polypeptide chains (Holliger et al. (1993) *Proc. Natl. Acad. Sci.* 90:6444-6448), are also included.

In one embodiment, antibody fragments for use in this disclosure are those which are capable of cross-linking their target antigen, for example, bivalent fragments such as $F(ab')_2$ fragments. Alternatively, an antibody fragment which does not itself cross-link its target antigen (for example, a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

"Specifically binds" refers to the ability of individual antibodies to specifically immunoreact with an antigen. This binding is a non-random binding reaction between an antibody molecule and the antigen. In one embodiment, the antigen is CD34. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody".

A variety of methods for attaching detectable labels to antibodies are well known in the art. Detectable labels useful for such purposes are also well known in the art, and include radioactive isotopes such as $^{32}P$, fluorophores, chemiluminescent agents, and enzymes.

Antigen: Any molecule that can bind specifically with an antibody. An antigen is also a substance that antagonizes or stimulates the immune system to produce antibodies. Antigens are often foreign substances such as allergens, bacteria or viruses that invade the body.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding may be detected functionally by determining whether binding has an observable effect upon a biosynthetic process such as expression of a coding sequence, DNA replication, transcription, amplification and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) (under defined ionic strength and pH) at which 50% of the target sequence remains hybridized to a perfectly matched probe or complementary strand. A higher ($T_m$) means a stronger or more stable complex relative to a complex with a lower ($T_m$).

Bloom's syndrome: An autosomal recessive genetic disease caused by mutation of the BLM gene (GenBank Accession No. NM_000057). Patients with this disease show a range of symptoms which include a small body size, sun-sensitive facial reddening, sub- or infertility, immunodeficiency and a predisposition to the full range of human cancers. Cells from patients with Bloom's syndrome are genomically unstable and show elevated levels of both homologous recombination and sister chromatid exchange. Cells that are defective for BLM also show DNA replication defects. The BLM gene encodes a protein that displays 3' to 5' DNA helicase activity and promotes branch migration of Holliday junctions.

CD34: A cell surface antigen formerly known as hematopoietic progenitor cell antigen 1, and MY10, is a known marker of human hematopoietic stem cells. The human CD34 gene, which maps to chromosome 1q32, spans 26 kb and has 8 exons. CD34 is a 67 kDa transmembrane glycoprotein. CD34 is expressed selectively on human hematopoietic progenitor cells. The biological function of CD34 is still unknown.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples.

Clonal population of cells: A group of genetically identical cells all descended from a single cell. A clone of cells. For example, such a clonal population may include five or fewer cells, at least 2 cells, at least 5 cells, at least 10 cells, at least 20 cells, at least 100 cells, at least 200 cells, at least 500 cells, at least 1000 cells or at least 10,000 cells. In particular examples, the clonal population includes at least a sufficient number of cells to be informative about the presence of the mtDNA mutation.

Corresponding regions of mtDNA: A region located between the same two nucleotide positions in more than one mtDNA sequence. For example, the corresponding region of HVS 2 located between nucleotide position 57 and nucleotide position 372 in a first mtDNA sequence is the HVS 2 located between nucleotide position 57 and nucleotide position 372 in a second mtDNA sequence.

Fanconi anemia (FA): An inherited anemia that leads to bone marrow failure (aplastic anemia). It is a recessive disorder, thus if both parents carry a mutation in the same FA gene, each of their children has a 25% chance of inheriting both defective genes and acquiring the disease.

There are at least seven FA genes: A (GenBank Accession No. NM_000135), C (GenBank Accession No. NM_000136), D2 (GenBank Accession No. NM_033084), E (GenBank Accession No. NM_021922), F (GenBank Accession No. NM_022725), G (GenBank Accession No. NM_004629) and BRAC2 (GenBank Accession No.). Six of these genes have been cloned. These six account for more than 85% of the cases of FA. Specifically, mutations in FA-A and FA-C account for FA in 76% of patients worldwide.

FA occurs equally in males and females and is found in all ethnic groups. Although it is considered primarily a blood disease, it may affect all systems of the body. Many patients eventually develop acute myelogenous leukemia. Older patients are extremely likely to develop head and neck, esophogeal, gastrointestinal, vulvar, or rectal tumors.

Fluorphores: Chemical compounds, which when excited by exposure to a particular wavelength of light, emit light (for instance, fluoresce), for example at a different wavelength than that to which they were exposed.

Also encompassed by the term "fluorophore" are luminescent molecules, which are chemical compounds which do not require exposure to a particular wavelength of light to fluoresce; luminescent compounds naturally fluoresce. Therefore, the use of luminescent signals eliminates the need for an external source of electromagnetic radiation, such as a laser. An example of a luminescent molecule includes, but is not limited to, aequorin (Tsien, *Ann. Rev. Biochem.* 67:509, 1998).

Hematopoiesis: The formation and development of blood cells. Hematopoiesis involves the proliferation and differentiation of hematopoietic cells from stem cells. In adult mammals, hematopoiesis is known to occur in bone marrow. Mammalian hematopoietic cells are an extraordinarily diverse collection of cell types, including B cells, T cells, granulocytes, macrophages, megakaryocytes and erythroid cells, and each cell type has a unique morphology and function. Despite the diversity of the nature, morphology, characteristics and function of hematopoietic cells, it is believed that there exists a single progenitor, known as a pluripotent hematopoietic stem cell, which is capable of self-renewal as well as the generation of committed progenitors that give rise to mature hematopoietic cells.

A human hematopoietic stem cell has been identified that is a $CD34^+$ cell, in that it expresses CD34 on its surface. The $CD34^+$ cell population constitutes only a small percentage of the total number of hematopoietic cells in adult human bone marrow, however $CD34^+$ cells are more abundant in umbilical cord blood.

Hematopoietic cell: A blood cell, for example a cell involved in or produced by hematopoiesis. Hematopoietic cells can be, for example, red blood cells (erythrocytes) or white blood cells (leukocytes). Cells useful in the disclosed methods are blood cells that carry mtDNA, for example hematopoietic stem cells and leukocytes (such as granulocytes). There are five main types of white blood cell, subdivided between two main groups: polymorphonuclear leukocytes, or granulocytes, (neutrophils, eosinophils, basophils) and mononuclear leukocytes (monocytes and lymphocytes). There are two main classes of lymphocytes: B cells and T cells. A third class of lymphocytes includes Natural Killer (NK) cells. Cytotoxic T lymphocytes (CTL), helper T cells, and NKT cells are types of T cells. Also included among hematopoietic cells are megakaryocytes, which produce platelets (a particle found in the bloodstream that binds to fibrinogen at the site of a wound to begin the blood clotting process), and macrophages, which arise from monocytes and have phagocytic activity.

Mammalian blood cells provide for an extraordinarily diverse range of activities. The blood cells are divided into several lineages, including lymphoid, myeloid and erythroid. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers. Despite the diversity of the nature, morphology, characteristics and function of the blood cells, there appears to be a single progenitor, which is capable of self regeneration and by exposure to growth factors becomes dedicated to a specific lineage.

Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Indeed, one injected cell should be able to reconstitute all of the hematopoietic lineages. A human stem cell has also been identified that is a $CD34^+Thy1^+lin^-$ cell. This stem cell population constitutes only a small percentage of the total number of leukocytes in bone marrow. In particular, B cells ($CD19^+$) and myeloid cells ($CD33^+$) make up 80–90% of the $CD34^+$ population. Moreover, a combination of CD3, 8, 10, 15, 19, 20, and 33 will mark >90% of all $CD34^+$ cells.

Hereditary colon cancer: Genetic disease that often features colonic polyps or growths that eventually become cancerous. There are several kinds of colon cancer, including familial adenomatous polyposis (FAP) and a variant called Gardner's syndrome. Another type of colon cancer, hereditary non-polyposis colon cancer (HNPCC), features few, if any, polyps.

Genes found to be involved in colorectal cancer include MSH2 (GenBank Accession No. NM_000251), MSH6 (GenBank Accession No. NM_000179) (both on chromosome 2) and MLH1 (GenBank Accession No. NM_000249) (on chromosome 3). Normally, the protein products of these genes help to repair errors in DNA replication, however mutations in these genes can prevent DNA repair, eventually leading to colon cancer.

Heteroplasmy: Mutations that affect only some copies of mtDNA. Thus, cells that are heteroplasmic can contain a mixture of both mutant and wildtype mtDNA species. A tissue that is heteroplasmic can contain a mixture of both mutant and wildtype mtDNA species in one or more cells of the tissue.

Homoplasmy: Mutations in the mtDNA sequence that affect all copies of mtDNA in a cell (a cell is homoplasmic) or in a tissue (a tissue is homoplasmic).

Isolated: An "isolated" biological component (such as a nucleic acid molecule, protein or portion of a tissue) that has been substantially separated or purified away from other biological components in the cell of the organism in which the component naturally occurs. An "isolated" cell is a cell that has been purified from the other cellular components of a tissue. An "isolated" population of cells is a population of cells that has been purified from other populations of cells in a tissue. For example, a population of hematopoietic cells is a population of cells that has been substantially purified from other cell types and/or cellular components in a tissue. Cells can be isolated by, for instance mechanical and/or enzymatic methods.

In one embodiment, an isolated population of cells includes greater than about 95%, or greater than about 99%, of the cells of interest. In another embodiment, an isolated population of cells is one in which no other cells of a different phenotype or genotype can be detected. In a further embodiment, an isolated population of cell's is a population of cells that includes less than about 5%, or less than about 1% of a cells of a different phenotype than the cells of interest.

Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Labeled: A biomolecule, such as a specific binding agent, attached covalently or noncovalently to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, CSHL, New York, 1989 and Ausubel et al., *Current Protocols in Molecular Biology*, Greene Publ. Assoc. and Wiley-Intersciences, 1998.

Lineage specific marker: A marker that is expressed by a specific population of cells. In one embodiment, the cells are hematopoietic cells expressing the cell surface marker CD34. In other embodiments, the cells are hematopoietic cells expressing, but not limited to, the CD13, CD14, CD15, CD33, or CD66 cell surface markers. Cocktails of antibodies that bind lineage specific markers have been produced.

Leukocyte: Cells in the blood, also termed "white cells," that are involved in defending the body against infective organisms and foreign substances. Leukocytes are produced in the bone marrow. There are five main types of white blood cell, subdivided between two main groups: polymorphonuclear leukocytes, or granulocytes, (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B cell and T cells. A third class of lymphocytes is Natural Killer (NK) cells. Cytotoxic T lymphocytes (CTL), helper T cells, and NKT cells are types of T cells.

Mammal: This term includes both human and non-human mammals. Similarly, the term "subject" includes both human and veterinary subjects.

Mitochondrial DNA heterogeneity: Any change of the mtDNA sequence of a cell, or clonal population of cells, that is due to a mutation (as distinct from any polymorphism) within a cell, when compared to known mtDNA sequence. A cell, or a clonal population of cells, with mitochondrial DNA heterogeneity has at least one mutation in the mtDNA, that distinguishes it from a cell, or a clonal population of cells, with a mtDNA sequence containing only polymorphisms. In one specific embodiment, mitochondrial heterogeneity is the divergence of the mtDNA sequence of an individual cell from the mtDNA sequence in the general population. Methods of detecting such a divergence, for example by comparison to a public database, are disclosed in U.S. Pat. No. 6,344,322. In another specific embodiment, mitochondrial heterogeneity is the sequence variation in an individual cell, compared to the sequence of a bulk, aggregate, or total, sample.

Mitochondrion: An organelle bound by a double membrane in which the reactions of the Krebs cycle and electron transport chain take place, resulting in the formation of ATP, $CO_2$, and water from acetyl CoA and ADP. Mitochondria are the organelles in which most of the ATP of the eukaryotic cell is produced. Mitochondria have their own DNA, mitochondrial DNA (mtDNA), and are thought to have evolved when an early eukaryote engulfed some primitive bacteria, but instead of digesting them, harnessed them to produce energy. Offspring inherit their mothers' mitochondria, and thus mtDNA has been useful in tracing human lineages.

The human mitochondrial genome is an approximately 16 kilobase circular, double stranded DNA that encodes 13 polypeptides of the mitochondrial respiratory chain, 22 transfer RNAs, and two ribosomal RNAs required for protein synthesis. The human mitochondrial genome contains a 1.1 kilobase noncoding control region, or D-loop. The D-loop is a stable intermediate formed during the replication of double-stranded mtDNA. Most of the sites within the control region do not vary among humans, however, the human mitochondrial genome has two hypervariable regions that are particularly susceptible to mutation and are hotspots for both germline and somatic mutations (Stoneking, *Am. J. Hum. Genet.* 67:1029-1032, 2000). Hypervariable segment (HSV) 1 is located between nucleotides 16024 and 16383, whereas HSV2 is located between nucleotides 57 and 372, of the mtDNA control region (between nucleotides 16,024 and 576), according to the reference sequence presented in Anderson et al. (*Nature,* 290:457-465, 1981) (see FIG. 1 and Table 1).

TABLE 1

Map position of the genes in the mtDNA control region

| Description (function) | Shorthand | Map Position (nucleotide position) |
|---|---|---|
| Hypervariable segment 1 | HV1 | 16,024-16,383 |
| Hypervariable segment 2 | HV2 | 57-372 |
| 7S DNA | 7S | 16,106-191 |
| H-strand origin | OH | 110-441 |
| Termination-associated sequence | TAS | 16,157-16,172 |
| Control element | mt5 | 16,194-16,208 |
| L-strand control element | mt3L | 16,499-16,506 |
| mt4 H-strand control element | mt4H | 371-379 |
| mt3 H-strand control element | mt3H | 384-391 |
| Conserved sequence block 1 | CSB1 | 213-235 |
| Conserved sequence block 2 | CSB2 | 299-315 |
| Conserved sequence block 3 | CSB3 | 346-363 |
| mtTF1 binding site 1 | TFB1 | 233-260 |
| mtTF1 binding site 2 | TFB2 | 276-303 |
| mtTF1 binding site 3 | TFB3 | 418-445 |
| mtTF1 binding site 4 | TFB4 | 523-550 |
| Replication primer | PR | 317-321 |
| L-strand promoter | PL | 392-445 |
| Major H-strand promoter | PH1 | 545-567 |

Abbreviations: mtTF1, mitochondrial transcription factor

Other regions within the mtDNA control region include (but are not limited to) a homopolymeric cytosine (C) tract located between nucleotides 303 and 315 in HVS2, the H-stand origin (OH, between nucleotides 110 and 441), the conserved sequence block (CSB, between nucleotides 213 and 235, 299 and 315, 346 and 363), the mt5 control element (between nucleotides 16,194 and 16,208), the L-strand control element (mt3L, between nucleotides 16,499 and 16,506), the termination-associated sequence (TAS, between nucleotides 16,157 and 16,172), the L-strand promoter (PL, between nucleotides 392 and 445), the major H-strand promoter (PH1, between nucleotides 545 and 567), the mitochondrial transcription factor binding site (TFB, between nucleotides 233 and 260, 276 and 303, 418 and 445, 523 and 550), the H-strand control elements (mt4H, between nucleotides 371 and 379, and mt3H, between nucleotides 384 and 391) and 7S DNA (between nucleotides 16,106 and 191).

Mutagen: An agent that gives rise to mutations in DNA. A mutagenic agent can be man-made or natural. Common mutagens include chemotherapeutic drugs, ethyl bromide, or 5-bromouracil. Mutagens can also be, for instance, a radioactive compound, such as radon found in the soil, ultraviolet radiation from the sun, X-rays, or radioisotopes used in nuclear medicine.

Mutation: A change of the DNA sequence within a gene or chromosome. In some instances, a mutation will alter a characteristic or trait (phenotype), but this is not always the case. Types of mutations include base substitution point mutations (for example, transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term generally refers to the subset of constitutional alterations that have arisen within the past few generations in a kindred and that are not widely disseminated in a population group.

Mutational frequency: A measure of the number of cells possessing at least one mtDNA mutation that distinguishes it from a cell with a mtDNA sequence containing only polymorphisms. The cells can be in vivo or in vitro. For example, mutational frequency is the number of hematopoietic cells, such as granulocytes or monocytes, which exhibit mtDNA heterogeneity in corresponding regions of mtDNA within a set of hematopoietic cells. A mutational frequency can also be a measure of the number of clonal populations (clones) of cells possessing at least one mtDNA mutation within corresponding regions of mtDNA that distinguishes it from a clonal population of cells with a mtDNA sequence containing only polymorphisms. For example, mutational frequency is a proportion of clonal populations of hematopoietic cells, such as clonal populations of $CD34^+$ cells, which exhibit mtDNA heterogeneity in corresponding regions of mtDNA within a set of clonal populations of hematopoietic cells. Mutational frequency can be represented as a proportion (for example, cells with at least one mutation in corresponding regions of mtDNA versus the total number of cells in a set) or as a percentage (for example, cells with at least one mutation in corresponding regions of mtDNA divided by the total number of cells in a set×100). For example, mutational frequency is the percentage of clonal populations of $CD34^+$ cells in a set of clonal populations of $CD34^+$ cells with one or more mutations within corresponding regions of mtDNA that distinguishes it from a clonal population of $CD34^+$ cells within the set containing a mtDNA sequence with only polymorphisms. In other examples, the mutational frequency is the proportion of cells or clonal populations of cells with a mutation in a particular mtDNA gene or at a particular mtDNA nucleotide position that distinguishes it from a cell or clonal population of cells containing a mtDNA sequence with only polymorphisms.

Since mtDNA is ten to 100 times more sensitive than genomic (nuclear) DNA to mutagenesis, the mutational frequency of a segment of mtDNA can be used to measure or estimate the frequency of mutations that occur in genomic DNA, or in other mtDNA sequences. In particular embodiments a measurement of the actual frequency that occurs in mtDNA is used to estimate (by correlation) the frequency in genomic DNA mutations. In other embodiments, mutational frequency is the measure of the number of mutations in the DNA (mitochondrial or genomic) of a cell over a period of time, compared to a control cell.

Myeloblast: An immature cell found in the bone marrow; it is the most primitive precursor in the granulocytic series, which matures to develop into the promyleocyte and eventually the granular leukocyte. Myeloblasts have fine, evenly distributed chromatin, several nucleoli, and a non-granular basophilic cytopalsm.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in an oligonucleotide/polynucleotide. A nucleotide sequence refers to the sequence of bases in an oligonucleotide/polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine is also a base that can be integrated into DNA or RNA in a nucleotide (dITP or ITP, respectively).

Polymorphism: The occurrence together in the same population of more than one allele or genetic marker at the same locus with the least frequent allele or marker occurring more frequently than can be accounted for by mutation alone. A variant in a sequence of a gene, usually carried from one generation to another in a population. Polymorphisms include those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, for instance, variants in the gene sequence that lead to gene products that are not functionally equivalent. This term also encompasses variations that produce no gene product, an inactive gene product, or increased or decreased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (for example, an alteration of a secondary structure such as a stem-loop, or an alteration of the binding affinity of the nucleic acid for associated molecules, such as polymerases, RNases, and so forth).

Progenitor cell: A "progenitor cell" is a cell that gives rise to progeny in a defined cell lineage. A "hematopoietic progenitor cell" is a cell that gives rise to cells of the hematopoietic lineage. One specific non-limiting example of a hematopoietic progenitor cell is a pluripotent stem cell expressing the CD34 cell surface marker.

Purified: The term "purified" does not require absolute purity; rather, it is intended as a relative term. Thus, for example, a purified cell preparation is one in which the cell referred to is more pure than the cell in its natural environment within a tissue. In one embodiment, a "substantially purified" population of a specific cell type is a composition of cells that includes less than about 20%, less than about 15%, or less than about 10% of cell of a different genotype or phenotype. Thus, a substantially purified population of cells includes greater than 80%, greater than 85%, or greater than 90% of the cells of interest. In another embodiment, a process that produces purified population of cells is a process that produces a population of cells so that at least 50% (or not less than 50%) of the resulting population is the cell type of interest.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Sample: Includes biological samples such as those derived from a human or other animal source (for example, blood, bone marrow, stool, sera, urine, saliva, tears, biopsy samples, histology tissue samples, cellular smears, moles, warts, etc.); bacterial or viral preparations; cell cultures; forensic samples; agricultural products; waste or drinking water; milk or other processed foodstuff; air; and so forth. Samples containing a small number of cells can be acquired by any one of a number of methods, such as needle aspiration, biopsy, or tissue scrapes.

Specific binding agent: An agent that binds substantially only to a defined target. Thus a hematopoietic cell specific binding agent is an agent that binds substantially to a hematopoietic cell. In one embodiment, the specific binding agent binds a cell surface marker on a hematopoietic cell, such as CD13, CD14, CD15, CD33, CD34, or CD64. In other embodiments, the specific binding agent is a monoclonal antibody or a polyclonal antibody that specifically binds a cell surface marker on a hematopoietic cell.

A variety of methods for making labeled specific binding agents are well known in the art. Detectable labels useful for such purposes are also well known in the art, and include radioactive isotopes such as $^{32}P$, fluorophores, chemiluminescent agents, and enzymes.

Stem cell: A "stem cell" is a pluripotent cell that gives rise to progeny in all defined lineages, for example hematopoietic lineages. In addition, limiting numbers of hematopoietic stem cells are capable of fully reconstituting a seriously immunocompromised subject in all blood cell types and their progenitors, including the pluripotent hematopoietic stem cell, by cell renewal.

Hematopoietic stem cells are self-regenerating, and also pluripotent in that they differentiate into several lineages, including lymphoid, myeloid and erythroid lineages. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers. Exposure to growth factors is believed to induce a stem cell to be dedicated to differentiate into a specific lineage. The stem cell population is known to constitute only a small percentage of the total number of leukocytes in bone marrow. Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Indeed, one injected cell should be able to reconstitute all of the hematopoietic lineages.

Subject: Any vertebrate that has a vascular system and has hematopoietic cells in the wild-type organism. The subject includes non-human mammals such as a monkey, mouse, rat, rabbit, pig, goat, sheep or cow. It also includes humans. It is understood that a cell or cell line in culture can be referred to as obtained from a subject even though the cell has been in culture for a length of time, even years.

Treatment: Refers to both prophylactic inhibition of a disease, and therapeutic interventions to alter the natural course of an untreated disease process, such as a tumor growth.

Tumor: A neoplasm that may be either malignant or non-malignant. Tumors originating in a particular organ (such as breast, prostate, bladder or lung) are primary tumors. Tumors of the same tissue type may be divided into tumor of different sub-types (a classic example being bronchogenic carcinomas (lung tumors) which can be an adenocarcinoma, small cell, squamous cell, or large cell tumor).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Specific Embodiments

Provided herein are methods of using mtDNA mutations to measure the mutational frequency of a mitochondrial DNA sequence. Also provided herein are methods for measuring the mutational frequency in hematopoietic cells.

One embodiment is a method of measuring a mutational frequency of a mitochondrial DNA sequence in a subject, which method involves isolating the test cells (such as stem cells or hematopoietic cells) from the subject, wherein the cells each contain at least one mitochondrion. In one specific example of the method, the cells are individual, non-clonally expanded hematopoietic cells. Although these specific examples are discussed with respect to hematopoietic test cells, it is understood that the method is not limited only to the use of hematopoietic cells. The method also includes sequencing corresponding regions of the mitochondrial DNA of the hematopoietic cells and determining a proportion of the hematopoietic cells exhibiting mtDNA heterogeneity within the sequenced corresponding regions of the mitochondrial DNA, wherein the proportion corresponds to the mutational frequency of the mitochondrial DNA sequence in the subject. In one specific example of the method, the mitochondrial DNA is amplified prior to sequencing.

Specific examples of the method involve multiple clonal populations of hematopoietic cells, wherein determining the proportion of the hematopoietic cells exhibiting mtDNA heterogeneity within corresponding regions involves determining the proportion of clonal populations possessing at least one mitochondrial DNA mutation that distinguishes it from clonal populations of cells with a mtDNA sequence containing only polymorphisms. In one example of the method, the mitochondrial DNA from the multiple clonal populations is extracted without amplification prior to sequencing.

The hematopoietic cells of the method include, for example, $CD34^+$ cells, granulocytes, monocytes, or macrophages. The hematopoietic cells are isolated from bone marrow, peripheral blood, or umbilical cord blood. In particular examples, the cells are stem cells, such as hematopoietic stem cells, such as $CD34^+$ cells.

Another specific example of the method involves isolating the cells, which method involves obtaining a biological sample from the subject, contacting hematopoietic cells in the biological sample with a specific binding agent attached to a detectable label, and purifying the hematopoietic cells contacted with the specific binding agent. The biological sample includes bone marrow, peripheral blood, or umbilical cord blood. The detectable label includes a fluorescent agent, a chemiluminescent agent, or a radioisotope.

In specific examples of the method, the subject is a human. The subject can have a disease (or be suspected of having a disease) that is or may be associated with a mtDNA or a non-mitochondrial DNA mutation. In another example of the method, the subject has been subjected to a mutagenic treatment, and the method assesses the mutagenic effect of the treatment. Mutagenic treatment includes chemotherapy or radiation.

In one example of the method the mitochondrial DNA sequence from the cells (such as hematopoietic cells) has at least one mutation that distinguishes it from cells with a mtDNA sequence containing only polymorphisms and that is not present in the mitochondrial DNA sequence from a control cell (such as a hematopoietic cell). The mutation includes a point mutation, a polymorphism, a frame-shift mutation, a missense mutation, a nonsense mutation, a silent mutation, or a deletion mutation. The mutation can be, for example, in the mtDNA control region or in the mtDNA coding region. In one specific example of the method, the mutation is in a homopolymeric C tract of a mitochondrial DNA control region. In other specific examples, the mutation is in the CO1 gene or in the Cytb gene of the mtDNA coding region. In certain examples of the method, a mutation is selected that is known to be associated with a particular disease, and the frequency of that mutation in the mtDNA is determined by this method as a measure of the prevalence of that mutation in the cell population from which the mtDNA was obtained.

This disclosure further provides a method of measuring a mutational frequency of a mitochondrial DNA sequence in a subject, which method involves isolating the test cells (such as the hematopoietic cells) from the subject, wherein the test cells each contain at least one mitochondrion, expanding the test cells into multiple clonal populations of hematopoietic cells, extracting mitochondrial DNA from the multiple clonal populations of hematopoietic cells, sequencing corresponding regions of the mitochondrial DNA of the multiple clonal populations, and determining a proportion of the multiple clonal populations of hematopoietic cells exhibiting mtDNA heterogeneity within the corresponding regions of the mitochondrial DNA, wherein the proportion corresponds to the mutational frequency of the mitochondrial DNA sequence in the subject. In one specific example of the method, the mitochondrial DNA is amplified prior to sequencing.

The hematopoietic cells of the method include $CD34^+$ cells, granulocytes, monocytes, or macrophages. The hematopoietic cells are isolated from bone marrow, peripheral blood, or umbilical cord blood.

Another specific example of the method involves isolating the hematopoietic cells, which method involves obtaining a biological sample from the subject, contacting hematopoietic cells in the biological sample with a specific binding agent attached to a detectable label, and purifying the hematopoietic cells contacted with the specific binding agent. The biological sample includes bone marrow, peripheral blood, or umbilical cord blood. The detectable label includes a fluorescent agent, a chemiluminescent agent, or a radioisotope.

In specific examples of the method, the subject is a human. The subject can have a disease that is or may be associated with a mtDNA or a non-mitochondrial DNA mutation. In another example of the method, the subject has been subjected to a mutagenic treatment. Mutagenic treatment includes chemotherapy or radiation.

In one example of the method, the mitochondrial DNA sequence from the clonal populations of hematopoietic cells has at least one mutation that distinguishes it from clonal populations of hematopoietic cells with a mtDNA sequence containing only polymorphisms and that is not present in the mitochondrial DNA sequence from a control clonal population of hematopoietic cells. The mutation includes a point mutation, a polymorphism, a frame-shift mutation, a missense mutation, a nonsense mutation, a silent mutation, or a deletion mutation. The mutation can be, for example, in the mtDNA control region or in the mtDNA coding region. In one specific example of the method, the mutation is in a homopolymeric C tract of a mitochondrial DNA control region. In other specific examples, the mutation is in the CO1 gene or in the Cytb gene of the mtDNA coding region.

Another embodiment is a method of estimating a mutational frequency of a genomic DNA sequence in a subject, which method involves isolating hematopoietic cells in the subject, wherein the hematopoietic cells each contain at least one mitochondrion, expanding the hematopoietic cells into multiple clonal populations of hematopoietic cells, extracting mitochondrial DNA from the multiple clonal populations of hematopoietic cells, sequencing a region of the mitochondrial DNA, determining a proportion of the multiple clonal populations of hematopoietic cells exhibiting mtDNA heterogeneity within the sequenced region, and correlating the mutational frequency of the mitochondrial DNA to an estimated mutational frequency of genomic DNA from the same subject, thereby estimating the mutational frequency of the genomic DNA sequence in the subject. In one specific example of the method, the mitochondrial DNA is amplified prior to sequencing.

The hematopoietic cells of the method include $CD34^+$ cells, granulocytes, monocytes, or macrophages. The hematopoietic cells are isolated from bone marrow, peripheral blood, or umbilical cord blood.

Another specific example of the method involves isolating the hematopoietic cells, which method involves obtaining a biological sample from the subject, contacting hematopoietic cells in the biological sample with a specific binding agent attached to a detectable label, and purifying the hematopoietic cells contacted with the specific binding agent. The biological sample includes bone marrow, peripheral blood, or umbilical cord blood. The detectable label includes a fluorescent agent, a chemiluminescent agent, or a radioisotope.

In specific examples of the method, the subject is a human. The subject can have a disease that is or may be associated with a mtDNA or a non-mitochondrial DNA mutation. In another example of the method, the subject has been subjected to a mutagenic treatment. Mutagenic treatment includes chemotherapy or radiation.

In one example of the method, the mitochondrial DNA sequence from the clonal populations of hematopoietic cells has at least one mutation that distinguishes it from clonal populations with a mtDNA sequence containing only polymorphisms and that is not present in the mitochondrial DNA sequence from a control clonal population of hematopoietic cells. The mutation includes a point mutation, a polymorphism, a frame-shift mutation, a missense mutation, a nonsense mutation, a silent mutation, or a deletion mutation. The mutation can be, for example, in the mtDNA control region or in the mtDNA coding region. In one specific example of the method, the mutation is in a homopolymeric C tract of a mitochondrial DNA control region. In other specific examples, the mutation is in the CO1 gene or in the Cytb gene of the mtDNA coding region.

Also provided is a method of screening for an agent that increases the mutational frequency of a hematopoietic cell, which method involves contacting isolated hematopoietic cells with the agent to produce treated hematopoietic cells, wherein the hematopoietic cells each contain at least one mitochondrion. The method also involves sequencing corresponding regions of the mitochondrial DNA of the hematopoietic cells and determining a proportion of the hematopoietic cells that distinguishes it from cells with a mtDNA sequence containing only polymorphisms within the sequenced corresponding regions of the mitochondrial DNA, wherein the proportion corresponds to the mutational frequency of the mitochondrial DNA sequence in the treated hematopoietic cells. In one specific example of the method, the mitochondrial DNA is amplified prior to sequencing.

The method further involves comparing the mutational frequency of the treated hematopoietic cells to a mutational frequency of hematopoietic cells that were not contacted with the agent, wherein an increase in the mutational frequency of the treated hematopoietic cells, compared to the mutational frequency of hematopoietic cells that were not contacted with the agent, indicates that the agent increases the mutational frequency of the hematopoietic cell, thereby screening for the agent that increases the mutational frequency of the hematopoietic cell.

Another embodiment is a method of screening for an agent that increases the mutational frequency of a hematopoietic cell, which method involves contacting isolated hematopoietic cells with the agent to produce treated hematopoietic cells, wherein the hematopoietic cells each contain at least one mitochondrion, and expanding the hematopoietic cells into multiple clonal populations of hematopoietic cells. The method also involves extracting mitochondrial DNA from the multiple clonal populations of hematopoietic cells, sequencing corresponding regions of the mitochondrial DNA of the multiple clonal populations, and determining a proportion of the multiple clonal populations of hematopoietic cells that distinguishes it from clonal populations with a mtDNA sequence containing only polymorphisms within the corresponding regions of the mitochondrial DNA, wherein the proportion corresponds to the mutational frequency of the mitochondrial DNA sequence in the subject. In one specific example of the method, the mitochondrial DNA is amplified prior to sequencing.

The method further involves comparing the mutational frequency of the treated hematopoietic cells to a mutational frequency of hematopoietic cells that were not contacted with the agent, wherein an increase in the mutational frequency of the treated clonal populations of hematopoietic cells, compared to the mutational frequency of clonal populations of hematopoietic cells that were not contacted with the agent, indicates that the agent increases the mutational frequency of the hematopoietic cell, thereby screening for the agent that increases the mutational frequency of the hematopoietic cell.

In specific examples of the method, the agent includes a small molecule, a chemical compound, a radioisotope, a protein, a peptide, or a peptidomimetic. The chemical compound includes a chemotherapeutic drug.

The hematopoietic cells of the method include $CD34^+$ cells, granulocytes, monocytes, or macrophages. The hematopoietic cells are isolated from bone marrow, peripheral blood, or umbilical cord blood.

In specific examples, the mutation includes a point mutation, a polymorphism, a frame-shift mutation, a missense mutation, a nonsense mutation, a silent mutation, or a deletion mutation. The mutation can be, for example, in the mtDNA control region or in the mtDNA coding region. In one specific example of the method, the mutation is in a homopolymeric C tract of a mitochondrial DNA control region. In other specific examples, the mutation is in the CO1 gene or in the Cytb gene of the mtDNA coding region.

IV. Method of Detecting Mutational Frequency in Cells

Prior to this disclosure, there had not been an adequate method available to determine the frequency of genetic mutations in intact animals, including humans. Disclosed herein are methods of detecting and/or measuring the mutational frequency in cells, such as hematopoietic cells. The cells can be in vivo or in vitro. In one embodiment, the mutational frequency is the number of cells within a set of cells exhibiting mtDNA heterogeneity within corresponding regions of mtDNA. In another embodiment, the mutational frequency is the number of cells within a set of cells exhibiting at least one DNA mutation that distinguishes it from other cells in the set containing a mtDNA sequence with only polymorphisms within the corresponding region of mtDNA. For example, the mutational frequency may be the number of granulocytes within a set of granulocytes exhibiting at least one DNA mutation that distinguishes it from other granulocytes in the set containing a mtDNA sequence with only polymorphisms within the corresponding region of mtDNA. In another embodiment, the mutational frequency is the number of clonal populations of cells exhibiting mtDNA heterogeneity within corresponding regions of mtDNA. In another embodiment, the mutational frequency is the number of clonal populations of cells within a set of clonal populations of cells exhibiting at least one DNA mutation that distinguishes it from other clonal populations in the set containing a mtDNA sequence with only polymorphisms within corresponding regions of mtDNA. Mutational frequency can be represented as a proportion (for instance cells in a set with at least one mutation that distinguishes it from other cells in the set containing a mtDNA sequence with only polymorphisms in corresponding regions of mtDNA versus the total number of cells in a set) or as a percentage (for instance cells in the set with at least one mutation that distinguishes it from other cells in the set containing a mtDNA sequence with only polymorphisms in corresponding regions of mtDNA, divided by the total number of cells in a set ×100). In a specific, non-limiting example, the mutational frequency is the number of $CD34^+$ clones (clonal populations of cells) which exhibit mtDNA heterogeneity in corresponding regions of mtDNA within the set of $CD34^+$ clones. In another specific, non-limiting example, the mutational frequency is the percentage of clonal populations of $CD34^+$ cells which exhibit mtDNA heterogeneity in corresponding regions of mtDNA within a set of clonal populations of $CD34^+$ cells. In other specific, non-limiting examples, the mutational frequency is the number or the percentage of granulocytes which exhibit mtDNA heterogeneity in corresponding regions of mtDNA within a set of granuloctyes.

Disclosed methods involve isolating a cell from a subject, wherein the isolated cell contains at least one mitochondrion. In one embodiment, at least two hematopoietic cells are isolated. In other embodiments, at least 2, at least 5, at least 10, at least 20, at least 50, at least 75, at least 96, at least 100, at least 500, at least 1000, or more hematopoietic cells are isolated. Each cell isolated can contain hundreds of mitochondria and each mitochondrion can contain multiple copies of mtDNA. In one embodiment, the cells are isolated from a healthy (for example, normal for a specific condition) subject. In another embodiment, the cells are isolated from a subject having a disease. The disease can be any disease, including for instance a neoplasia, an autoimmune disease, or a congenital disease. In another embodiment, the subject is suffering from senescence (aging). In certain embodiments, the isolated cells are human cells. The cell in preferred embodiments is viable, such that it can be replicated for at least one generation outside of the subject (in vitro).

Cells can be isolated directly from a subject or from a biological sample that is obtained from the subject. Biological samples can be obtained from any part of the body of the subject, by any means known to one of ordinary skill in the art. The biological sample can include blood, urine, stool, sera, saliva, tears, biopsy samples, histological samples, and the like. Hematopoietic cells (blood cells), for example, can be obtained from bone marrow, peripheral blood, or umbilical cord blood. In one embodiment, hematopoietic cells are obtained by bone marrow aspiration, for example from the pelvic bone of the subject. In another embodiment, hematopoietic cells are obtained by phlebotomy.

Once the hematopoietic cells are obtained, a specific hematopoietic cell, or class of cells of interest can be isolated. Methods of isolating cells, and particularly individual types or classes of cells, are well known in the art. In one embodiment, cells expressing a particular cell surface marker, or a collection of cell surface markers, are selected. Examples of cell surface markers include, but are not limited to, Sca-1, CD11b, CD13, CD14, CD15, CD33, CD34, and CD64. In one embodiment, a method of selecting a cell that expresses specific cell surface markers involves the use of specific binding agents, such as antibodies, that recognize the cell surface marker. Antibodies useful in sorting methods can be monoclonal or polyclonal antibodies.

In order to identify the cells to be isolated, detectable labels can be attached to a specific binding agent, such as an antibody that specifically binds a cell surface marker. Attachment of the detectable label to an antibody can be accomplished using any number of means known to those of ordinary skill in the art. In some embodiments, the antibody is attached to a detectable label by covalent or non-covalent means. Examples of detectable labels include radioactive isotopes, chemiluminescent agents, or fluorophores. In some embodiments, cells are selected using FACS (fluorescence activated cell sorting).

In one embodiment, purified populations of $CD34^+$ cells are isolated with immobilized antibodies, for example anti-CD34 antibodies. In other embodiments, granulocytes, monocytes, or macrophages are isolated with immobilized antibodies, for example granulocytes are isolated with anti-CD13 or anti-CD33 antibodies and mature granulocytes are isolated with anti-CD15 antibodies. Myeloblasts are isolated with anti-CD34 antibodies and anti-CD13 or anti-CD33 antibodies. Monocytes are isolated with anti-CD14 or anti-CD64 antibodies. Antibodies can be immobilized on particles, such as sepharose beads or magnetic beads. The particles can be in the form of a slurry or contained within an apparatus, such as a column. A particular embodiment uses magnetic cell sorting such as, for example, the BD IMag Cell Separation System (Becton Dickinson, San Diego, Calif.) or the MACS Separation System (Miltenyi Biotec, Auburn, Calif.). Magnetic cell sorting involves the use of a monoclonal antibody covalently bound to the surface of a magnetic bead, where the antibody can specifically bind an epitope on a cell surface marker present on the cells being selected. For example, to isolate a cell expressing CD34 (a $CD34^+$ cell) from a mixture of cells, anti-CD34 monoclonal antibodies bound to magnetic beads are used. Only $CD34^+$ cells are specifically bound by the antibodies and retained by the beads, thereby separating, or isolating, $CD34^+$ cells from the other cells in the mixture. The remaining, unbound cells do not express CD34 and are $CD34^-$ cells. Immobilized $CD34^+$ cells can be released from the magnetic beads under the appropriate conditions.

In another embodiment, purified populations of $CD34^+$ cells are isolated using flow cytometry. By way of example, in flow cytometry, CD34 antibodies attached to a detectable label specifically bind surface CD34 on CD34-expressing cells. In a further embodiment, granulocytes that express CD13 or CD33 are isolated by flow cytometry using anti-CD13 or anti-CD33 antibodies attached to a detectable label. An example of a detectable label used in flow cytometry is a fluorophore, such as fluorescein or phycoerythrin. Labeled CD34-expressing cells can then be identified by a flow cytometer and "sorted." Sorting involves the mechanical separation of fluorescently-labeled cells from cells that do not fluoresce, such as, for example, those cells that do not express the CD34 cell surface marker. Flow cytometry can sort cells that are labeled with at least one, at least two, at least three, or more antibodies attached to distinguishable detectable labels, thus cells can be isolated based on the expression of one or more or any combination of two or more cell surface markers.

In some embodiments, $CD34^+$ cells or $CD33^+$ cells are sorted into a culture plate, and optionally individual cells are sorted into individual growing chambers. The culture plate can be any shape or size. In one embodiment, the culture plate is a multi-chamber (multi-well) plate. A multi-well plate can have any number of individual wells, or chambers. A specific, non-limiting example of a multi-well plate is a microtiter plate containing 96 wells, though other examples are known to those of ordinary skill in the art. A flow cytometer can be programmed to sort any number of cells into a single well; in particular embodiments, cells are sorted so that only one is placed in each well or chamber.

When a cell is deposited in a particular growth chamber, a colony of cells can be formed under the appropriate growth conditions. A group, or colony, of cells that is derived, or expanded, from a single cell is referred to as a clonal population of cells (for instance a clone). Thus, the deposition of single cells in individual growth chambers ensures that the cells comprising the resultant clonal population are genetically alike and the DNA of the clonal population is a reflection of the DNA of the cell initially deposited in the well. Such a clonal population may include, for example, five or fewer cells, at least 2 cells, at least 5 cells, at least 10 cells, at least 20 cells, at least 100 cells, at least 200 cells, at least 500 cells, at least 1000 cells or at least 10,000 cells.

By way of example, $CD34^+$ cells can be sorted by single cell deposition into a 96 well microtiter plate, or in microcentrifuge tubes. In one specific, non-limiting example, $CD34^+$ cells are labeled with a phycoerythrin (PE) anti-CD34 monoclonal antibody and sorted with a MoFlo cytometer and CyClone automated cloner in a 0.5 single drop mode, such that only a single cell is deposited in each well of the microtiter plate. In another specific, non-limiting example, granulocytes are labeled with a PE anti-CD33 monoclonal antibody and sorted with a MoFlo cytometer and CyClone automated cloner in a 0.5 single drop mode, such that only a single cell is deposited in individual microcentrifuge tubes.

The wells of the microtiter plate or other culture plate in many embodiments contain a growth medium. The growth medium can be any growth medium known to one of ordinary skill in the art that will support the growth of cells in culture. The growth medium can contain, for example, agar or methylcellulose (or another polymer) if the growth of cell colonies is desired. Alternatively, the growth medium can contain liquid growth medium if the growth of cells in suspension is desired. In addition, the growth medium can contain growth factors, or cytokines, such as, but not limited to, stem cell factor, Flt-3, thrombopoietin, or G-CSF. The growth medium can also contain other components, for example fetal calf serum, which are beneficial to support the optimized growth of cells. The particular combination of components included in the growth medium will vary depending on the cell type deposited in the well and/or the type of cell desired at the end of the culture period.

The cells can be maintained in culture for any length of time, depending in part on the degree of expansion desired and the generational time of the cells. In one embodiment, the cells are maintained in culture at least one day. In other embodiments, the cells are maintained in culture at least two days, at least three days, at least four days, at least five days, at least six days, at least ten days, at least 15 days, or at least 20 days. Alternatively, the time in culture can be calculated based on the number of cell divisions or generations.

In order for mtDNA heterogeneity and/or mutational frequency to be determined, cell colonies that grow in the culture wells can be removed and DNA extracted therefrom. Optionally, it is believed to be beneficial to isolate the mitochondria prior to extracting the mtDNA and/or the genomic (nuclear) DNA. Methods of mitochondria isolation are well known to those of ordinary skill in the art (Barja, *J. Bioenerg. Biomembr.* 34:227-233, 2002; Rajapakse et al., *Brain Res. Brain Res. Protoc.,* 8:176-183, 2001). In one embodiment, individual, isolated hematopoietic cells are lysed, such as by sonication, prior to sequencing the mtDNA.

In order to determine the heterogeneity of mtDNA sequences from individual cells, such as granulocytes, or cells deposited and expanded to form a colony in the culture wells, such as $CD34^+$ cells, mtDNA is sequenced and the presence of mutations in a specific region (for instance, the hypervariable region, the homopolymeric C tract, or a gene in the coding region, such as CO1 or Cytb) or at a specific nucleotide position of the mtDNA can be assessed. Primers that stably bind, or hybridize, to mtDNA can be used. Any region of the mtDNA or any number of base pairs can be sequenced. In one embodiment, the mtDNA control region is sequenced, for instance 1121 base pairs are sequenced. In another embodiment, the mtDNA coding region, for instance the Cytb gene (910 base pairs) or the CO1 gene (1390 base pairs), are sequenced. Alternatively, at least 50 base pairs, at least 100 base pairs, at least 200 base pairs, at least 300 base pairs, at least 500 base pairs, at least 750 base pairs, at least 1000 base pairs, at least 1100 base pairs, at least 1200 base pairs, at least 1500 base pairs, at least 2000 base pairs, or at least 3000 base pairs are sequenced. In certain specific embodiments, the entire mtDNA is sequenced.

Optionally, at least some of the DNA isolated from the cultured cells is amplified, for example by polymerase chain reaction (PCR), prior to sequencing. In one embodiment, the DNA is subjected to nested gene amplification (Erickson and Castora, *Biochim. Biohphys. Acta* 1181:77, 1993; Khrapko et al., *Nucleic Acids Res.* 27:2434, 1999). In nested gene amplification, at least two pairs of primers are used to amplify the DNA, where one pair of primers hybridizes to a region that is within the region amplified by a different pair of primers. When increased specificity of the amplified product is desired, nested gene amplification can also be performed with at least three pairs, at least four pairs, or more pairs of primers.

Once a mtDNA sequence from an individual cell or from a clonal population of cells is determined, it can be compared to a corresponding region of a known mtDNA sequence such as, for example, the revised Human mtDNA Cambridge Reference sequence (Andrews et al., *Nat. Genet.* 23:147, 1999; Kogelnik et al., *Nucleic Acids Res.* 26:112, 1998) in order to identify changes in the mtDNA sequence that are due to mutations (mtDNA heterogeneity), as opposed to polymorphisms. The mutational frequency of mtDNA can then be determined by calculating the number of cells within a set of cells, or the number of clonal populations of cells within the set of clonal populations of cells, having at least one mutation (the number of cells or clonal populations of cells exhibiting mtDNA heterogeneity) in corresponding regions of a mtDNA sequence, when compared to the mtDNA polymorphisms described in the revised Human mtDNA Cambridge Reference sequence. In some embodiments, the mutational frequency is the number of cells or clonal populations of cells with a mutation in a particular mtDNA gene or at a particular mtDNA nucleotide position that distinguishes it from a cell or clonal population of cells containing a mtDNA sequence with only polymorphisms.

A mutation in the mtDNA and/or the genomic DNA can be a point mutation, a polymorphism, a deletion mutation, a silent mutation, a frame-shift mutation, a nonsense mutation or a missense mutation (not all of which are mutually exclusive categories). The mutation can arise in any way, for instance as a result of a cell being exposed to a mutagenic agent, such as during the course of treatment for a disease. The mutagenic agent can be man-made or natural. In one embodiment, the mutagenic agent is a chemical agent, such as a chemotherapeutic drug. In other embodiments, the mutagenic agent is a radioactive agent or ultraviolet light. A mutagenic agent, such as a toxic drug or chemical, can result in the generation of at least one reactive oxygen species.

Mutations can also be due to a genetic disease or defect, such as a defect in a component of a DNA repair or maintenance mechanism of the cell.

Provided embodiments of the method to detect mutations are performed using hematopoietic cells isolated from the subject. Hematopoietic cells are readily obtained from the bone marrow, the umbilical cord, or the peripheral blood and thus are a convenient source of DNA. However, the method is not limited to the use of hematopoietic cells.

Any method can be used to detect differences between sequences. In one embodiment, differences between sequences are determined by the direct sequencing of two or more sequences, followed by the comparison of the sequences. In a particular embodiment, amplification of the DNA molecules is performed prior to sequencing. In a specific, non-limiting example, sequencing is verified by subcloning the PCR products into pCR®02.1-TOPO® vector and transforming competent *E. coli* (TOP10 cells) using the TOPO TA™ cloning kit (Invitrogen, Carlsbad, Calif.). In another embodiment, comparative sequencing based upon heteroduplex detection is used to identify sequence differences that exist between different DNA sequences, such as mtDNA sequences from two or more clones, for instance between one or more samples and a control. An example of a technique that assays for heteroduplex formation after DNA denaturation is WAVE™ denaturing high-performance liquid chromatography (Transgenomics, Inc., Omaha, Nebr.).

Optionally, analysis of the amplified mtDNA sequence from a first cell or clonal population, and its comparison to the amplified mtDNA of a corresponding region from a second, or more, cell or clonal population, reveals that the mtDNA isolated from a first cell or clonal population has at least one mutation that is not present in the corresponding region of the mtDNA isolated from the second, or more, cell or clonal population. The second, or more, clonal population can be derived from the same biological sample as the first clonal population, or from a second biological sample. The second biological sample can be obtained from the same subject, or from a different subject, as the first biological sample. In one embodiment, the first biological sample is obtained from a subject that has undergone treatment of a disease (for example by the administration of chemotherapy for a tumor), whereas the second biological sample is obtained from a control subject who has not undergone the treatment. In another embodiment, the first biological sample is obtained from a subject before undergoing treatment and the second biological sample is obtained from a subject following treatment. In a particular embodiment, the first and second biological samples are obtained from the same subject.

Since mtDNA is ten to 100 times more sensitive than genomic (nuclear) DNA to mutagenesis, the mutational frequency of mtDNA can be used to measure the frequency of mutations that occur in genomic DNA, or in other mtDNA sequences. In particular embodiments a measurement of the actual mutational frequency that occurs in mtDNA is used to estimate (by correlation) the frequency in genomic DNA.

In one embodiment, hematopoietic stem cells ($CD34^+$ cells), which are known to circulate in the peripheral and umbilical cord blood, are isolated from the peripheral or umbilical cord blood in order to detect the mutational frequency of the mtDNA, the genomic DNA and, in some embodiments, the mutational frequency of the cell. The isolated cells can then be sorted (for instance, using a method similar to those described above) into individual growth chambers, for instance individual wells of a 96-well microtiter plate. The cells are then cultured to produce clonal populations of cells, from which DNA (for instance, mtDNA) can then be amplified and analyzed, for instance by sequencing a region of the DNA, to determine the mutational frequency of mtDNA, genomic DNA, or both. Due to the relatively low density of $CD34^+$ cells in peripheral blood compared to bone marrow, special precautions are usually taken during the isolation of $CD34^+$ cells from peripheral blood to ensure a maximum yield of these cells. Such steps include the collection of large volumes of peripheral blood and lengthy sorting times.

The provided methods can be used to monitor, or track, individual stem cells as they contribute to hematopoiesis. For example, a unique sequence of mtDNA (a mtDNA profile) in a $CD34^+$ cell is also present in a proportion of circulating hematopoietic cells, such as granulocytes, lymphocytes, or erythrocytes, that are the progeny of the $CD34^+$ cell expressing that particular mtDNA profile. In one embodiment, different $CD34^+$ cells isolated from a subject have different mtDNA profiles. Clonal expansion of the $CD34^+$ cells with different mtDNA profiles, under conditions that allow for the differentiation of the $CD34^+$ cells into all hematopoietic cell types, can be performed for different lengths of time. Thus, the number of hematopoietic cells expressing a particular mtDNA profile at different time points in the differentiation process is an indication of the proportion and/or types of hematopoietic cells that are descendants of a particular $CD34^+$ stem cell. The proportion of circulating hematopoietic cells expressing a particular mtDNA profile, for example the proportion of granulocytes within the population of hematopoietic cells in a peripheral blood sample obtained from a subject, can then be used to determine the proportion of $CD34^+$ stem cells contributing to blood cell production in that subject. The proportion of circulating hematopoietic cells expressing the particular mtDNA profile can be measured at any time in the subject, such that the proportion of circulating hematopoietic cells expressing the particular mtDNA profile can be monitored, or tracked, over time in a subject. The proportion of stem cells (or the proportion of active stem cells), based on the degree of mtDNA heterogeneity of circulating granulocytes, can be statistically measured (see, for example, Abkowitz et al., *Proc. Natl. Acad. Sci. U.S.A.,* 92:2031-2035, 1995)

The provided methods can also be used to isolate, or identify, a cell in a sample obtained from a subject, where the cell has a set of mtDNA mutations (mtDNA profile) linked to a particular disease. A mtDNA profile can be causative or associative, with respect to a disease. In one embodiment, a cell isolated from a subject and expanded into a clonal population of cells, using the methods described herein, has a mtDNA profile that indicates the subject is predisposed to a disease. In other embodiments, a cell isolated from a subject and expanded into a clonal population of cells has a mtDNA profile that indicates the subject has a disease or is having a recurrence of a disease. In a specific, non-limiting example, a subject with a disease, such as leukemia, has a proportion of abnormal hematopoietic cells, within a set of hematopoietic cells obtained from the subject, which abnormal cells have a particular mtDNA profile specific to the abnormal cells (the mtDNA mutational frequency of the subject). Following treatment for the disease, the mtDNA profile is monitored in cells obtained from the subject, where detection of the same proportion or more of cells expressing the particular mtDNA profile following treatment (for instance the mtDNA mutational frequency is unchanged in the subject) is an indication that the treatment was not effective in eradicating the abnormal cells. Detection of a lower proportion of cells expressing the particular mtDNA profile following treatment (for example, the mtDNA frequency has decreased in the subject) is an indication that the treatment has an effect on eradicating the abnormal cells. The cells can be obtained from the subject after any period of time subsequent to a treatment, or a series of treatments, for instance about one week, about two weeks, about one month, about two months, about four months, about six months, about one year, about five years or more following treatment of the subject for the disease.

V. Methods of Determining Mutational Effect of Mutagens on mtDNA in Cells

Also disclosed herein are methods of determining the effect of mutagens on cells. These methods involve the exposure of a cell, or a clonal population of cells, to a mutagen, or a potential or suspected mutagen, and the subsequent measurement of the mutational frequency of the DNA of the cell, or clonal population of cells, by a method described herein. The mutational frequency determined in the cell, or in clonal population of cells, that is exposed to a mutagen can be compared to the mutational frequency of a control cell, or clonal population of cells, that has not been exposed to the mutagen, or that has been exposed to a different condition, such as the mutagen and a blocking agent, or a different amount of the mutagen, or another mutagen, etc.

These methods can be used to measure the mutational effect of any agent on the DNA (genomic (nuclear), or mtDNA, or both) of a cell. The agent can be a drug that is mutagenic, for example by directly damaging DNA, such as by DNA cross-linkage, or by increasing the generation of at least one reactive oxygen species in the cell. For instance, the agent can be a chemical compound used to treat a disease, such as a chemotherapeutic drug. Examples of drugs that can have a mutational effect on the DNA include alkylating agents, such as busulfan, methylmethane sulfonate, or dimethylnitrosamine; cross-linking agents, such as mitomycin C; or agents that inhibit DNA replication by intercalative (for example, actinomycin D) or non-intercalative (for example, hydroxyurea) mechanisms. Another specific, non-limiting example of a DNA damaging agent is etoposide. DNA damaging agents also include radiation from an X-ray, or a radioisotope. Optionally, the method of determining the effect of mutagens on cells can be used to predict the prevalence of mutations in the cells of a subject following treatment of a disease, for instance, a treatment that involves application of any of these agents.

The method also can be used to screen for the potential mutagenic character of chemicals and drugs. In such embodiments, the clonal expansion and mtDNA analysis method described herein is used to determine the mutational frequency in a cell (for example, a cell grown in vitro) before and after the cell (or a clonally identical or similar cell) is exposed to a known or putative mutagenic chemical or drug. The cell, or a clonal population of cells, to be exposed to the putative mutagenic chemical or drug is in some instances obtained from a relatively young subject, such as a child, or a middle-aged subject, or an elderly subject, in order to determine the effect of the mutagenic agent on cells of different generational age. The cell, or clonal population of cells, can be obtained from a healthy (for example, normal for a specific condition) subject or from a subject that has a known or suspected background mutation(s) in their mtDNA or their genomic (nuclear) DNA. Typically, the cell, or clonal population of cells, has not previously been exposed to a mutagenic agent. In some instances the cell, or clonal population of cells, is obtained from a subject that has had prior exposure to a mutagenic agent. The prior exposure can be to the same mutagenic agent or to a different mutagenic agent. The relative mutagenic potential of the chemical or drug is then calculated based on the increase in mutational frequency in the mtDNA that results from the exposure, compared to a control mtDNA or genomic DNA.

Optionally, the known or putative mutagenic chemical or drug can be administered to a whole animal, such as a rabbit or a mouse or a primate. DNA from cells obtained from the animal subsequent to administration of the mutagenic chemical or drug can be compared to DNA from cells obtained from the animal before administration of the mutagenic chemical or drug, or to cells from a control animal.

In one embodiment of the method of screening for a mutagenic agent, at least two isolated cells are contacted, or treated, with an agent. In other embodiments, at least 5, at least 10, at least 20, at least 50, at least 75, at least 96, at least 100, at least 500, at least 1000, or more isolated hematopoietic cells are contacted, or treated, with an agent. Optionally, the treated cells are subsequently expanded into clonal populations of cells to produce treated clonal populations of cells. Untreated cells or clonal populations of cells can serve as control, or reference, cells or clonal populations of cells. In order to identify or quantify mutations in the nucleic acid sequence of the mtDNA of the treated cells, DNA is extracted from treated and untreated clonal populations of cells, then the mtDNA is sequenced. In another embodiment, the mtDNA is amplified prior to sequencing. In yet another embodiment, the treated and untreated cells are lysed and the DNA is amplified prior to sequencing. Comparison of the sequence of the mtDNA from the treated cells or clonal populations of cells with the sequence of a corresponding region of mtDNA from a control cell or control clonal populations of cells that was not contacted with the agent can determine the number (or proportion or percentage) of clonal populations of cells exhibiting mtDNA heterogeneity (for example, the number of clonal populations with at least one mutation that distinguishes it from clonal populations containing a mtDNA sequence with only polymorphisms) in the sequenced region of the mtDNA from the treated cells and from the untreated cells. An increase in the percent or proportion of the treated clonal populations of cells with at least one mutation in the corresponding regions of mtDNA (an increase in mtDNA mutational frequency), compared to the untreated clonal populations of cells, indicates that the agent has a mutagenic effect on the cell and increases the mutational frequency of the cell.

In another embodiment of the method of screening for a mutagenic agent, a single cell is obtained by limiting dilution, as described herein, and expanded to obtain a uniform clonal population of cells with a homogenous mtDNA sequence. In this embodiment, the clonal population is divided into experimental (treated) and control groups. The cells in the experimental group are treated with an agent, for instance a mutagen, or a potential or suspected mutagen, whereas cells in the control group are not treated. Cells in the experimental group can be treated for various time intervals, or repeatedly. mtDNA heterogeneity of the control and treated cells is determined at any time following treatment. mtDNA heterogeneity is determined using any of the methods described herein, for example by sequencing, and the mutational frequency of the mtDNA and/or genomic DNA in the control and treated groups is determined.

Since mtDNA is thought to be 10–100 times more sensitive than genomic DNA to mutagenesis (Bianchi et al., *Mutat. Res.,* 488:9–23, 2001; Gattermann, *Leuk. Res,* 24:141–151, 2000; Golden and Melov, *Mech. Ageing Dev.,* 122:1577–1589, 2001; Gerhard et al., *Mech. Ageing Dev.,* 123:155–166, 2002; Battye et al., *J. Immunol. Methods,* 243:25–32, 2000), measuring the mutational frequency of mtDNA in the presence or absence of various agents is a sensitive method by which to identify agents that are potentially mutagenic to genomic DNA.

Specific aspects of the invention are illustrated by the following non-limiting Examples.

EXAMPLE 1

Bulk Genotype of the mtDNA Control Region

This example provides a description of a commonly employed method of identifying the genotype of mtDNA in a subject (bulk genotype) by sequencing total bone marrow cells obtained from the subject.

Bone marrow and peripheral blood specimens were collected from normal donors. Mononuclear cells from bone marrow and peripheral blood were separated by density gradient centrifugation and washed twice in phosphate buffered saline. DNA was extracted using QIAamp DNA blood mini kit (Qiagen, Valencia, Calif.). Extracted DNA was resuspended in TE buffer (pH 7.5) containing 10 mM Tris and 1 mM EDTA.

In order to directly sequence the control region of mtDNA, where the incidence of somatic mutations per nucleotide is approximately 10-fold higher than anywhere else in the mtDNA genome, the DNA extracted from total bone marrow cells was subjected to nested gene PCR amplification using the following nested primers: outer primer pair 5'-CGCCTACACAATTCTCCGATC-3' (SEQ ID NO: 1) and 5'-ACTTGGGTTAATCGTGTGACC-3' (SEQ ID NO: 2), which amplify the region between nucleotide 15,974 and nucleotide 921 of the human mtDNA genome, and inner primer pair 5'-TTAACTCCACCATTAG-CACC-3' (SEQ ID NO: 3) and 5'-GAAAGGCTAGGAC-CAAACCTA-3' (SEQ ID NO: 4), which amplify the region between nucleotide 15,971 and nucleotide 670 of the human mtDNA genome. Sequencing was performed on an ABI Prism 3100 Genetic Analyzer in both orientations.

There was a marked variation in the number of nucleotide changes among individual normal donors, with a range of 5 (donor 1) to 24 (donor 4) (11.7±6.6, mean±SD) nucleotide changes per donor (Table 2).

TABLE 2

Nucleotide sequence changes of mtDNA control region from total bone marrow cells.

| Donor (Age/Sex) | Polymorphism (Mutation) | Affected mtDNA gene |
|---|---|---|
| 1 (47/F) | C150T | HV2 + 7S + OH |
| | A263G | HV2 + OH |
| | 8C/6C* | HV2 + OH + CSB2 |
| | C16,192T | HV1 + 7S |
| | C16,270T | HV1 + 7S |
| 2 (38/F) | A73G | HV1 + 7S |
| | G185A | HV2 + 7S + OH |
| | A263G | HV2 + OH |
| | 7C/6C* | HV2 + OH + CSB2 |
| | (A478G) | |
| | T16,093C | HV1 |
| | A16,158G | HV1 + TAS |
| | T16,172C | HV1 + TAS |

TABLE 2-continued

Nucleotide sequence changes of mtDNA control region from total bone marrow cells.

| Donor (Age/Sex) | Polymorphism (Mutation) | Affected mtDNA gene |
|---|---|---|
| | A16,183C | HV1 + 7S |
| | T16,189C | HV1 + 7S |
| | A16,219G | HV1 + 7S |
| | C16,278T | HV1 + 7S |
| 3 (43/M) | A73G | HV1 + 7S |
| | T146C | HV2 + 7S + OH |
| | T152C | HV2 + 7S + OH |
| | T195C | HV2 + OH |
| | A263C | HV2 + OH |
| | 9C/6C | HV2 + OH + CSB2 |
| | del 514 C | |
| | del 515 A | |
| | C16,223T | HV1 + 7S |
| | C16,278T | HV1 + 7S |
| | C16,294T | HV1 + 7S |
| | G16,390A | 7S |
| 4 (34/M) | A93G | HV2 + 7S |
| | A95C | HV2 + 7S |
| | G185A | HV2 + 7S + OH |
| | A189G | HV2 + 7S + OH |
| | T236C | HV2 + OH |
| | 8C/6C | HV2 + OH + CSB2 |
| | G247A | HV2 + TFB1 |
| | A263G | HV2 + OH |
| | del C 514 | |
| | del A 515 | |
| | T16,093C | HV1 |
| | G16,129A | HV1 + 7S |
| | C16,148T | HV1 + 7S |
| | C16,168T | HV1 + 7S + TAS |
| | T16,172C | HV1 + 7S + TAS |
| | C16,187T | HV1 + 7S |
| | C16,188G | HV1 + 7S |
| | T16,189C | HV1 + 7S |
| | C16,223T | HV1 + 7S |
| | A16,230G | HV1 + 7S |
| | C16,278T | HV1 + 7S |
| | A16,293G | HV1 + 7S |
| | T16,311C | HV1 + 7S |
| | C16,320T | HV1 + 7S |
| 5 (54/M) | A73G | HV2 + 7S |
| | A263G | HV2 + OH |
| | 7C/6C | HV2 + OH + CSB2 |
| | del 514C | |
| | del 515A | |
| | T16,126C | HV1 + 7S |
| | C16,294T | HV1 + 7S |
| | C16,296T | HV1 + 7S |
| | T16,519C | 7S |
| 6 (34/F) | A73G | HV2 + 7S |
| | C150T | HV2 + 7S + OH |
| | A263G | HV2 + OH |
| | 8C/6C | HV2 + OH + CSB2 |
| | (A517G) | |
| | C16,270T | HV1 + 7S |
| | C16,292T | HV1 + 7S |
| | T16,362C | HV1 + 7S |

For example, when a sample containing total bone marrow cells from donor 1 was analyzed, six mtDNA polymorphisms were found (C150T, A263G, 8C/6C at nucleotide position 303 and 311, C16,192T and C16,270T). When a sample containing total bone marrow cells from donor 2 was analyzed, 11 such polymorphisms were identified (A73G, G185A, A263G, 6C at nucleotide position 311 of the mtDNA genome, T16,093C, A16,158G, T16,172C, A16, 183C, T16,189C, A16,219G and C16,278T), in addition to an apparently new mutation (A478G).

A total of 70 mtDNA-sequence variants were found in bulk bone marrow cells from six normal donors. Among these variants, 68 variants were previously listed in the Emory University online mtDNA polymorphism database and are thus considered polymorphisms. These results were compatible with data on bulk analysis of normal marrow specimens (Shin et al. *Blood*, prepublished online Nov. 21, 2002; DOI 10.1182/blood-2002-06-1825). Two of the nucleotide variants were new and were thus classified as mutations (A478G and A517G in donors 1 and 6, respectively).

EXAMPLE 2

Unexpected MtDNA Heterogeneity in Single CD34$^+$ Cell Clones from Normal Bone Marrow This example provides a description of one embodiment in which the mutational frequency in mtDNA is measured in clonal populations of CD34$^+$ cells obtained from bone marrow.

Abnormalities of mtDNA have been hypothesized to play important roles in senescence, malignancy and autoimmune disease. mtDNA mutations have also been implicated in myelodysplasia. However, in the previous studies, numerous point mutations were found in bulk samples of bone marrow cells from normal controls, as well as in patients.

To determine the heterogeneity of mtDNA sequences in normal bone marrow, bone marrow specimens were collected from six normal (do not have any apparent hematologic disease or symptom) donors. Alternatively, peripheral blood samples are collected from the donors either instead of, or in addition to, the bone marrow samples. Mononuclear cells were separated from other hematopoietic cells by standard Ficoll separation and washed twice in phosphate-buffered saline (PBS). Cells suspended in PBS were adjusted to 2×10$^7$ cells/ml. To each 12×75 mm tube containing 100 μl of the cell suspension, 10 μl of phycoerythrin (PE)-conjugated anti-CD34, or 10 μl of PE-conjugated IgG1 (BD Bioscience, Franklin Lakes, N.J.) were added. Following a 30 minute incubation at 4° C., cells were washed using cold PBS and resuspended in 0.5 ml PBS.

Human CD34$^+$ cells were sorted using a MoFlo cytometer (Dako-Cytomation, Fort Collins, Colo.) and an I-90 argon laser (emitting at 488 nm, Coherent Inc., Palo Alto, Calif.) for excitation. Forward scatter was used as the triggering parameter. PE fluorescence was detected using a 580/30 bandpass filter. Single cell deposition was performed using a CyClone automated cloner (Dako-Cytomation) in the 0.5 single drop mode. Gating of the cells was based on forward scatter and PE fluorescence. Individual CD34$^+$ cells were plated into each well of a 96-well culture plate with 100 μl of serum-free medium containing 100 ng/ml of stem cell factor (SCF), 100 ng/ml of Flt-3, 100 ng/ml of thrombopoietin (TPO), in the presence or absence of 50 ng/ml of granulocyte-colony stimulating factor (G-CSF).

After five days of culture, each well of the microtiter plate was carefully examined with an inverted microscope (Olympus IX50; Melville, N.Y.) in order to examine growth and plating efficiency of single CD34$^+$ cells. Cells in each well were graded based on the number of cells present in the well following the five-day culture. Grade 1 represented five or fewer cells per well; Grade 2, between six and ten cells per well; Grade 3, between 11 and 20 cells per well; and Grade 4, more than 21 cells per well. Cloning (plating) efficiency was defined as the number of positive wells (any cells present)÷total wells×100. Although there was some variation of plating efficiency of CD34$^+$ cells among six normal donors, overall average efficiency was 30% (30±11.7, mean±SD) (Table 3). Plating efficiency was not affected by G-CSF in the growing medium, however colony size was increased in the presence of G-CSF.

TABLE 3

The number and distribution of CD34$^+$ clones from bone marrow after 5 day culture.

| Donor Grade\ | 1 | | 2 | | 3 | | 4 | | 5 | | 6 | | Subtotal No. | | |
|---|---|---|---|---|---|---|---|---|---|---|---|---|---|---|---|
| G-CSF | + | − | + | − | + | − | + | − | + | − | + | − | + | − | Total No. |
| 1 | 14 | 19 | 27 | 22 | 103 | 176 | 45 | 71 | 98 | 208 | 82 | 131 | 369 | 627 | 996 |
| 2 | 9 | 12 | 1 | 2 | 65 | 84 | 33 | 74 | 67 | 110 | 43 | 103 | 218 | 385 | 603 |
| 3 | 16 | 14 | 1 | 3 | 49 | 42 | 50 | 53 | 60 | 59 | 79 | 70 | 255 | 241 | 496 |
| 4 | 36 | 2 | 6 | 0 | 122 | 5 | 112 | 21 | 135 | 5 | 150 | 16 | 561 | 49 | 610 |
| Total clone No. | 75 | 47 | 35 | 27 | 339 | 307 | 240 | 219 | 360 | 382 | 354 | 320 | 1403 | 1302 | 2705 |
| Microplate No.* | 2 | 2 | 5 | 5 | 10 | 10 | 10 | 10 | 10 | 10 | 10 | 10 | 47 | 47 | 94 |
| Plating Efficiency (%) | 39.1 | 24.5 | 7.3 | 5.6 | 35.3 | 32.0 | 25.0 | 22.8 | 37.5 | 39.8 | 36.9 | 33.3 | 31.1 | 28.9 | 30.0 |

Culture medium with (+) or without (−) G-CSF.

*the number of 96-well plates used for culture.

Figure 3:
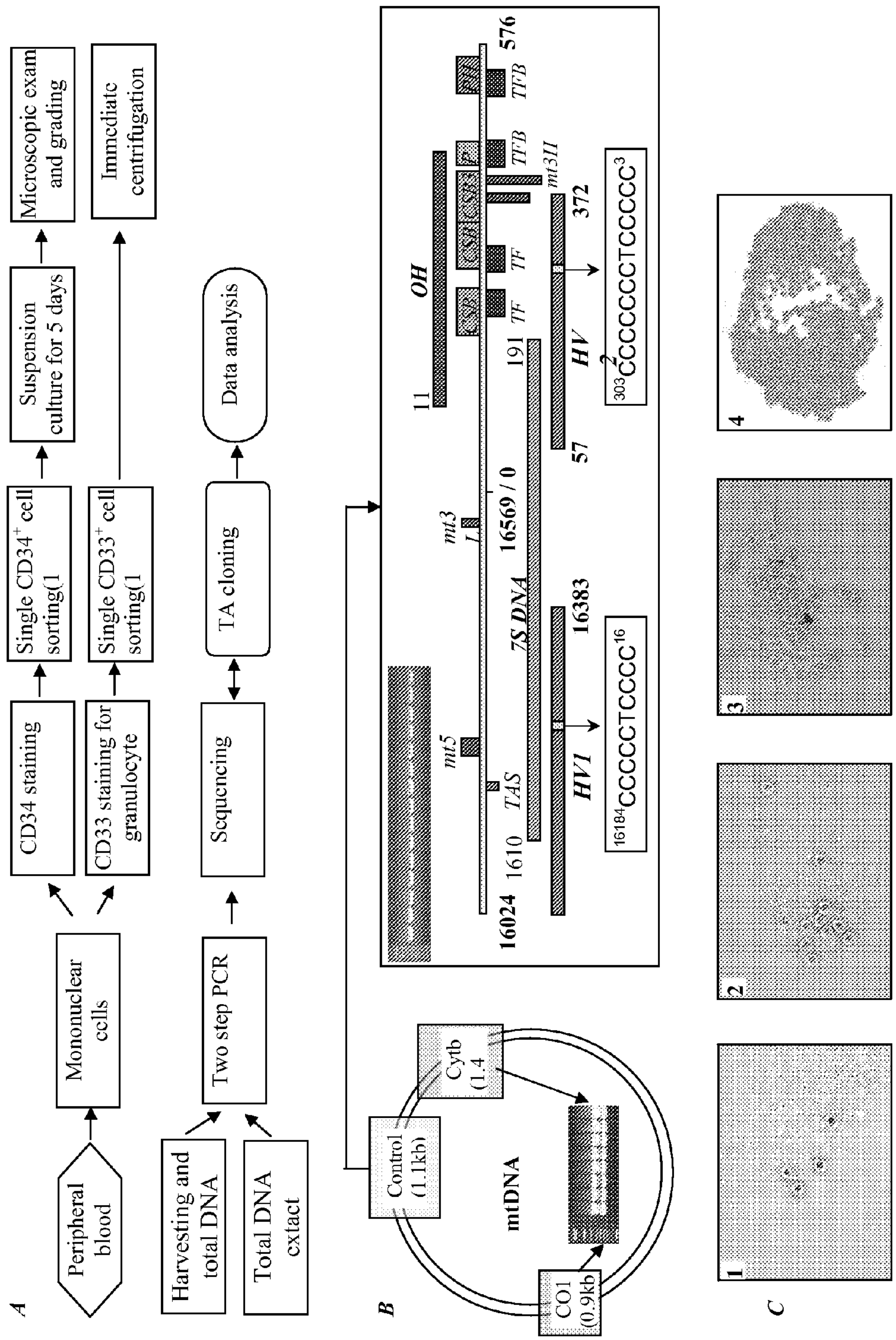
FIG. 3 is a series of drawings and digital images.

To assess heterogeneity of the mtDNA sequences among $CD34^+$ cells from normal donors, the 1,121 base pair mtDNA control region (a region known to contain multiple mutational hotspots, nucleotide position 16024 through nucleotide position 576 as shown in FIG. 1 and FIG. 3) in a set of 611 $CD34^+$ clones (clonal populations) from the normal donors was subjected to sequencing analysis (Table 4).

TABLE 4

The number of $CD34^+$ clones from bone marrow subjected to mtDNA sequencing analysis.

| Donor Grade\ | 1 | | 2 | | 3 | | 4 | | 5 | | 6 | | Total |
|---|---|---|---|---|---|---|---|---|---|---|---|---|---|
| G-CSF | + | − | + | − | + | − | + | − | + | − | + | − | No. |
| 1 | 14 | 14 | 13 | 10 | 15 | 15 | 13 | 13 | 12 | 14 | 14 | 11 | 158 |
| 2 | 8 | 12 | 1 | 2 | 15 | 15 | 14 | 14 | 15 | 13 | 15 | 15 | 139 |
| 3 | 16 | 14 | 1 | 3 | 15 | 15 | 15 | 13 | 15 | 15 | 15 | 15 | 152 |
| 4 | 35 | 2 | 6 | 0 | 25 | 5 | 15 | 14 | 25 | 5 | 15 | 15 | 162 |
| Subtotal | 73 | 42 | 21 | 15 | 70 | 50 | 57 | 54 | 67 | 47 | 59 | 56 | 611 |
| No. Total No. | 115 | | 36 | | 120 | | 111 | | 114 | | 115 | | |

To prepare for sequencing analysis, each $CD34^+$ clone was harvested from the culture well into a 1.5 ml microcentrifuge tube by vigorous pipetting and dispensing, followed by a rinse of the well with 200 μl PBS. Cells were collected after centrifugation at 300×g for 5 minutes, and then washed with PBS. Cell pellets were stored at −80° C. In order to extract DNA from individual $CD34^+$ clones, each cell pellet was covered with 30 μl of 1×TE buffer and lysed by incubating the cells at 95° C. for 10 minutes, with occasional shaking. The lysate was briefly microfuged and stored at −20° C.

In order to directly sequence the control region of mtDNA, where the incidence of somatic mutations per nucleotide is approximately 10-fold higher than anywhere else in the mtDNA genome (Coller et al., *Ann. N.Y. Acad. Sci.* 959:434-447, 2002), DNA in the clonal populations was subjected to nested gene PCR amplification using the following nested primers: outer primer pair 5'-CGCCTACACAATTCTCCGATC-3' (SEQ ID NO: 1) and 5'-ACTTGGGTTAATCGTGTGACC-3' (SEQ ID NO: 2), which amplify the region between nucleotide 15,974 and nucleotide 921 of the human mtDNA genome as represented by the revised Human mtDNA Cambridge Reference sequence (Andrews et al., *Nat. Genet.* 23:147, 1999; Kogelnik et al., *Nucleic Acids Res.* 26:112, 1998), and inner primer pair 5'-TTAACTCCACCATTAGCACC-3' (SEQ ID NO: 3) and 5'-GAAAGGCTAGGACCAAACCTA-3' (SEQ ID NO: 4), which amplify the region between nucleotide 15,971 and nucleotide 670 of the human mtDNA genome as represented by the revised Human mtDNA Cambridge Reference sequence (Andrews et al., *Nat. Genet.* 23:147, 1999; Kogelnik et al., *Nucleic Acids Res.* 26:112, 1998). Amplification of mtDNA was performed with the TaKaRa LA PCR kit (PanVera, Madison, Wis.).

The primary PCR mixture contained 400 μM of each dNTP, 2 units of TaKaRa LA Taq™ (Pan Vera, Madison, Wis.), 0.8 μM outer primers and 2 μl of cell lysate in a total volume of 30 μl. PCR amplification was carried out in a thin-wall 0.5 ml PCR tube using the DNA thermal cycler 480 (Perkin-Elmer, Foster City, Calif.): one cycle at 96° C. for 1 minute; 35 cycles at 94° C. for 30 seconds, 52° C. for 50 seconds and 72° C. for 1 minute with a 5-second increase per cycle; one cycle of 72° C. for 5 minutes. The secondary PCR was performed in 50 μl of reaction mixture containing 400 μM of each dNTP, 2 units of TaKaRa LA Taq™ (PanVera, Madison, Wis.), 0.8 μM inner nested primers and 1 μl of primary PCR product under the same amplification procedure as described above. Secondary PCR samples were electrophoresed on 1% agarose gels and stained with ethidium bromide to assess the purity and size of DNA fragments, and subsequently purified using the QIAquick™ PCR purification kit (Qiagen, Valencia, Calif.). As negative controls, reaction mixtures without DNA templates were subjected to PCR amplification. These samples were consistently negative for PCR product. To prevent DNA cross-contamination, special precautions were taken for each procedure of cell harvest, DNA extraction, PCR amplification and DNA sequencing.

The purified-PCR products were subjected to cycle sequencing with the appropriate primers using the BigDye Terminator v3.0 Ready Reaction kit (Applied Biosystems, Foster City, Calif.) according to the manufacturer's protocol, and then applied to the ABI Prism 3100 Genetic Analyzer (Applied Biosystems). The following oligonucleotide primers were used for sequencing:

5'CAGTGTATTGCTTTGAGGAGG3' (SEQ ID NO: 5),

5'CATCTGGTTCCTACTTCAGGGTC3' (SEQ ID NO: 6),

5'TTAACTCCACCATTAGCACC3' (SEQ ID NO: 7),

5'GCATGGAGAGCTCCCGTGAGTGG3' (SEQ ID NO: 8),

5'CACCCTATTAACCACTCACG3' (SEQ ID NO: 9) and

5'TACATTACTGCCAGCCACCATG3' (SEQ ID NO: 10).

The mtDNA sequences experimentally obtained were compared to the 2001 Revised Cambridge Reference Sequence (Andrews et al., *Nat. Genet.* 23:147, 1999; Kogelnik et al., *Nucleic Acids Res.* 26:112, 1998) using the National Center for Biotechnology Information (NCBI) Blast2 program and the database search tool, MitoAnalyzer (National Institute of Standards and Technology, Gaithersburg, Md.), in order to identify polymorphisms and mutations. All automated results were manually confirmed. To exclude potential artifacts, PCR amplifications from original cell lysates were additionally replicated one or two more times: when nucleotide changes were reproduced in all independent PCR amplifications, they were considered to be confirmed.

To confirm the mtDNA control region sequence, PCR products were directly inserted into pCR®2.1-TOPO® vector and transformed into competent *E. coli* (TOP10 cells) using the TOPO TA™ cloning kit (Invitrogen, Carlsbad, Calif.). Recombinant plasmids isolated from 8 to 12 white colonies were subjected to sequencing.

Analysis of the set of 611 $CD34^+$ clones (clonal populations) from six normal donors revealed that a total of 138 clones (22.6%±13.6%) of the total assayed clones (611 clones) displayed mtDNA heterogeneity distinct from the donor's corresponding bulk mtDNA sequences and 47.8% (66/138 clones) of the heterogeneity was localized to a mutational hot spot in the poly C tract between nucleotides 303-315 (Table 5).

TABLE 5

Summary of mtDNA heterogeneity among single CD34+ clones from b ne marr w

| Donor/Heteroplasmy pattern | mtDNA gene | No. Clone | No. Total | % |
|---|---|---|---|---|
| 1 BM poly alone | | 85 | 85 | 73.9 |
| +8C/6C* +9C/6C | HV2, OH, CSB2 | 22 | 30 | 26.1 |
| +9C/6C* | HV2, OH, CSB2 | 2 | | |
| +7C/6C* | HV2, OH, CSB2 | 1 | | |
| +A189G/A | HV2, OH, 7S | 1 | | |
| +T204C | HV2, OH | 1 | | |
| +C277T | HV2, OH, TFB1 | 1 | | |
| +C514CAC | | 1 | | |
| +C16,114T | HV1, 7S | 1 | | |
| Subtotal | | 115 | 115 | 100.0 |
| 2 BM poly alone | | 33 | 33 | 91.7 |
| +T16,131C/T | HV1, 7S | 1 | 3 | 8.3 |
| +G16,145A | HV1, 7S | 1 | | |
| A191AA | HV2, OH, 7S | 1 | | |
| C194T | HV2, OH | | | |
| T199C | HV2, OH | | | |
| G207A | HV2, OH | | | |
| A73G, 8C/6C* | HV2, OH, CSB2 | | | |
| A263G T489C | | | | |
| C16,147T | HV1, 7S | | | |
| C16,173T | HV1, 7S | | | |
| C16,245T | HV1, 7S | | | |
| T16,362C | HV1, 7S | | | |
| Subtotal | | 36 | 36 | 100.0 |
| 3 BM poly alone | | 96 | 96 | 80.0 |
| +9C/6C* +10C/6C* | HV2, OH, CSB2 | 11 | 24 | 20.0 |
| +8C/6C* +9C/6C* | HV2, OH, CSB2 | 6 | | |
| +8C/6C* | HV2, OH, CSB2 | 2 | | |
| +C182T/C | HV2, OH, 7S | 2 | | |
| 8C/6C* +9C/6C* | HV2, OH, CSB2 | | | |
| +del 71G | HV2, 7S | 1 | | |
| +9C/6C* +10C/6C* | HV2, OH, CSB2 | | | |
| +T279C/T | HV2, OH, TFB1 | 1 | | |
| +G16,153A | HV1, 7S | 1 | | |
| Subtotal | | 120 | 120 | 100.0 |
| 4 BM poly alone | | 95 | 95 | 85.6 |
| +8C/6C* +9C/6C* | HV2, OH, CSB2 | 11 | 16 | 14.4 |
| +7C/6C* +8C/6C* | HV2, OH, CSB2 | 2 | | |
| +9C/6C* +10C/6C* | HV2, OH, CSB2 | 1 | | |
| +T89C | HV2, 7S | 1 | | |
| +8C/6C* +9C/6C* | HV2, OH, CSB2 | 1 | | |
| 16,093T | HV1 | | | |
| Subtotal | | 111 | 111 | 100.0 |
| 5 BM poly alone | | 62 | 62 | 54.4 |
| +514C, 515A | | 19 | 52 | 45.6 |
| +C264T | HV2, OH | 18 | | |
| +C264T/C | HV2, OH | 3 | | |
| +7C/6C* +8C/6C* | HV2, OH, CSB2 | 2 | | |
| +T146C | HV2, OH, 7S | 2 | | |
| 514C, 515A | | | | |
| +T146C | HV2, OH, 7S | 1 | | |
| C264T/C | HV2, OH | | | |
| +T146C/T | HV2, OH, 7S | 1 | | |
| 514C, 515A | | | | |
| +T146C | HV2, OH, 7S | 1 | | |
| +A189G | HV2, OH, 7S | 1 | | |
| +C264T/C | HV2, OH | 1 | | |
| 514C, 515A | | | | |
| +T161C/T | HV2, OH, 7S | 1 | | |
| C264T | HV2, OH | | | |
| 514C, 515A | | | | |
| +T16,189C | HV1, 7S | 1 | | |
| +C16,296C/T | HV1 | 1 | | |
| Subtotal | | 114 | 114 | 100.0 |
| 6 BM poly alone | | 102 | 102 | 88.7 |
| +8C/6C* +9C/6C* | HV2, OH, CSB2 | 5 | 13 | 11.3 |
| +A200G/A | HV2, OH | 3 | | |

TABLE 5-continued

Summary of mtDNA heterogeneity among single CD34+ clones from b ne marr w

| Donor/Heteroplasmy pattern | mtDNA gene | No. Clone | No. Total | % |
|---|---|---|---|---|
| +A200G | HV2, OH | 2 | | |
| +A200G/A | HV2, OH | 1 | | |
| +7C/6C* +8C/6C* | HV2, OH, CSB2 | | | |
| +A200G/A | HV2, OH | 1 | | |
| +8C/6C* +9C/6C* | HV2, OH, CSB2 | | | |
| +7C/6C* +8C/6C* | HV2, OH, CSB2 | 1 | | |
| Subtotal | | 115 | 115 | 100.0 |
| No and % of CD34+ clones having 'the same as total BM polymorphism alone' (77.4 ± 13.6%, mean ± SD) | | | 473 | 77.4 |
| No and % of CD34+ clones showing 'mtDNA heterogeneity' (22.6 ± 13.6%, mean ± SD) | | | 138 | 22.6 |
| Total No of assayed CD34+ clones | | | 611 | 100.0 |

Abbreviations and symbols used in Table 5 include: BM poly, mtDNA polymorphism from total bone marrow cells; +, mtDNA nucleotide changes in addition to the polymorphisms detected in the respective bulk mtDNA; *, poly C tract localized between nucleotide 303 and 315.

Figure 2:
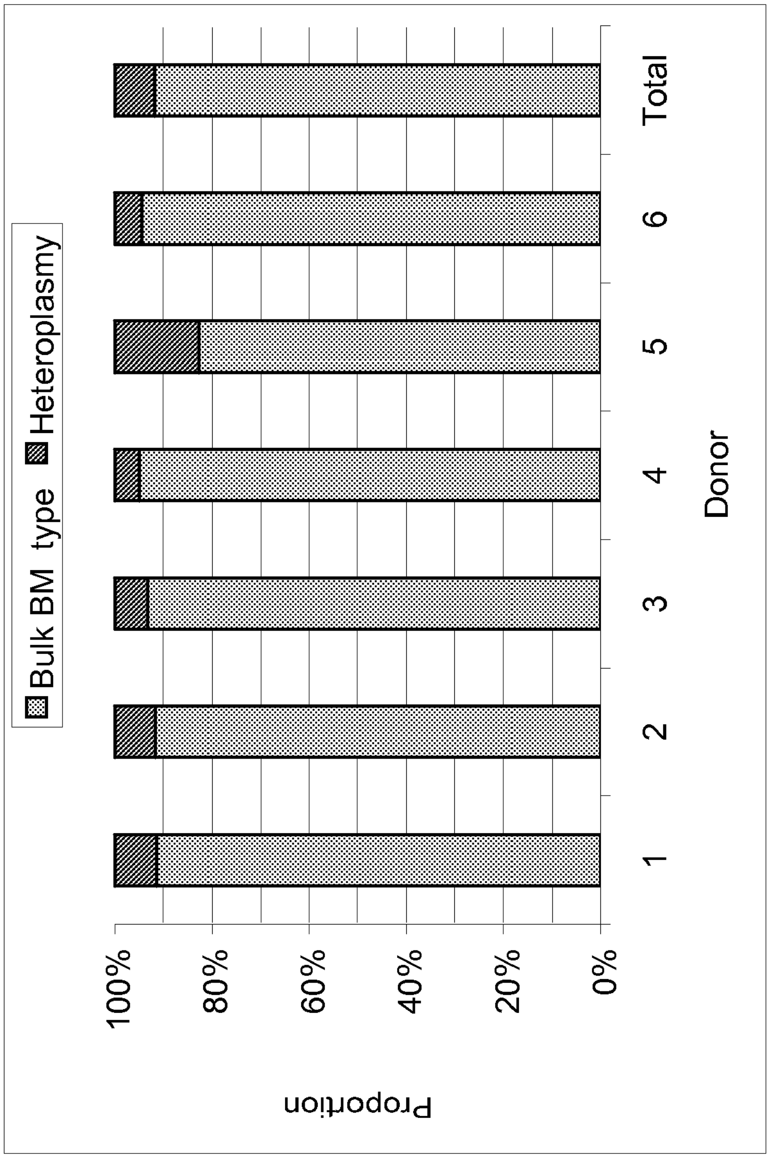
FIG. 2 is a graph showing the proportion of mtDNA showing heteroplasmic patterns in various donors. The proportion of heterogenous mtDNA in $CD34^+$ clones was 8.6% (n=8), 8.3% (n=3), 6.8% (n=7), 5.0% (n=5), 17.3% (n=13) and 5.6% (n=6) in donors 1 through 6, respectively (8.6±4.5, mean±SD).

Common patterns of mtDNA heterogeneity in the CD34+ clonal populations among the set of CD34+ clonal populations from the six donors included one or two nucleotide changes (for instance substitution, insertion or deletion), in addition to the polymorphisms detected in the respective bulk mtDNA. Among the nucleotide changes identified in the corresponding regions of mtDNA, most were due to single nucleotide substitutions at various positions and length alterations in the homopolymeric C tract located between nucleotide position 303 and 315 of the mtDNA sequence. The mtDNA heterogeneity of CD34+ clones in six donors was classified into several patterns according to nucleotide changes: 8, 3, 7, 5, 13 and 6 patterns in donor 1 to 6, respectively. The mean proportion of heterogenous pattern of mtDNA heterogeneity among single CD34+ clones was 8.6% (8.6±4.5, mean±SD) (FIG. 2). These results were unexpected, as rapidly dividing tissues such as bone marrow have not been thought to permit the homoplasmic resolution of mtDNA mutations over time. Specifically, donors 1 and 3 showed clones with homopolymeric C tract length heteroplasmy (nucleotide 303–nucleotide 315). In donor 5, nucleotide changes at nucleotide positions 264, 514, and 515 were common. Donor 5 also showed heteroplasmy of substituted nucleotides at four nucleotide positions (T146C/T, T161 C/T, C264T/C, and C16296T/C).

The mtDNA sequence of a single CD34+ clonal population from donor 2 exhibited a pattern (A73G, A191AA, C194T, T199C, G207A, 8C/6C at nucleotide 303 and 311, T489C, C16,147T, C16,173T, C16,245T, T16,362C) that was distinct from bulk bone marrow mtDNA, as well as from other CD34+ clonal populations from the same donor. Overall, the pattern of mtDNA heterogeneity was remarkably different among the six donors. Neither the presence of G-CSF in the growing medium, nor the colony size was statistically correlated with the proportion of CD34+ clones with variant mtDNA (Table 6).

TABLE 6

Distribution of mtDNA heterogeneity according to each grade and culture media

| Grade | 1 | | 2 | | 3 | | 4 | | Subtotal No. | | |
|---|---|---|---|---|---|---|---|---|---|---|---|
| Donor\G-CSF | + | − | + | − | + | − | + | − | + | − | Total No. |
| 1 | 3 | 3 | 1 | 1 | 5 | 7 | 10 | 0 | 19 | 11 | 30 |
| 2 | 2 | 0 | 1 | 0 | 0 | 0 | 0 | 0 | 3 | 0 | 3 |
| 3 | 2 | 3 | 3 | 3 | 3 | 4 | 5 | 1 | 13 | 11 | 24 |
| 4 | 1 | 1 | 1 | 3 | 4 | 2 | 0 | 4 | 6 | 10 | 16 |
| 5 | 6 | 6 | 6 | 6 | 10 | 7 | 10 | 1 | 32 | 20 | 52 |
| 6 | 0 | 1 | 3 | 5 | 2 | 0 | 1 | 1 | 6 | 7 | 13 |
| Subtotal No. | 14 | 14 | 15 | 18 | 24 | 20 | 26 | 7 | 79 | 59 | 138 |
| Assayed colony No. | 81 | 77 | 68 | 71 | 77 | 75 | 121 | 41 | 347 | 264 | 611 |
| Proportion (%)* | 17.3 | 18.2 | 22.1 | 25.4 | 31.2 | 26.7 | 21.5 | 17.1 | 22.8 | 22.3 | 22.6 |

*No statistical significant difference between culture media with G-CSF, those without G-CSF and each grade A high incidence of nucleotide variations was observed in both HV2 (44/62, 71%) and HV1 (11/62, 18%) segments. Thus, most heteroplasmic mutations were found in HV2, which includes mutations within the homopolymeric C tract. This narrow region of the homopolymeric C tract was a "hot spot" for heteroplasmic events in isolated CD34$^+$ cells, where 69% (18/44) and 29% (18/62) of the heteroplasmic mutations were present in the hypervariable regions and in the mtDNA control region, respectively. The results indicate that in vivo clonal expansion of mtDNA is a general and common process in hematopoietic tissue.

The general mechanism for the clonal expansion of mtDNA mutations in hematopoietic stem cells is believed to include random segregation or random genetic drift via unbiased mtDNA replication and sorting during cell divisions. Based on these theories, the pattern of length heteroplasmy (the relative proportion of length variants) in poly (C) tracts could show a different pattern in sister cells. However, studies have indicated that the pattern of length heteroplasmy in poly C tracts is actively maintained in daughter cells.

The data presented above indicate that several homopolymeric tracts in the mtDNA exhibit length polymorphisms (the presence in cells of multiple mtDNA species with various lengths of a homonucleotide run). For example, a mtDNA variant (T16,189C) introduces a cytosine, thereby generating an unstable homopolymeric tract of ten cytosines between nucleotide positions 16,184 and 16,193. Some studies have indicated that the pattern of the length heteroplasmy associated with the T16,189C mutation is maternally inherited in that the pattern of length heteroplasmy co-segregates among maternally related members. In addition, recent evidence demonstrates the de novo regeneration of the pattern of length heteroplasmy associated with the T16,189C variant (Malik et al., *J. Hum. Genet.,* 47:122–130, 2002).

EXAMPLE 3

MtDNA Heterogeneity in Single CD34$^+$ Cell Clones from Normal Umbilical Cord Blood This example provides a description of one embodiment in which the mutational frequency in mtDNA is measured in clonal populations of CD34$^+$ cells.

To determine the heterogeneity of mtDNA sequences in CD34$^+$ cells from umbilical cord blood, normal umbilical cord blood was collected from five normal (do not have any apparent hematologic disease or symptom) donors. Alternatively, peripheral blood, or bone marrow samples are collected from the donors either instead of, or in addition to, the umbilical cord blood samples.

DNA extracted from total umbilical cord blood cells was subjected to nested gene PCR amplification as described in Example 1, above. Sequencing was performed on an ABI Prism 3100 Genetic Analyzer in both orientations. Nucleotide sequence changes of the mtDNA control region in bulk samples of umbilical cord blood are listed in Table 7.

The mtDNA sequence changes from bulk umbilical cord blood showed individual variations but, interestingly, three (cord blood donors 2, 3, and 5) of the five cord blood donors had length variations of the poly (C) tract at nucleotide positions 303–315 and 16,183–16, 193 (Table 7). These findings were not observed in bulk genotype from adult total bone marrow cells.

TABLE 7

Nucleotide sequence changes of mtDNA control region from total umbilical cord blood.

| Donor (Age/Sex) | Polymorphism (Mutation) | Affected mtDNA gene |
|---|---|---|
| 1 | A73G | HV2, 7S |
| | T146C | HV2, 7S, OH |
| | T195A | HV2, OH |
| | A263G | HV2, OH |
| | 7C/6C | HV2, OH, CSB2 |
| | T489C | |
| | del CA 514-5 | |
| | A16,166T | |
| | (del C 16169) | HV1, 7S, TAS |
| | T16,172C | HV1, 7S, TAS |
| | C16,223T | HV1, 7S |
| | C16,354T | HV1, CSB3 |
| | T16,519C | 7S |
| 2* | T72C | HV2, 7S |
| | C253T | HV2, OH, TFB1 |
| | A263G | HV2, OH |
| | 9C/6C | HV2, OH, CSB2 |
| | 10C/6C | |
| | 8C/6C | |
| | C16,256T | HV1, 7S |
| 3* | T16,298C | HV1, 7S |
| | T16,519C | 7S |
| | A73G | HV2, 7S |
| | T146C | HV2, 7S, OH |
| | A189G | HV2, 7S, OH |
| | C194T | HV2, OH |

TABLE 7-continued

Nucleotide sequence changes of mtDNA control region from total umbilical cord blood.

| Donor (Age/Sex) | Polymorphism (Mutation) | Affected mtDNA gene |
|---|---|---|
| | T195C | HV2, OH |
| | T204C | HV2, OH |
| | G207A | HV2, OH |
| | A263G | HV2, OH |
| | T279C | HV2, OH |
| | 8C/6C | HV2, OH, CSB2 |
| | 9C/6C | |
| | C16,223T | HV1, 7S |
| | C16,292T | HV1, 7S |
| | T16,519C | 7S |
| 4 | A73G | HV2, 7S |
| | del 249A | HV2, OH, TFB1 |
| | del 290,291AA | HV2, OH, TFB2 |
| | 7C/6C | HV2, OH, CSB2 |
| | T489C | |
| | A493G | |
| | del 514,515CA | |
| | C16,223T | HV1, 7S |
| | T16,298C | HV1, 7S |
| | T16,325C | HV1, 7S |
| | C16,327T | HV1, 7S |
| | T16,519C | 7S |
| 5* | A73G | HV2, 7S |
| | C150T | HV2, 7S, OH |
| | T195C | HV2, OH |
| | A263C | HV2, OH |
| | 7C/6C | HV2, OH, CSB2 |
| | A16,171G | HV1, 7S, TAS |
| | T16,172C | HV1, 7S, TAS |
| | T16,189C | HV1, 7S |
| | C16,193C/CC | HV1, 7S |
| | C16,223T | HV1, 7S |
| | C16,320T | HV1, 7S |
| | T16,519C | 7S |

*Mixed nucleotide signal (mixed peak on sequencing chromatogram) at nucleotide position between 303 and 315; #, np 16,183–16193

In order to determine the heterogeneity of single CD34$^+$ clones from umbilical cord blood, mononuclear cells were separated from other hematopoietic cells by standard Ficoll separation and washed twice in phosphate-buffered saline (PBS). Cells suspended in PBS were adjusted to 2×10$^7$ cells/ml. To each 12×75 mm tube containing 100 μl of the cell suspension, 10 μl of phycoerythrin (PE)-conjugated anti-CD34, or 10 μl of PE-conjugated IgG1 (BD Bioscience, Franklin Lakes, N.J.) were added. Following a 30 minute incubation at 4° C., cells were washed using cold PBS and resuspended in 0.5 ml PBS.

Human CD34$^+$ cells were sorted using a MoFlo cytometer (Dako-Cytomation, Fort Collins, Colo.) and an I-90 argon laser (emitting at 488 nm, Coherent Inc., Palo Alto, Calif.) for excitation. Forward scatter was used as the triggering parameter. PE fluorescence was detected using a 580/30 bandpass filter. Single cell deposition was performed using a CyClone automated cloner (Dako-Cytomation) in the 0.5 single drop mode. Gating of the cells was based on forward scatter and PE fluorescence. Individual CD34$^+$ cells were plated into each well of a 96-well culture plate with 100 μl of serum-free medium containing 100 ng/ml of stem cell factor (SCF), 100 ng/ml of Flt-3, 100 ng/ml of thrombopoietin (TPO), in the presence or absence of 50 ng/ml of granulocyte-colony stimulating factor (G-CSF).

After five days of culture, each well of the microtiter plate was carefully examined with an inverted microscope (Olympus IX50; Melville, N.Y.) in order to examine growth and plating efficiency of single CD34$^+$ cells. As described above in Example 2, cells in each well were graded based on the number of cells present in the well following the five-day culture. Cloning (plating) efficiency was defined as the number of positive wells (any cells present)÷total wells× 100. Although there was some variation of plating efficiency of CD34$^+$ cells among five normal donors, overall average efficiency was 79% (78.6±11.7, mean±SD) (Table 8). Plating efficiency was not affected by G-CSF in the growing medium, however colony size was increased in the presence of G-CSF.

TABLE 8

The number and distribution of CD34$^+$ clones from umbilical cord blood after 5 day culture.

| Donor | 1 | | 2 | | 3 | | 4 | | Subtotal No | | Total | Microplate* | | PE (%) | |
|---|---|---|---|---|---|---|---|---|---|---|---|---|---|---|---|
| Grade/G-CSF | + | − | + | − | + | − | + | − | + | − | No | + | − | + | − |
| 1 | 46 | 85 | 79 | 155 | 167 | 309 | 398 | 124 | 690 | 673 | 1363 | 10 | 10 | 71.9 | 70.1 |
| 2 | 8 | 8 | 6 | 21 | 23 | 78 | 369 | 309 | 406 | 416 | 822 | 5 | 5 | 84.6 | 86.7 |
| 3 | 28 | 55 | 33 | 45 | 57 | 44 | 280 | 245 | 398 | 389 | 787 | 5 | 5 | 82.9 | 81.0 |
| 4 | 23 | 30 | 21 | 26 | 30 | 59 | 346 | 299 | 420 | 414 | 834 | 5 | 5 | 87.5 | 86.3 |
| 5 | 22 | 33 | 23 | 36 | 29 | 52 | 286 | 243 | 360 | 364 | 724 | 5 | 5 | 75.0 | 75.8 |
| Subtotal | 127 | 211 | 162 | 283 | 306 | 542 | 1679 | 1220 | 2274 | 2256 | 4530 | 30 | 30 | 79.0 | 78.3 |
| Total | 338 | | 445 | | 848 | | 2899 | | 4530 | | | 60 | | 78.6 | |

Culture medium with (+) or without (−) G-CSF.

*the number of 96-well plates used for culture.

To assess heterogeneity of the mtDNA sequences among CD34$^+$ cells from each of the normal umbilical cord blood donors, the 1,121 base pair mtDNA control region in a set of 580 CD34$^+$ clones (clonal populations) was subjected to sequencing analysis (Table 9).

TABLE 9

The number of CD34$^+$ clones from umbilical cord blood subjected to mtDNA sequencing analysis.

| Donor Grade/ | 1 | | 2 | | 3 | | 4 | | Subtotal No | | Total as- |
|---|---|---|---|---|---|---|---|---|---|---|---|
| G-CSF | + | − | + | − | + | − | + | − | + | − | sayed No |
| 1 | 15 | 15 | 14 | 15 | 15 | 15 | 15 | 15 | 59 | 60 | 119 |
| 2 | 8 | 8 | 6 | 15 | 15 | 16 | 26 | 26 | 55 | 65 | 120 |
| 3 | 14 | 13 | 14 | 15 | 15 | 15 | 5 | 13 | 48 | 56 | 104 |
| 4 | 15 | 14 | 15 | 15 | 15 | 15 | 15 | 15 | 60 | 59 | 119 |
| 5 | 14 | 15 | 15 | 14 | 15 | 15 | 15 | 15 | 59 | 59 | 118 |
| Subtotal | 66 | 65 | 64 | 74 | 75 | 76 | 76 | 84 | 281 | 299 | 580 |
| Total | 131 | | 138 | | 151 | | 160 | | 580 | | |

To prepare for sequencing analysis, each CD34$^+$ clone was harvested from the well into a 1.5 ml microcentrifuge tube by vigorous pipetting and dispensing followed by rinse of the well with 200 μl of PBS. Cells were collected after centrifugation at 300×g for 5 minutes, and then washed with PBS. Cell pellets were stored at −80° C. In order to extract DNA from individual CD34$^+$ clones, each cell pellet was covered with 30 μl of 1×TE buffer and lysed by incubating the cells at 95° C. for 10 minutes, with occasional shaking. The lysate was briefly microfuged and stored at −20° C.

DNA in the CD34$^+$ clonal populations of cells was amplified to directly sequence the mtDNA control region. Cell lysates of individual CD34$^+$ clones were subjected to amplification of mtDNA using the LA PCR kit (TaKaRa, Panvera, Madison, Wis.). Nested (two-step) PCR amplification was performed with outer and inner pairs of primers in order to generate sufficient template from CD34$^+$ clones for sequencing of the mtDNA control region. The outer pair of primers (5'-CGCCTACACAATTCTCCGATC-3' (SEQ ID NO: 1) and 5'-ACTTGGGTTAATCG TGTGACC-3' (SEQ ID NO: 2)) was used for amplification of the fragment between nucleotide 15974 and 921 of the revised Human mtDNA Cambridge Reference Sequence (Andrews et al., *Nat. Genet.* 23:147, 1999; Kogelnik et al., *Nucleic Acids Res.* 26:112, 1998). The inner nested pair of primers (5'-TTAACTCCACCATTAGCACC-3' (SEQ ID NO: 3) and 5'-GAAAGGCTAGGACCAAA CCTA-3' (SEQ ID NO: 4)) amplified the fragment between nucleotide 15,971 and 670 of the revised Human mtDNA Cambridge Reference Sequence (Andrews et al., *Nat. Genet.* 23:147, 1999; Kogelnik et al., *Nucleic Acids Res.* 26:112, 1998).

The primary PCR mixture contained 400 μM of each dNTP, 2 units of LA Taq™, 0.8 μM outer primers and 3 μl of cell lysate in a total volume of 30 μl. PCR amplification was carried out in a thin-wall 0.5 ml PCR tube using the DNA thermal cycler 480 (Perkin-Elmer, Foster City, Calif.): one cycle of 96° C. for 1 minute; 35 cycles of 94° C. for 30 seconds, 52° C. for 50 seconds and 72° C. for 1 minute with a 5-second increase per cycle; one cycle of 72° C. for 5 minutes. The secondary PCR was performed in 50 μl of reaction mixture containing 400 μM of each dNTP, 2 units of LA Taq™, 0.8 μM inner nested primers and 1 μl of primary PCR product under the same amplification procedure as described above. Secondary PCR samples were electrophoresed on 1% agarose gels and stained with ethidium bromide to assess the purity and size of DNA fragments, and subsequently purified using the QIA quick PCR purification kit (Qiagen, Valencia, Calif.). As negative controls, reaction mixtures without DNA templates were subjected to PCR amplification. These samples were consistently negative for PCR product. To prevent DNA cross-contamination, special precautions were taken for each procedure of cell harvest, DNA extraction, PCR amplification and DNA sequencing.

The purified-PCR products were subjected to cycle sequencing with the appropriate primers using the BigDye Terminator v3.0 Ready Reaction kit (Applied Biosystems, Foster City, Calif.) according to the manufacturer's protocol, and then applied to the ABI Prism 3100 Genetic Analyzer (Applied Biosystems). The following oligonucleotide primers were used for sequencing:

5'CAGTGTATTGCTTTGAGGAGG3' (SEQ ID NO: 5),

5'CATCTGGTTCCTACTTCAGGGTC3' (SEQ ID NO: 6),

5'TTAACTCCACCATTAGCACC3' (SEQ ID NO: 7),

5'GCATGGAGAGCTCCCGTGAGTGG3' (SEQ ID NO: 8),

5'CACCCTATTAACCACTCACG3' (SEQ ID NO: 9) and

5'TACATTACTGCCAGCCACCATG3' (SEQ ID NO: 10).

The mtDNA sequences experimentally obtained were compared to the 2001 Revised Cambridge Reference Sequence (Andrews et al., *Nat. Genet.* 23:147, 1999; Kogelnik et al., *Nucleic Acids Res.* 26:112, 1998) using the National Center for Biotechnology Information (NCBI) Blast2 program and the database search tool, MitoAnalyzer (National Institute of Standards and Technology, Gaithersburg, Md.), in order to identify polymorphisms and mutations. All automated results were manually confirmed. To exclude potential artifacts, PCR amplifications from original cell lysates were additionally replicated one or two more times: when nucleotide changes were reproduced in all independent PCR amplifications, they were considered to be confirmed.

To confirm the mtDNA control region sequence, PCR products were directly inserted into pCR®2.1-TOPO® vector and transformed into competent *E. coli* (TOP10 cells) using the TOPO TA™ cloning kit (Invitrogen, Carlsbad, Calif.). Recombinant plasmids isolated from 8 to 12 white colonies were subjected to sequencing.

Analysis of the set of 580 CD34$^+$ clones (clonal populations) from the five normal donors revealed that few CD34$^+$ clones obtained from umbilical cord blood had mtDNA heterogeneity. Specifically, only nine clones among the set of 580 CD34$^+$ clones analyzed (1.6%, 1.6±1.5) showed mtDNA heterogeneity (Tables 10 and 11) and the proportion of clones with a unique mtDNA heterogeneity pattern within the set of 580 CD34$^+$ clones was 1.2% (1.2±1.0). Except for clones with mtDNA heterogeneity, all CD34$^+$ clones from cord blood donors 2, 3 and 5 had the same pattern of length heteroplasmy in the poly C tracts between nucleotides 303 and 315 and nucleotides 16,183 and 16193. The mtDNA sequence of a single CD34$^+$ clone from cord blood donor 1 represented an extremely distinct pattern from the bulk BM mtDNA as well as from other CD34$^+$ clones (Table 10).

TABLE 10

Summary of mtDNA heterogeneity among single CD34⁺clones derived from cord blood

| CB donor | Heteroplasmy pattern | | No. of clones | Total | % |
|---|---|---|---|---|---|
| 1 | BM poly (+) alone | | 118 | 118 | 99.2 |
| | A73G | A153G | 1 | 1 | 0.8 |
| | A263G | A183G | | | |
| | 7C/6C | 8C/6C | | | |
| | del 514–515CA | C325T | | | |
| | C16,223T | C463T | | | |
| | C16,354T | T485C | | | |
| | T16,519C | T489C | | | |
| | | T16,198C | | | |
| | | C16,268T | | | |
| | | T16,381A | | | |
| | Subtotal | | 119 | 119 | 100 |
| 2 | BM poly (+) alone | | 120 | 120 | 100.0 |
| | Subtotal | | 120 | 120 | 100.0 |
| 3 | BM poly (+) alone | | 100 | 100 | 96.2 |
| | + G316G/C | | 3 | 4 | 3.8 |
| | + CCC305-307CCC/AAA | | 1 | | |
| | Subtotal | | 104 | 104 | 100 |
| 4 | BM poly (+) alone | | 118 | 118 | 99.2 |
| | + 6C/6C | | 1 | 1 | 0.8 |
| | + T16,022C | | | | |
| | Subtotal | | 119 | 119 | 100.00 |
| 5 | BM poly (+) alone | | 114 | 114 | 97.4 |
| | + C16,193CCC (12C) | | 1 | 3 | 2.6 |
| | + del 16,189T | | 1 | | |
| | + C16,193CCCC (13C) | | 1 | | |
| | Subtotal | | 117 | 117 | 100.0 |
| Total (summary) | BM poly (+) alone | | 571 | 571 | 98.1 |
| | Total No. of heterogeneity | | 9 | 9 | 1.6 |
| | Unique heterogeneity | | | 7 | 1.2 |
| | | | 580 | 580 | 580 |

Abbreviations: BM poly, mtDNA polymorphism from total bone marrow cells; +, mtDNA nucleotide changes in addition to the polymorphisms detected in the respective bulk mtDNA; *, poly C tract localized between np 303 and np 315.

A comparison of the characteristics between CD34⁺ clones derived from adult bone marrow and umbilical cord blood is presented in Table 11. Chi square test was used to test statistical differences in comparison of the frequency of heteroplasmy from adult bone marrow and cord blood. The one-way ANOVA (analysis of variance) test was performed to examine statistical differences in the effect of each grade and culture media on mtDNA heterogeneity; $P<0.05$ was considered significant. Remarkable diversity of the mtDNA sequence was observed in individual CD34⁺ clones from adult bone marrow, in contrast to the findings from cord blood.

TABLE 11

Comparison of characteristics between CD34⁺clones derived from adult bone marrow and umbilical cord blood.

| | Adult BM CD34⁺ | Cord Blood CD34⁺ |
|---|---|---|
| Plating Efficiency | 30% | 78.6%* |
| Bulk cell analysis | Uniform pattern | Frequently heteroplasmic |
| Heteroplasmy | | |
| Total rate | 22.6% | 1.6% |
| Unique pattern | 8.6% | 1.2% |

TABLE 11-continued

Comparison of characteristics between CD34⁺clones derived from adult bone marrow and umbilical cord blood.

| | Adult BM CD34⁺ | Cord Blood CD34⁺ |
|---|---|---|
| Plating Efficiency | 30% | 78.6%* |
| Bulk cell analysis | Uniform pattern | Frequently heteroplasmic |
| Substitution (S) | 10.6% (65/611) | 0.0% (0/580) |
| Poly C tract# | 10.8% (66/611) | 1.1% (7/580) |
| S + C | 1.1% (7/611) | 0.3% (2/580) |

*statistically significant difference ($P < 0.05$);

#mtDNA nucleotide sequence position at 303–315 and 16,183–16,193.

EXAMPLE 4

In Vivo Mutational Spectra of Mitochondrial Genomes and Evidence of the Clonal Expansion in Single Hematopoietic Progenitor Cell Clones This example provides a description of one embodiment in which the mutational frequency of the mtDNA control region, as well as genes (CO1 and Cytb) in the mtDNA coding region is measured in clonal populations of CD34⁺ cells and in single granulocytes.

Examples 2 and 3 demonstrated that an average of 25% of individual CD34⁺ clones from adult normal bone marrow differ in the control region of a mtDNA sequence from the bulk cell sequence and almost 8% of the mutations are uniquely different, in contrast to virtually homogenous mtDNA sequences in normal umbilical CB CD34⁺ clones. Thus, it is significant that the mutations detected in the bone marrow CD34⁺ clones were also found in circulating CD34⁺ cells and peripheral blood cells (single granulocytes). This demonstrates that mutational rates and monitoring of minimal residual disease can be evaluated by blood sampling rather than bone marrow aspiration. This example describes how the mutational frequency of mtDNA in circulating CD34⁺ cells and single granulocytes was examined.

To determine the heterogeneity of mtDNA sequences in single granulocytes and CD34⁺ cells, bone marrow (BM) and peripheral blood (PB) specimens from six normal (do not have any apparent hematologic disease or symptom) adult donors were collected and mononuclear cells from BM and PB were separated by density gradient centrifugation. The cells were then washed twice in PBS and the number of cells suspended in PBS was adjusted to $2\times10^7$ cells/ml. 10 μl of anti-CD34 phycoerythrin (PE)-conjugated monoclonal antibody and 10 μl anti-CD33 FITC-conjugated antibody (BD Bioscience, San Jose, Calif.) were added to each 12×75 mm tube containing 100 μl of cell suspension. After incubation for 30 minutes at 4° C., cells were washed using cold PBS and resuspended in 0.5 ml of PBS.

Cell sorting was performed on a MoFlo Cytometer (Dako-Cytomation, Ft Collins, Colo.), using one hundred milliwatts of the 488 nm line of an argon laser (I-90, Coherent Inc, Palo Alto, Calif.) for excitation. Forward scatter was the triggering parameter. Fluorescence of FITC was detected using a 530/20 bandpass filter and the fluorescence of PE was detected using a 580/30 bandpass filter. Single cell deposition was accomplished using the CyClone automated cloner (Dako-Cytomation); in the 0.5 single drop mode with gating based on forward scatter and fluorescence. Individual CD34⁺ cells were placed into each well of a 96-well microplate (Nalge Nunc International, Rochester, N.Y.) containing 100 μl of culture media and single granulocytes were deposited in each well of a MicroAmp® optical 96-well reaction plate (Applied Biosystems, Foster City, Calif.) containing 30 μl of 1× Tris EDTA (TE) buffer (FIG. 3A).

Individual CD34$^+$ cells placed into separate wells of 96-well plates were cultured in serum-free medium containing 100 ng/ml of stem cell factor, 100 ng/ml of Flt-3, 100 ng/ml of thrombopoietin, with 50 ng/ml of G-CSF (all from Stem Cell Technologies, Vancouver, Canada). After culture for 5 days, each well of the microtiter plate was carefully observed using an inverted microscope (Olympus IX50, Melville, N.Y.) in order to determine growth and plating efficiency of single CD34$^+$ cells. Grade growth was quantified with the following scoring system based on cell number in each CD34$^+$ clone: grade 1, ≦5 cells/well; grade 2, 6–10 cells/well; grade 3, 11–20 cells/well; grade 4, ≧21 cells/well (FIG. 3C). Plating efficiency (PEf) was defined as the number of positive (cells were present) wells÷total wells×100. Each CD34$^+$ clone was harvested from the well by vigorous pipetting and dispensed into a 1.5 ml microcentrifuge tube and rinsed with 200 μl of PBS. Cells were collected after centrifugation at 300-×g for 5 minutes, and then washed with PBS. CD34$^+$ cell pellets were then stored at −80° C. In order to extract DNA from individual CD34$^+$ clones, 30 μl of 1×TE buffer was placed in each 1.5 ml tube containing one cell pellet. The cells were lysed by incubation at 95° C. for 10 minutes with occasional shaking in order to liberate the total DNA. The resulting lysate was briefly centrifuged and stored at −20° C.

In order to extract DNA from single granulocytes deposited into each well of a 96-well microplate containing 30 μl of 1×TE buffer, the 96-well reaction plate (Applied Biosystems) was placed in a GeneAmp PCR system 9700 (Applied Biosystems) for incubation at 95° C. for 5 minutes. The resulting lysate was briefly centrifuged and stored at −20° C.

Cell lysates of individual CD34$^+$ clones and single granulocytes were then subjected to amplification of the mtDNA control region and coding region (CO1 and Cytb genes) using the LA PCR kit (TaKaRa LA Taq™, Madison, Wis.). Two-step PCR amplification was performed with outer and inner pairs of primers in order to generate sufficient template from CD34$^+$ clones and single granulocytes for sequencing of the mtDNA control region and coding region (CO1 and Cytb genes). Primer pairs for targeted mtDNA gene amplification and fragments spanning nucleotides position (amplicons size) are represented in Table 12.

TABLE 12

Primer sets for two-step PCR and direct sequencing of mtDNA control region, CO1 and Cytb genes

| Amplicon | MtDNA gene | Sequence (5' to 3') for two-step PCR | | Sequencing primers (5' to 3') | |
|---|---|---|---|---|---|
| 1 (1.12 kb) | Control region (16024–16569; 1–576) | F15574 (O) | CGCCTACACAATTCTCCGATC (O) (SEQ ID NO:1) | F15971 | TTAACTCCACCATTAGCACC (SEQ ID NO:7) |
| | | R921 (O) | ACTTGGGTTAATCGTGTGACC (O) (SEQ ID NO:2) | R1 | CAGTGTATTGCTTTGAGGAGG (SEQ ID NO:19) |
| | | F15971 (I) | TTAACTCCACCATTAGCACC (I) (SEQ ID NO:3) | SR | GCATGGAGAGCTCCCGTGAGTGG (SEQ ID NO:8) |
| | | R1 (I) | CAGTGTATTGCTTTGAGGAGG (I) (SEQ ID NO:5) | SF | CATCTGGTTCCTACTTCAGGGTC (SEQ ID NO:6) |
| 2 (1.39 kb) | CytB (14688–15996) | F14622 (O) | CCACAAACCCCATTACTAAACCCAC (O) (SEQ ID NO:11) | F14688 | CTACAACCACGACCAATGATATG (SEQ ID NO:20) |
| | | R16084 (O) | CGGTTGTTGATGGGTGAGTC (O) (SEQ ID NO:12) | R15996 | GCTTTGGGTGCTAATGGTGGAG (SEQ ID NO:21) |
| | | F14663 (I) | GCATACATCATTATTCTCGCACGG (I) (SEQ ID NO:13) | | |
| | | R16057 (I) | GGGTGGTACCCAAATCTGCTTCC (I) (SEQ ID NO:14) | | |
| 3 (0.91 kb) | CO1 (6611–7470) | F6541 (O) | GCAACCTCAACACCACCTTCTTCG (O) (SEQ ID NO:15) | F6645 | CTACCAGGCTTCGGAATAATCTCCC (SEQ ID NO:22) |
| | | R7613 (O) | GTAGACCTACTTGCGCTGCATGTGC (O) (SEQ ID NO:16) | R7425 | GTTCTTCGAATGTGTGGTAGGGTG (SEQ ID NO:23) |
| | | F6586 (I) | CCATTCTATACCAACACCTATTCTG (I) (SEQ ID NO:17) | | |
| | | R7498 (I) | CCATGGGGTTGGCTTGAAACCAGC (I) (SEQ ID NO:18) | | |

Abbreviations: Cytb, cytochrome b; CO1, cytochrome c oxidase 1; F, forward primer; R, reverse primer; O, outer primer; I, inner primer.

The primary PCR mixture contained 400 μM of each dNTP, 2 units of LA Taq™ (TaKaRa LA Taq™), 0.8 μM outer primers, 3 μl and 110 μl of cell lysates from individual CD34$^+$ clones and single granulocytes, respectively. PCR amplification was carried out in a MicroAmp® optical 96-well reaction plate (Applied Biosystems) using the GeneAmp PCR system 9700 (Applied Biosystems): one cycle of 95° C. for 1 minute; then 35 cycles of 95° C. for 30 seconds, 52° C. for 50 seconds and 72° C. for 1 minute with a 10 second increase per cycle; ending with one cycle of 72° C. for 5 minutes. The secondary PCR was performed in 50 μl of reaction mixture containing 400 μM of each dNTP, 2 units of LA Taq™, 0.8 μM inner nested primers and 2 μl of primary PCR product under the same amplification conditions as described above. Secondary PCR samples were electrophoresed on 1% agarose gels and stained with ethidium bromide to assess the purity and size of the DNA fragments, and subsequently purified using the QIA quick PCR purification kit (Qiagen, Valencia, Calif.). The negative controls, reaction mixtures without DNA templates, were subjected to the same PCR amplification conditions and in all cases, confirmed to be negative. To prevent DNA cross-contamination, special precautions were taken for each procedure of cell harvest, DNA extraction, PCR amplification and DNA sequencing. PCR amplification of mtDNA CO1 and Cytb genes was performed in the same manner described above. Corresponding primers for each gene amplification were listed in Table 12.

To assess heterogeneity of the mtDNA sequences in CD34+ clones and single granulocytes, the amplified control and coding regions were subjected to sequencing analysis. mtDNA genes were directly sequenced using the BigDye Terminator v3.1 ready reaction kit (Applied Biosystems) and the ABI Prism 3100 Genetic Analyzer (Applied Biosystems). Sequencing primers used in each mtDNA gene are shown in Table 12. MtDNA sequences experimentally obtained were compared to the revised Human mtDNA Cambridge Reference sequence (Andrews et al., *Nat. Genet.* 23:147, 1999; Kogelnik et al., *Nucleic Acids Res.* 26:112, 1998) using the NCBI Blast2 program and the database search tool, MitoAnalyzer (National Institute of Standards and Technology, Gaithersburg, Md.) in order to determine polymorphisms and mutations. All automated results were manually confirmed. To exclude potential artifacts, PCR amplifications from original cell lysates were additionally replicated one or two more times and when nucleotide changes were reproduced in all independent PCR amplifications, they were considered to be confirmed.

In preliminary experiments, 285 base pair amplicons were generated by gene amplification of wild type mtDNA and mtDNA altered in a single base and then mixed in varying proportions. On sequencing of the mixtures, the lower limit of detection of a minor species of mtDNA was approximately 20%. Mixed nucleotide signals on sequencing chromatograms, when observed in the current study, were assumed to represent at least 20% heteroplasmy but could also result from gene amplification artifacts. To confirm heteroplasmy and mixed nucleotide signals in the sequences of the mtDNA control region, PCR products were directly inserted into the pCR®2.1-TOPO® vector and transformed into competent *E. coli* (TOP10 cells) using the TOPO TA cloning kit (Invitrogen, Carlsbad, Calif.). Recombinant plasmids isolated from 8 to 12 white colonies were sequenced.

A Chi square test was used to determine statistical differences in the frequency of heteroplasmy in adult bone marrow and circulating blood. The one-way ANOVA (analysis of variance) test was performed to examine whether total rate and unique difference among cord blood CD34$^+$ clones, adult BM CD34$^+$ clones, circulating CD34$^+$ clones and single granulocytes produced significant statistical differences in mtDNA heterogeneity. $P<0.05$ was considered significant.

In order to identify mtDNA heterogeneity in individual CD34$^+$ clones and single granulocytes, the aggregate (bulk) cell genotype from total bone marrow cells from each donor was first examined (see Example 1, above). There was marked variation in the number of nucleotide changes among individual donors, with ranges of 6 (donor 1) to 23 (donor 4) (11.3±6.1, mean±SD) (Table 13A). A total of 68 mtDNA-sequence variants were found in bulk cells from six normal donors. Among these, 66 variants were already listed in the Mitomap polymorphism database and two new nucleotide variants were classified as mutations (A478G and A517G in donor 2 and 6, respectively). Donors 2 and 3 had length variations of the poly C tract at nucleotide positions 16,183–16,193 (T16,189C, 12C) and 303–315 (Table 13A).

TABLE 13

Nucleotide sequence changes of mtDNA control region (A) and coding region (B) from total (bulk) bone marrow cells

| Donor (Age/Sex) | Polymorphism (Mutation) | Affected mtDNA gene |
|---|---|---|
| A. Control region | | |
| 1 (47/F) | A73G | HV2, 7S |
| | C150T | HV2, 7S, OH |
| | A263G | HV2, OH |
| | 8CT6C* | HV2, OH, CSB2 |
| | C16,192T | HV1, 7S |
| | C16,270T | HV1, 7S |
| 2 (38/F) | A73G | HV2, 7S |
| | G185A | HV2, 7S, OH |
| | A263C | HV2 + OH |
| | C7T6C* | HV2, OH, CSB2 |
| | A478G[#] | |
| | T16,093C | HV1 |
| | A16,158G | HV1, 7S, TAS |
| | T16,172C | HV1, 7S, TAS |
| | A16,183C | HV1, 7S |
| | T16,189C (12C) | HV1, 7S |
| | A16,219G | HV1, 7S |
| | C16,278T | HV1, 7S |
| 3 (43/M) | A73G | HV2, 7S |
| | T146C | HV2, 7S, OH |
| | T152C | HV2, 7S, OH |
| | T195C | HV2, OH |
| | A263G | HV2, OH |
| | 9CT6C*, 8CT6C* | HV2 + OH + CSB2 |
| | del 514 C | |
| | del 515 A | |
| | C16,223T | HV1, 7S |
| | C16,278T | HV1, 7S |
| | C16,294T | HV1, 7S |
| | G16,390A | 7S |
| 4 (34/M) | A93G | HV2, 7S |
| | A95C | HV2, 7S |
| | G185A | HV2, 7S, OH |
| | A189G | HV2, 7S, OH |
| | T236C | HV2, OH |
| | 8CT6C* | HV2, OH, CSB2 |
| | G247A | HV2, OH, TFB1 |
| | A263G | HV2, OH |
| | del C 514 | |
| | del A 515 | |
| | T16,093C | HV1 |
| | G16,129A | HV1, 7S |
| | C16,148T | HV1, 7S |
| | C16,168T | HV1, 7S, TAS |
| | T16,172C | HV1, 7S, TAS |
| | C16,187T | HV1, 7S |
| | C16,188G | HV1, 7S |
| | T16,189C | HV1, 7S |
| | C16,223T | HV1, 7S |
| | A16,230G | HV1, 7S |
| | C16,278T | HV1, 7S |
| | A16,293G | HV1, 7S |
| | T16,311C | HV1, 7S |
| | C16,320T | HV1, 7S |
| 5 (54/M) | A73G | HV2, 7S |
| | A263G | HV2, OH |
| | 7CT6C* | HV2, OH, CSB2 |
| | del 514C | |
| | del 515A | |
| | T16,126C | HV1, 7S |
| | C16,294T | HV1, OH |
| | C16,296T | HV1, OH |
| | T16,519C | 7S |
| 6 (34/F) | A73G | HV2, 7S |
| | C150T | HV2, 7S, OH |
| | A263G | HV2, OH |
| | 8CT6C* | HV2, OH, CSB2 |
| | A517G[#] | |
| | C16,270T | HV1, 7S |
| | C16,292T | HV1, 7S |
| | T16,362C | HV1, 7S |

| Donors (Age/Sex) | MtDNA gene | Nucleotide change | Amino acid change | Polymorphism (P)/ Mutation (M) |
|---|---|---|---|---|
| B. coding region (CO1 and Cytb) | | | | |
| 1 (47/F) | CO1 | C7028T | No | P |
| | Cytb | A15326G | Thr–Ala | P |

TABLE 13-continued

| Nucleotide sequence changes of mtDNA control region (A) and coding region (B) from total (bulk) bone marrow cells | | | | |
|---|---|---|---|---|
| 3 (43/M) | CO1 | A6663G | Ile–Val | P |
| | CO1 | C7028T | No | P |
| | CO1 | T7175C | No | P |
| | CO1 | C7256T | No | P |
| | CO1 | C7274T | No | P |
| | Cytb | G15301A | No | P |
| | Cytb | A15326G | Thr–Ala | P |
| | Cytb | T15784C# | No | M |
| 5 (54/M) | CO1 | T7022C# | No | M |
| | CO1 | C7028T | No | P |
| | Cytb | C14766T | No | P |
| | Cytb | G14905A | No | P |
| | Cytb | A15326G | Thr–Ala | P |
| | Cytb | C15452A | Leu–Ile | P |
| | Cytb | A15607G | No | P |

Abbreviations: HV1, hypervariable segment 1; HV2, hypervariable segment 2; 7S, 7S DNA; OH, H-strand origin; CSB2,conserved sequence block II; TAS, termination-association sequence; TFB1, mitochondrial transcription factor 1 binding site;

*homopolymeric C tract localized between nucleotide 303 and 315 (for example, 8CT6C defined CCCCCCCCTCCCCCC);

#new mtDNA polymorphisms (not listed in accepted database); Ala, alanine; Ile, isoleucine; Leu, leucine; Thr, threonine; Val, valine.

The bulk genotype of the mtDNA coding region (CO1 and Cytb genes) from total bone marrow cells was also examined. A total of 17 mtDNA nucleotide changes (5.7±3.7, mean±SD) were noted in the CO1 and Cytb genes among three donors (Table 13B): 15 nucleotide variants were already listed in the published Mitomap polymorphism database and 2 new sequence variations were identified that were not previously recorded (including among unpublished mtDNA polymorphisms). These two mutations were not predicted to produce amino acid change (Table 13B).

$CD34^+$ cell-derived colonies cultured in individual wells of 96-well plates in serum-free medium containing selected hematopoietic growth factors were classified according to the cell number per well (FIG. 3C). Although there was some variation of plating efficiency of $CD34^+$ cells among six normal, overall average plating efficiency in PB and BM was 45% (45.3±9.3, mean±SD) and 36% (35.7±3.6) respectively (Table 13A). This difference was not statistically significant (P=0.12).

The mtDNA control regions from a total of 4,704 single granulocytes from six donors was amplified using a double nested PCR. A summary of the amplification results is provided in Table 14A. From the 4,704 granulocytes, 355 (8%) (7.5±4.2, mean±SD) produced a product of the correct size.

TABLE 14

$CD34^+$ clones from peripheral blood and bone marrow, and single granulocyte for mtDNA analysis A. Plating efficiency and grade of $CD34^+$ clones after 5 day-suspension culture, and nested mtDNA PCR efficiency from single granulocytes

| Sample | PB $CD34^+$ clone | | | | | | | BM $CD34^+$ clone | | | | | | | Single granulocyte mtDNA PCR | | |
|---|---|---|---|---|---|---|---|---|---|---|---|---|---|---|---|---|---|
| | Grade | | | | Sub- | Micro- | PEf | Grade | | | | Sub- | Micro- | PEf | Granulocyte | PCR efficiency | |
| Donor | 1 | 2 | 3 | 4 | total | plate* | (%) | 1 | 2 | 3 | 4 | total | plate | (%) | No | Positive No | % |
| 1 (47/F) | 13 | 54 | 128 | 85 | 280 | 5 | 58.3 | 33 | 21 | 30 | 38 | 122 | 4 | 31.8 | 480 | 51 | 10.6 |
| 2 (38/F) | 33 | 61 | 64 | 34 | 192 | 4 | 50.0 | — | — | — | — | — | — | — | 1440 | 37 | 2.6 |
| 3 (43/M) | 24 | 20 | 23 | 26 | 93 | 3 | 32.3 | 279 | 149 | 91 | 127 | 646 | 20 | 33.6 | 480 | 50 | 10.4 |
| 4 (34/M) | 38 | 38 | 58 | 66 | 200 | 5 | 41.7 | — | — | — | — | — | — | — | 768 | 111 | 14.5 |
| 5 (54/M) | 35 | 50 | 61 | 36 | 182 | 5 | 37.9 | 306 | 177 | 119 | 140 | 742 | 20 | 38.6 | 768 | 42 | 5.5 |
| 6 (34/F) | 37 | 46 | 52 | 92 | 227 | 5 | 47.3 | — | — | — | — | — | — | — | 768 | 64 | 8.3 |
| Total | 180 | 269 | 386 | 339 | 1174 | 27 | 45.3 | 618 | 347 | 240 | 305 | 1510 | 44 | 35.7 | 4704 | 355 | 7.5 |

Abbreviations: PB, peripheral blood; BM, bone marrow; suspension culture media containing 100 ng/ml of each stem cell factor (SCF), Flt-3 and thrombopoietin (TPO), free-serum media and 50 ng/ml of G-CSF; PEf, planting efficiency; grade 1, less than 5 cells/well; grade 2, 6 to 10 cells/well; grade 3, 11 to 20 cells/well; grade 4, more than 21 cells/well;

*No of 96 well microplates.

B. Assay number

| | Control region | | | | | | | | | | | Coding region (CO1 and Cytb) | | | | | | | | | |
|---|---|---|---|---|---|---|---|---|---|---|---|---|---|---|---|---|---|---|---|---|---|
| | BM $CD34^+$ clone | | | | | PB $CD34^+$ clone | | | | | | BM $CD34^+$ clone | | | | | PB $CD34^+$ clone | | | | |
| MtDNA Donor | G1 | G2 | G3 | G4 | Sub-total | G1 | G2 | G3 | G4 | Sub-total | Single granulocyte | G1 | G2 | G3 | G4 | Sub-total | G1 | G2 | G3 | G4 | Sub-total |
| 1 (47/F) | 28 | 20 | 30 | 37 | 115 | 13 | 30 | 47 | 30 | 120 | 51 | 29 | 20 | 29 | 18 | 96 | 13 | 30 | 35 | 18 | 96 |
| 2 (38/F) | 23 | 3 | 4 | 6 | 36 | 23 | 24 | 23 | 24 | 94 | 37 | — | — | — | — | — | — | — | — | — | — |
| 3 (43/M) | 30 | 30 | 30 | 30 | 120 | 24 | 20 | 23 | 26 | 93 | 50 | 26 | 26 | 24 | 20 | 96 | 24 | 20 | 23 | 26 | 93 |

TABLE 14-continued

CD34$^+$ clones from peripheral blood and bone marrow, and single granulocyte for mtDNA analysis

| | | | | | | | | | | | | | | | | | | | | | |
|---|---|---|---|---|---|---|---|---|---|---|---|---|---|---|---|---|---|---|---|---|---|
| 4 (34/M) | 26 | 28 | 28 | 29 | 111 | 24 | 24 | 24 | 24 | 96 | 111 | — | — | — | — | — | — | — | — | — | — |
| 5 (54/M) | 26 | 28 | 30 | 30 | 114 | 24 | 23 | 24 | 24 | 95 | 42 | 25 | 29 | 30 | 12 | 96 | 24 | 24 | 24 | 24 | 96 |
| 6 (34/F) | 25 | 30 | 30 | 30 | 115 | 24 | 24 | 24 | 24 | 96 | 64 | — | — | — | — | — | — | — | — | — | — |
| Total | 158 | 139 | 152 | 162 | 611 | 133 | 146 | 166 | 152 | 594 | 355 | 80 | 75 | 83 | 50 | 288 | 61 | 74 | 82 | 68 | 285 |

Abbreviations: G, grade; CO1, cytochrome c oxidase 1; Cytb, cytochrome b.

To assess the neutral mutational spectra of the mtDNA sequences and their clonal expansion among CD34$^+$ clones and single granulocytes, the 1,121 base pair mtDNA control region, which contains multiple mutational hot spots (FIG. 3B) was examined. On average, 100 CD34$^+$ clones from each donor was subjected to sequencing analysis. A total number of 594 circulating (peripheral blood) CD34$^+$ clones were examined from six adult donors (Table 14B) and a total of 355 single granulocytes from the same six donors were used directly for sequencing analysis to investigate the evidence of clonal expansion of neutral mutations in these cells (Table 14B).

As observed in Example 2, above, marked sequence heterogeneity (mtDNA neutral mutations) was detected in cells from all of the donors. Analysis of 594 circulating CD34$^+$ clones revealed that a total of 151 clones (25.4±8.4%, mean±SD) displayed mtDNA heterogeneity that was distinct from the donor's corresponding bulk mtDNA sequences (Tables 15 and 16). Common patterns of mtDNA heterogeneity in the circulating CD34$^+$ clones among the six donors included one or two nucleotide changes (substitution, insertion or deletion) in addition to the polymorphisms detected in the bulk mtDNA. Most differences were due to single nucleotide substitutions at various nucleotide positions and to length alterations in the homopolymeric C tract that is localized between nucleotide 303 and nucleotide 315. The mtDNA heterogeneity of CD34$^+$ clones in six donors was classified into several patterns according to nucleotide changes: donors 1 through 6 had 5, 3, 3, 5, 9 and 6 different types of nucleotide change, respectively (Table 15). The mean proportion of unique patterns of mtDNA heterogeneity among the CD34$^+$ clones from peripheral blood was 5.2% (5.2±2.2) (Table 15).

One hundred and three of 355 single granulocytes (29%, 29.0±9.1) from the same six donors showed mtDNA heterogeneity that was distinct from mtDNA sequences of the donor's corresponding bulk mtDNA and from other single granulocytes (Table 15). The mean proportion of unique patterns of mtDNA heterogeneity among single granulocytes was 15.2% (15.2±5.2).

TABLE 15

Mutational spectra of mtDNA control region in individual CD34 clones and single granulocytes

| | A. BM CD34$^+$ clones | | | | | | B. PB CD34$^+$ clones | | | | | | C. single granulocyte | | | | | |
|---|---|---|---|---|---|---|---|---|---|---|---|---|---|---|---|---|---|---|
| | | | Heterogeneity | | | | | | Heterogeneity | | | | | | Heterogeneity | | | |
| | | | Frequency | | Unique | | | | Frequency | | Unique | | | | Frequency | | Unique | |
| Donor | MtDNA sequence | Clone No | No | % | No | % | MtDNA sequence | Clone No | No | % | No | % | MtDNA sequence | Clone No | No | % | No | % |
| 1 (47/F) | 'bulk' sequence | 85 | 30 | 26.1 | 8 | 7.0 | 'bulk' sequence | 90 | 30 | 25.0 | 5 | 4.2 | 'bulk' sequence | 40 | 11 | 21.6 | 5 | |
| | +8CT6C*, 9CT6C* | 22 | | | | | +8CT6C*, 9CT6C* | 23 | | | | | | | | | | 9.8 |
| | +9CT6C* | 2 | | | | | +9CT6C*, 10CT6C* | 4 | | | | | +9CT6C*, 10CT6C* | 7 | | | | |
| | +7CT6C* | 1 | | | | | | | | | | | +7CT6C* | 1 | | | | |
| | +A189G/A | 1 | | | | | +G16129A/G | 1 | | | | | +10CT6C*, 11CT6C | 1 | | | | |
| | +T204C | 1 | | | | | +G16129A | 1 | | | | | +C349T/C(M), A368G(M) | 1 | | | | |
| | +C277T | 1 | | | | | +C16256T/C | 1 | | | | | +C369T (M) | 1 | | | | |
| | +ins 514CA | 1 | | | | | | | | | | | | | | | | |
| | +C16114T | 1 | | | | | | | | | | | | | | | | |
| | Subtotal | 115 | | | | | Subtotal | 120 | | | | | Subtotal | 51 | | | | |
| 2 (38/F) | 'bulk' sequence | 27 | 9 | 25.0 | 5 | 13.9 | 'bulk' sequence | 85 | 9 | 9.6 | 3 | 3.2 | 'bulk' sequence | 24 | 13 | 35.1 | 3 | 8.1 |
| | +C16184CC (11C) | 5 | | | | | +C16184CC (11C) | 5 | | | | | +C16184CC (11C) | 11 | | | | |
| | +T16131C/T | 1 | | | | | +C16184-CCCC (13C) | 3 | | | | | +C16184CCCC (13C) | 1 | | | | |
| | +G16145A | 1 | | | | | +A478G/A | 1 | | | | | +C16459T (M) | 1 | | | | |

TABLE 15-continued

Mutational spectra of mtDNA control region in individual CD34 clones and single granulocytes

| | A. BM CD34+ clones | | | | | | B. PB CD34+ clones | | | | | | C. single granulocyte | | | | | |
|---|---|---|---|---|---|---|---|---|---|---|---|---|---|---|---|---|---|---|
| | | | Heterogeneity | | | | | | Heterogeneity | | | | | | Heterogeneity | | | |
| | | | Frequency | | Unique | | | | Frequency | | Unique | | | | Frequency | | Unique | |
| Donor | MtDNA sequence | Clone No | No | % | No | % | MtDNA sequence | Clone No | No | % | No | % | MtDNA sequence | Clone No | No | % | No | % |
| | +C16184-CCCC (13C) | 1 | | | | | | | | | | | | | | | | |
| | A73G, A263G, A191AA, C194T, T199C, G207A 8CT6C*, T489C, C16147T, C16173T, C16245T, T16362C | 1 | | | | | | | | | | | | | | | | |
| | Subtotal | 36 | | | | | Subtotal | 94 | | | | | Subtotal | 37 | | | | |
| 3 (43/M) | 'bulk' sequence | 96 | 24 | 20.0 | 7 | 5.8 | 'bulk' sequence | 66 | 27 | 29.0 | 3 | 3.2 | 'bulk' sequence | 34 | 16 | 32.0 | 10 | |
| | +9CT6C*, 10CT6C* | 11 | | | | | +9CT6C*, 10CT6C* | 26 | | | | | +9CT6C*, 10CT6C* | 4 | | | | 20.0 |
| | +9CT6C* | 6 | | | | | | | | | | | +8CT6C* | 5 | | | | |
| | +8CT6C* | 2 | | | | | +8CT6C*, 9CT6C*, T16124C/T | 1 | | | | | | | | | | |
| | +C182T/C, 8CT6C*, 9CT6C* | 2 | | | | | | | | | | | +8CT6C*, 9CT6C*, C104T(M) | 1 | | | | |
| | +del 71G, 9CT6C*, 10CT6C* | 1 | | | | | | | | | | | +8CT6C*, 9CT6C*, A181A/G(M) | 1 | | | | |
| | +T279C/T | 1 | | | | | | | | | | | +8CT6C*, 9CT6C*, C296C/T(M) | 1 | | | | |
| | +G16153A | 1 | | | | | | | | | | | +8CT6C*, 9CT6C*, C16339T(M) | 1 | | | | |
| | | | | | | | | | | | | | +8CT6C*, 9CT6C*, T16352T/C | 1 | | | | |
| | | | | | | | | | | | | | +9CT6C*, 10CT6C*, G225A, T16263C | 1 | | | | |
| | | | | | | | | | | | | | +8CT6C*, 9CT6C*, G16035A | 1 | | | | |
| | Subtotal | 120 | | | | | Subtotal | 93 | | | | | Subtotal | 50 | | | | |
| 4 (34/M) | 'bulk' sequence | 92 | 19 | 17.4 | 6 | 5.4 | 'bulk' sequence | 70 | 25 | 26.3 | 5 | 5.3 | 'bulk' sequence | 77 | 34 | 30.6 | 16 | 14.4 |
| | +8CT6C*, 9CT6C* | 11 | | | | | +8CT6C*, 9CT6C* | 16 | | | | | +8CT6C*, 9CT6C* | 6 | | | | |
| | +del514-515CA, ins 514CA* | 3 | | | | | +7CT6C*, 8CT6C* | 3 | | | | | +7CT6C*, 8CT6C* | 3 | | | | |
| | +7CT6C*, 8CT6C* | 2 | | | | | +T16093T/C | 4 | | | | | +9CT6C*, 10CT6C* | 6 | | | | |
| | +9CT6C*, 10CT6C* | 1 | | | | | +8CT6C*, 9CT6C*, T16044C/T (M) | 1 | | | | | +9CT6C*, 10CT6C*, T16093T/C | 2 | | | | |
| | +T89C | 1 | | | | | | | | | | | | | | | | |
| | +8CT6C*, 9CT6C*, T16,093T | 1 | | | | | +8CT6C*, 8CT7C | 1 | | | | | T16093T/C | 3 | | | | |
| | | | | | | | | | | | | | +16093T* | 4 | | | | |

TABLE 15-continued

Mutational spectra of mtDNA control region in individual CD34 clones and single granulocytes

| | A. BM CD34+ clones | | | | | | B. PB CD34+ clones | | | | | | C. single granulocyte | | | | | |
|---|---|---|---|---|---|---|---|---|---|---|---|---|---|---|---|---|---|---|
| | | | Heterogeneity | | | | | | Heterogeneity | | | | | | Heterogeneity | | | |
| | | | Frequency | | Unique | | | | Frequency | | Unique | | | | Frequency | | Unique | |
| Donor | MtDNA sequence | Clone No | No | % | No | % | MtDNA sequence | Clone No | No | % | No | % | MtDNA sequence | Clone No | No | % | No | % |
| | | | | | | | | | | | | | +16093T*, G16208A (M) | 1 | | | | |
| | | | | | | | | | | | | | +A28G/A (M) | 1 | | | | |
| | | | | | | | | | | | | | +8CT6C*, 9CT6C, G185G/A | 1 | | | | |
| | | | | | | | | | | | | | +T195T/C | 1 | | | | |
| | | | | | | | | | | | | | +T195C, A161675C (M) | 1 | | | | |
| | | | | | | | | | | | | | +C277T (M) | 1 | | | | |
| | | | | | | | | | | | | | +C315C/T | 1 | | | | |
| | | | | | | | | | | | | | +C411T (M) | 1 | | | | |
| | | | | | | | | | | | | | +del 452T (M) | 1 | | | | |
| | | | | | | | | | | | | | +C469T (M), T16093T/C | 1 | | | | |
| | Subtotal | 111 | | | | | Subtotal | 95 | | | | | Subtotal | 111 | | | | |
| 5 (54/M) | 'bulk' sequence | 57 | 57 | 50.0 | 14 | 12.3 | 'bulk' sequence | 63 | 33 | 34.4 | 9 | 9.4 | 'bulk' sequence | 22 | 20 | 47.6 | 14 | 33.3 |
| | +ins 514CA | 19 | | | | | +ins 515GA[5] | 11 | | | | | +C264T | 7 | | | | |
| | +C264T | 18 | | | | | +C264T | 11 | | | | | +T146C | 1 | | | | |
| | +del514-515CA, ins 514CA* | 5 | | | | | +C264T/C | 2 | | | | | +7CT6C*, 8CT6C* | 1 | | | | |
| | +C264T/C | 3 | | | | | +T146C/T, ins 514CA[5] | 4 | | | | | +8CT6C | 1 | | | | |
| | +7CT6C*, 8CT6C* | 2 | | | | | | | | | | | | | | | | |
| | +T146C, 514-515CA | 2 | | | | | +G94A/G | 1 | | | | | +T321T/C (M) | 1 | | | | |
| | +T146C, C264T/C | 1 | | | | | +C320C/A | 1 | | | | | +A376G (M) | 1 | | | | |
| | +T146C/T, ins 514CA[5] | 1 | | | | | +T16189C | 1 | | | | | +T582T/C (M), T16075C/T | 1 | | | | |
| | +T146C | 1 | | | | | +A16265G | 1 | | | | | +T1605C/T (M) | 1 | | | | |
| | +A189G | 1 | | | | | +A357AA (M), ins 514[5], T16136C/T | 1 | | | | | +A16098A/G | 1 | | | | |
| | +C264T/C, 514-515CA | 1 | | | | | | | | | | | +C16259G | 1 | | | | |
| | +T161C/T, C264T, ins 514CA[5] | 1 | | | | | | | | | | | +G16274A, C16296T/C | 1 | | | | |
| | +T16,189C | 1 | | | | | | | | | | | +C16292T | 1 | | | | |
| | +C16,296C/T | 1 | | | | | | | | | | | +C16332T (M), C16366T | 1 | | | | |
| | | | | | | | | | | | | | +T16422C | 1 | | | | |
| | Subtotal | 114 | | | | | Subtotal | 96 | | | | | Subtotal | 42 | | | | |
| 6 (34/F) | 'bulk' sequence | 102 | 13 | 11.3 | 6 | 5.6 | 'bulk' sequence | 69 | 27 | 28.1 | 6 | 6.3 | 'bulk' sequence | 55 | 9 | 14.1 | 6 | 9.4 |
| | +8CT6C*, 9CT6C* | 5 | | | | | +8CT6C*, 9CT6C* | 18 | | | | | +8CT6C*, 9CT6C* | 4 | | | | |
| | +A200G/A | 3 | | | | | +A200G/A | 4 | | | | | | | | | | |
| | +A200G | 2 | | | | | +A200G | 1 | | | | | +A28G (M) | 1 | | | | |
| | +A200G/A, 7CT6C*, 8CT6C* | 1 | | | | | +A200G/A, 8CT6C*, 9CT6C* | 2 | | | | | +C571A (M) | 1 | | | | |

TABLE 15-continued

Mutational spectra of mtDNA control region in individual CD34 clones and single granulocytes

| | A. BM $CD34^+$ clones | | | | | | B. PB $CD34^+$ clones | | | | | | C. single granulocyte | | | | | |
|---|---|---|---|---|---|---|---|---|---|---|---|---|---|---|---|---|---|---|
| | | | Heterogeneity | | | | | | Heterogeneity | | | | | | Heterogeneity | | | |
| | | | Frequency | | Unique | | | | Frequency | | Unique | | | | Frequency | | Unique | |
| Donor | MtDNA sequence | Clone No | No | % | No | % | MtDNA sequence | Clone No | No | % | No | % | MtDNA sequence | Clone No | No | % | No | % |
| | +A200G/A, 8CT6C*, 9CT6C* | 1 | | | | | | | | | | | +A16080G/A | 1 | | | | |
| | +7CT6C*, 8CT6C* | 1 | | | | | | | | | | | +A16116G (M) | 1 | | | | |
| | | | | | | | +A234G/A | 1 | | | | | +G16412G/A | 1 | | | | |
| | | | | | | | +C16111T/C | 1 | | | | | | | | | | |
| | Subtotal | 115 | | | | | Subtotal | 96 | | | | | Subtotal | 64 | | | | |
| Total | | 611 | 152 | 24.9 | 46 | 7.5 | | 594 | 151 | 25.4 | 31 | 5.2 | | 355 | 103 | 29.0 | 54 | 15.2 |

Abbreviations: Different, different from bulk cell sequence, Unique, uniquely different heterogeneity; +, mtDNA nucleotide changes in comparison to bulk cell mtDNA sequence; BM, bone marrow; PB, peripheral blood; s, the same as the Cambridge Reference Sequence but different from the bulk sequence.

TABLE 16

Summary of mtDNA neutral mutations in CD $34^+$ clones and single granulocytes

| | | | Heterogeneity (neutral mutation) | | | | | | | | |
|---|---|---|---|---|---|---|---|---|---|---|---|
| | | | | | | Poly C tract | | | | | |
| MtDNA genes | Specimens | Assay No (Donor No) | Total rate (No) | Unique (No) | Substitution (No) | np 303-315 | np 16184-16189 | NC | AA change (No) | Interpretation P (No) | M (No) |
| Control Region | CB $CD34^{+\#}$ | 580 (5) | 1.6% (9) | 1.2% (7) | 0.0% (0) | 0.0% (0) | 0.5% (3) | 0.7% (4) | | | |
| | Adult BM $CD34^{+\#}$ | 611 (6) | 24.9% (152) | 7.5% (46) | 10.5% (64) | 10.8% (66) | 1.1% (7) | 0.0% (0) | | | |
| | Adult PB $CD34^+$ | 594 (6) | 25.4% (151) | 5.2% (31) | 7.9% (47) | 15.3% (91) | 1.5% (9) | 0.0% (0) | | | |
| | Single granulocyte | 355 (6) | 29.0% (103) | 15.2% (54) | 11.8% (42) | 11.8% (42) | 2.0% (12) | 0.0% (0) | | | |
| CO1, Cytb | Adult BM $CD34^+$ | 285 (3) | 3.9% (11) | 3.9% (11) | 3.9% (11) | | | | 61.5% (8/13*) | 30.8% (4/13) | 69.2% (9/13) |
| | Adult PB $CD34^+$ | 284 (3) | 6.7% (19) | 5.6% (16) | 6.7% (19) | | | | 43.5% (10/23*) | 56.5% (13/23) | 43.5% (10/23) |
| | Subtotal | 569 (6) | 5.3% (30) | 4.7% (27) | 5.3% (30) | | | | 50.0% (18/36*) | 47.2% (17/36) | 52.8% (19/36) |

Abbreviations:
CB, cord blood;
np, nucleotide position;
AA, amino acid;
NC, nucleotide change;
P, polymorphism;
M, mutation;
*total No of mutational events.

The mtDNA mutational frequency of the CO1 and Cytb genes, located in the mtDNA coding region, were examined in order to determine the functional significance of mtDNA heterogeneity among bone marrow (BM) $CD34^+$ and peripheral blood $CD34^+$ clones. CO1 and Cytb gene products are central components of respiratory chain complex III and IV in mitochondria. Cytb mutations may not only damage complex III, but by interfering with the flow of electrons through the respiratory chain, they may also affect the function of complex IV (cytochrome c oxidase) (DiMauro and Schon, *N. Eng. J. Med.* 348:2656-2668, 2003). Complex IV may be the site of iron reduction for heme synthesis (Gattermann, *Leuk. Res.,* 24:141-151, 2000).

Analysis of 569 $CD34^+$ clones from BM (285 clones) and peripheral blood (PB) (284 clones) from 3 donors showed that 5.3% (30 clones) had mutations distinct from the donor's corresponding bulk sequences (Table 13B). All of the mtDNA heterogeneity (neutral mutations) were nucleic acid base substitutions. The mean proportion of unique mtDNA neutral mutations was 4.7% (27 clones) (15.2±5.2). Half of them led into amino acid changes (Table 17).

TABLE 17

Mutational spectra of mtDNA CO1 and Cytb genes in individual CD34+ clones from BM and PB

| | A. BM CD34+ clones | | | | | | | | | B. PB CD34+ clones | | | | | | | | |
|---|---|---|---|---|---|---|---|---|---|---|---|---|---|---|---|---|---|---|
| | | | Amino | | | Heterogeneity | | | | | | Amino | | | Heterogeneity | | | |
| Do- | MtDNA | | acid | Interpre- | Clone | Frequency | | Unique | | MtDNA | | acid | Interpre- | Clone | Frequency | | Unique | |
| nor | sequence | Gene | change | tation | No | No | % | No | % | sequence | Gene | change | tation | No | No | % | No | % |
| 1 (47/F) | 'bulk' sequence | | | | 91 | 3 | 3.2 | 3 | 3.2 | 'bulk' sequence | | | | 91 | 4 | 4.2 | 4 | 4.2 |
| | +T7071C/T | CO1 | Met-Thr | Mutation/TS | 1 | | | | | +T6952C | CO1 | Val-Ala | Mutation/TS | 1 | | | | |
| | +G7207G/A | CO1 | Gly-Glu | Mutation/TS | 1 | | | | | +T7312C | CO1 | Phe-Ser | Mutation/TS | 1 | | | | |
| | +T14924C | Cytb | Ser-Pro | Mutation/TS | 1 | | | | | +C14832C/G | Cytb | Ala-Gly | Mutation/TV | 1 | | | | |
| | | | | | | | | | | +A15098A/G | Cytb | Ile-Val | Mutation/TS | 1 | | | | |
| | Subtotal | | | | 94 | | | | | Subtotal | | | | 95 | | | | |
| 3 (43/M) | 'bulk' sequence | | | | 92 | 3 | 3.2 | 3 | 3.2 | 'bulk' sequence | | | | 89 | 4 | 4.3 | 4 | 4.3 |
| | +G6955G/A | CO1 | Gly-Asp | Mutation/TS | 1 | | | | | +G6955G/A | CO1 | Gly-Asp | Mutation/TS | 1 | | | | |
| | +T6987C/T | CO1 | Ser-Pro | Mutation/TS | 1 | | | | | +T14935C | Cytb | No | Mutation/TS | 1 | | | | |
| | +T7110T/C | CO1 | Tyr-His His | Mutation/TS TS | 1 | | | | | +T1506T/C | Cytb | No | Poly-morphism/TS | 1 | | | | |
| | | | | | | | | | | +A15724G/A | Cytb | No | Poly-morphism/TS | 1 | | | | |
| | Subtotal | | | | 95 | | | | | Subtotal | | | | 93 | | | | |
| 5 (54/M) | 'bulk' sequence | | | | 91 | 5 | 5.2 | 5 | 5.2 | 'bulk' sequence | | | | 85 | 11 | 11.5 | 8 | 8.3 |
| | +T6711G/T | CO1 | Tyr-Asp Asp | Mutation/TV TV | 1 | | | | | +T7022T/C | CO1 | No | Poly-morphism/TS | 4 | | | | |
| | +G6899A/G | CO1 | No | Mutation/TS | 1 | | | | | +G7075A/G | CO1 | No | Mutation/TS | 1 | | | | |
| | +7022T | CO1 | | | 1 | | | | | +T14864C | Cytb | Cys-Arg | Mutation/TS | 1 | | | | |
| | +T7297C/T | CO1 | Val-Ala Ala | Mutation/TS TS | 1 | | | | | +T15067T/C | Cytb | No | Poly-morphism/TS | 1 | | | | |
| | +15607A | Cytb | | | | | | | | +T15132C | Cytb | Met-Thr | Mutation/TS | 1 | | | | |
| | G14905G/A, | | No | Poly-morphism/TS | 1 | | | | | +T15818C | Cytb | Tyr-His | Mutation/TS | 1 | | | | |
| | T15067C | | No | Poly-morphism/TS | | | | | | +C15452C/A, | Cytb | Leu-Ile | Poly-morphism/TS | 1 | | | | |
| | | | | | | | | | | A15607A/G | | No | Poly-morphism/TS | | | | | |
| | | | | | | | | | | +G14905G/A, | Cytb | No | Poly-morphism/TS | 1 | | | | |
| | | | | | | | | | | T15067T/C | | No | Poly-morphism/TS | | | | | |
| | | | | | | | | | | C15452C/A, | | Leu-Ile | Poly-morphism/TS | | | | | |

TABLE 17-continued

Mutational spectra of mtDNA CO1 and Cytb genes in individual CD34⁺ clones from BM and PB

| | A. BM $CD34^+$ clones | | | | | | | | | B. PB $CD34^+$ clones | | | | | | | | |
|---|---|---|---|---|---|---|---|---|---|---|---|---|---|---|---|---|---|---|
| | | | Amino | | | Heterogeneity | | | | | | Amino | | | Heterogeneity | | | |
| Do- | MtDNA | | acid | Interpre- | Clone | Frequency | | Unique | | MtDNA | | acid | Interpre- | Clone | Frequency | | Unique | |
| nor | sequence | Gene | change | tation | No | No | % | No | % | sequence | Gene | change | tation | No | No | % | No | % |
| | | | | | | | | | | A15607A/G | | No | Poly-morphism/TS | | | | | |
| | Subtotal | | | | 96 | | | | | Subtotal | | | | 96 | | | | |
| Total | | | | | 285 | 11 | 3.9 | 11 | 3.9 | | | | | 284 | 19 | 6.7 | 16 | 5.6 |
| | | Heterogeneity of mtDNA CO1 and Cytb genes in total $CD34^+$ clones from BM and PB | | | | | | | | | | | | 569 | 30 | 5.3 | 27 | 4.7 |

Abbreviations and symbols used in Table 17 include: CO1, cytochrome c oxidase 1; Cytb, cytochrome b; BM, bone marrow; PB, peripheral blood; TS, transition; TV, transversion; s, the same as the Cambridge Reference Sequence but different from the bulk (aggregate) sequence.

Analysis of 355 single granulocytes from six donors revealed that 63 cells (17.7%, 63/355) had the same mutations found in their progenitor cells (BM $CD34^+$ and/or circulating $CD34^+$). In most cases, there were one or two mutations in each cell. The majority of clonally expanded mutations in hematopoietic tissue are length changes in the homopolymeric C tract between nucleotide 303 and nucleotide 315 at hypervariable segment 2. Clonal expansion among substitution mutations, such as T16093T/C and C264T, were also observed in donors 4 and 5 (Table 15). These data indicate that each of these mutations expanded from a single initial mutational event.

The characteristics of mtDNA mutations in cells obtained from different hematopoietic tissues are summarized in Table 16. On average, approximately 25% of single granulocytes and $CD34^+$ cell clones from adult BM and PB differed from the bulk mtDNA sequence of each specific donor. In contrast, less than 2% of the cord blood (CB) $CD34^+$ cell clones were different from their respective individual bulk sequence (see also Example 3). The proportion of unique differences (different from the bulk sequence and other $CD34^+$ clones and granulocytes) was 7.5%, 5.2% and 15.2% in BM $CD34^+$ cells, circulating $CD34^+$ cells, and single granulocytes, respectively. The proportion of solitary nucleotide substitutions in BM $CD34^+$ cells, circulating $CD34^+$ cells, and single granulocytes was similar and these substitutions were not observed in CB $CD34^+$ clones.

As discussed in Example 2, above, a high incidence of nucleotide variations was also observed in both HV2 and HV1 segments among circulating $CD34^+$ clones and single granulocytes. Most mutations from circulating $CD34^+$ clones and single granulocytes were localized in the HV2 homopolymeric C tracts between nucleotide 303 and nucleotide 315 (60.3% or 91/151 in PB $CD34^+$ clones; 40.8% or 42/103 in single granulocytes) (Table 16).

EXAMPLE 5

MtDNA Heterogeneity in Single $CD34^+$ Cell Clones from Normal Bone Marrow without Amplification of the MtDNA This example provides a description of one embodiment in which the mutational frequency in mtDNA is measured in clonal populations of $CD34^+$ cells but where the mtDNA is sequenced without prior amplification.

To determine the heterogeneity of mtDNA sequences in $CD34^+$ cells from umbilical cord blood, normal umbilical cord blood is collected from five normal (do not have any apparent hematologic disease or symptom) donors. Alternatively, peripheral blood, or bone marrow samples are collected from the donors either instead of, or in addition to, the umbilical cord blood samples.

In order to determine the heterogeneity of single $CD34^+$ clones from umbilical cord blood, mononuclear cells are separated from other hematopoietic cells by standard Ficoll separation and washed twice in phosphate-buffered saline (PBS). Cells suspended in PBS are adjusted to $2\times10^7$ cells/ml. To each 12×75 mm tube containing 100 μl of the cell suspension, 10 μl of phycoerythrin (PE)-conjugated anti-CD34, or 10 μl of PE-conjugated IgG1 (BD Bioscience, Franklin Lakes, N.J.) are added. Following a 30 minute incubation at 4° C., cells are washed using cold PBS and resuspended in 0.5 ml PBS.

Human $CD34^+$ cells are sorted using a MoFlo cytometer (Dako-Cytomation, Fort Collins, Colo.) and an I-90 argon laser (emitting at 488 nm, Coherent Inc., Palo Alto, Calif.) for excitation. Forward scatter is used as the triggering parameter. PE fluorescence is detected using a 580/30 band-pass filter. Single cell deposition is performed using a CyClone automated cloner (Dako-Cytomation) in the 0.5 single drop mode. Gating of the cells is based on forward scatter and PE fluorescence. Individual $CD34^+$ cells are plated into each well of a 96-well culture plate with 100 μl of serum-free medium containing 100 ng/ml of stem cell factor (SCF), 100 ng/ml of Flt-3, 100 ng/ml of thrombopoietin (TPO), in the presence or absence of 50 ng/ml of granulocyte-colony stimulating factor (G-CSF).

After five days of culture, each well of the microtiter plate is carefully examined with an inverted microscope (Olympus IX50; Melville, N.Y.) in order to examine growth and plating efficiency of single $CD34^+$ cells. As described above in Example 2, cells in each well are graded based on the number of cells present in the well following the five-day culture. Cloning (plating) efficiency is defined as the number of positive wells (any cells present)÷total wells×100.

To assess heterogeneity of the mtDNA sequences among $CD34^+$ cells from each of the normal umbilical cord blood donors, the 1,121 base pair mtDNA control region in a set of $CD34^+$ clones (clonal populations) is subjected to sequencing analysis.

To prepare for sequencing analysis, each $CD34^+$ clone is harvested from the well into a 1.5 ml microcentrifuge tube by vigorous pipetting and dispensing followed by rinse of the well with 200 μl of PBS. Cells are collected after centrifugation at 300×g for 5 minutes, and then washed with PBS. Cell pellets are stored at −80° C. In order to extract DNA from individual $CD34^+$ clones, each cell pellet is covered with 30 μl of 1×TE buffer and lysed by incubating the cells at 95° C. for 10 minutes, with occasional shaking. The lysate is briefly microfuged and stored at −20° C.

The mtDNA is sequenced with the appropriate primers using the BigDye Terminator v3.0 Ready Reaction kit (Applied Biosystems, Foster City, Calif.) according to the manufacturer's protocol, and then applied to the ABI Prism 3100 Genetic Analyzer (Applied Biosystems). The following oligonucleotide primers are used for sequencing: 5'CAGTGTATTGCTTTGAGGAGG3' (SEQ ID NO: 5),

5'CATCTGGTTCCTACTTCAGGGTC3' (SEQ ID NO: 6),

5'TTAACTCCACCATTAGCACC3' (SEQ ID NO: 7),

5'GCATGGAGAGCTCCCGTGAGTGG3' (SEQ ID NO: 8),

5'CACCCTATTAACCACTCACG3' (SEQ ID NO: 9) and

5'TACATTACTGCCAGCCACCATG3' (SEQ ID NO: 10). The mtDNA sequences experimentally obtained are compared to the 2001 Revised Cambridge Reference Sequence (Andrews et al., *Nat. Genet.* 23:147, 1999; Kogelnik et al., *Nucleic Acids Res.* 26:112, 1998) using the National Center for Biotechnology Information (NCBI) Blast2 program and the database search tool, MitoAnalyzer (National Institute of Standards and Technology, Gaithersburg, Md.), in order to identify polymorphisms and mutations. All automated results are manually confirmed.

Analysis of the mtDNA sequence from the set of $CD34^+$ clonal populations from normal donors is used to determine the number of $CD34^+$ clonal populations of cells possessing at least one mtDNA mutation within the sequenced region of the mtDNA. The mutational frequency of the mtDNA can be determined by calculating the proportion of clonal populations of cells, within the set of clonal populations of cells, having at least one mtDNA mutation.

EXAMPLE 6

MtDNA Heterogeneity in Single Hematopoietic Cells

This example provides a description of one embodiment of measuring the mutational frequency of mtDNA, wherein individual hematopoietic cells are substituted for clonal populations of hematopoietic cells.

To determine the heterogeneity of mtDNA sequences in individual hematopoietic cells (for example, $CD34^+$ cells, granulocytes, monocytes, or macrophages), bone marrow, peripheral blood, or umbilical cord blood specimens are collected from normal donors. Mononuclear cells are separated from other hematopoietic cells by standard Ficoll separation and washed twice in phosphate-buffered saline (PBS). In order to isolate granulocytes, the cells suspended in PBS are adjusted to $2\times10^7$ cells/ml. To each 12×75 mm tube containing 100 μl of the cell suspension, 10 μl of phycoerythrin (PE)-conjugated anti-CD33, or 10 μl of PE-conjugated IgG1 (BD Bioscience, Franklin Lakes, N.J.) are added. Following a 30 minute incubation at 4° C., cells are washed using cold PBS and resuspended in 0.5 ml PBS.

Human granulocytes are sorted using a MoFlo cytometer (Dako-Cytomation, Fort Collins, Colo.) and an I-90 argon laser (emitting at 488 nm, Coherent Inc., Palo Alto, Calif.) for excitation. Forward scatter is used as the triggering parameter. PE fluorescence is detected using a 580/30 band-pass filter. Single cell deposition is performed using a CyClone automated cloner (Dako-Cytomation) in the 0.5 single drop mode. Gating of the cells is based on forward scatter and PE fluorescence. Each individual granulocyte is placed in separate 1.5 ml microcentrifuge tubes and the cells are lysed by any means known to one of skill in the art (for example sonication).

To assess heterogeneity of the mtDNA sequences among a set of granulocytes from normal donors, the 1,121 base pair mtDNA control region (a region known to contain multiple mutational hotspots) in a set of granulocytes is subjected to PCR amplification and sequencing analysis. Nested gene PCR amplification is performed using the following nested primers: outer primer pair 5'-CGCCTACACAATTCTCCGATC-3' (SEQ ID NO: 1) and 5'-ACTTGGGTTAATCGTGTGACC-3' (SEQ ID NO: 2), which amplify the region between nucleotide 15,974 and nucleotide 921 of the human mtDNA genome as represented by the revised Human mtDNA Cambridge Reference sequence (Andrews et al., *Nat. Genet.* 23:147, 1999; Kogelnik et al., *Nucleic Acids Res.* 26:112, 1998), and inner primer pair 5'-TTAACTCCACCATTAGCACC-3' (SEQ ID NO: 3) and 5'-GAAAGGCTAGGACCAAACCTA-3' (SEQ ID NO: 4), which amplify the region between nucleotide 15,971 and nucleotide 670 of the human mtDNA genome as represented by the revised Human mtDNA Cambridge Reference sequence (Andrews et al., *Nat. Genet.* 23:147, 1999; Kogelnik et al., *Nucleic Acids Res.* 26:112, 1998). Amplification of mtDNA is performed with the TaKaRa LA PCR kit (PanVera, Madison, Wis.).

The primary and secondary PCR amplifications are carried out in a DNA thermal cycler 480 (Perkin-Elmer, Foster City, Calif.) under the following amplification conditions: one cycle at 96° C. for 1 minute; 35 cycles at 94° C. for 30 seconds, 52° C. for 50 seconds and 72° C. for 1 minute with a 5-second increase per cycle; one cycle of 72° C. for 5 minutes. Secondary PCR samples are electrophoresed on 1% agarose gels and stained with ethidium bromide to assess the purity and size of DNA fragments, and the samples are subsequently purified using the QIAquick™ PCR purification kit (Qiagen, Valencia, Calif.). As negative controls, reaction mixtures without DNA templates are subjected to PCR amplification. To prevent DNA cross-contamination, special precautions are taken for each procedure of cell isolation, PCR amplification and DNA sequencing.

Purified-PCR products are prepared for sequencing, using the appropriate primers (see Example 3, above), with the BigDye Terminator v3.0 Ready Reaction kit (Applied Biosystems, Foster City, Calif.) according to the manufacturer's protocol, and then applied to the ABI Prism 3100 Genetic Analyzer (Applied Biosystems). Sequencing is performed on an ABI Prism 3100 Genetic Analyzer in both orientations. The resultant mtDNA sequences are compared to the 2001 Human mtDNA Revised Cambridge Reference sequence (Andrews et al., *Nat. Genet.* 23:147, 1999; Kogelnik et al., *Nucleic Acids Res.* 26:112, 1998) using the National Center for Biotechnology Information (NCBI) Blast2 program and the database search tool, MitoAnalyzer (National Institute of Standards and Technology, Gaithersburg, Md.) in order to identify mutations (mtDNA heterogeneity) and polymorphisms. All automated results are manually confirmed.

Analysis of the mtDNA sequence from the set of granulocytes from normal donors is used to determine the number of granulocytes possessing at least one mtDNA mutation within the sequenced region of the mtDNA. The mutational frequency of the mtDNA can be determined by calculating the proportion of cells, within the set of cells, having at least one mtDNA mutation.

EXAMPLE 7

Establishing a Correlation Between MtDNA Mutational Frequency and Circumstances in which Genomic (Nuclear) Mutations are Increased In Vitro This example provides a description of one way in which the effect of mutagenic agents, for example chemotherapeutic drugs and X-rays, is measured in cells such as cultured cell lines and primary cells.

To determine the correlation between mtDNA mutational frequency and circumstances that increase genomic (nuclear) mutations in vitro, hematopoietic cells are obtained from normal (do not have any apparent hematologic disease or symptom) donors, for example a healthy subject that has not been exposed to a mutagen, and mononuclear cells are separated from other hematopoietic cells in the sample, for instance as described in Example 1. The isolated mononuclear cells, in addition to cells from a variety of hematopoietic cell lines, are incubated in the presence or absence of at least one mutagenic agent that is known to cause genomic mutations in vitro. The treated and untreated cells are sorted by single cell deposition into 96 well microtiter plates, using a phycoerythrin anti-CD34 monoclonal antibody, a MoFlo cytometer, and a CyClone automated cloner in the 0.5 single drop mode. The cells are expanded into clonal populations of cells during five days of culture in media containing stem cell factor, Flt-3, thrombopoietin, in the presence or absence of granulocyte-colony stimulating factor (G-CSF). DNA is extracted from the treated and untreated clonal populations of cells, mtDNA and/or genomic DNA are amplified, for instance using the primers described in Example 1, and the amplified DNA is sequenced and compared to the 2001 Human mtDNA Revised Cambridge Reference sequence (Andrews et al., *Nat. Genet.* 23:147, 1999; Kogelnik et al., *Nucleic Acids Res.* 26:112, 1998) using the National Center for Biotechnology Information (NCBI) Blast2 program and the database search tool, MitoAnalyzer (National Institute of Standards and Technology, Gaithersburg, Md.), as described herein.

The mutational frequency of mtDNA or genomic DNA in treated and untreated cells in vitro is examined. For example, the number (or percentage or proportion) of clonal populations with new mutations in mtDNA divided by the total number of clonal populations studied (the set of clonal populations of cells), multiplied by 100, is the mutational frequency of the mtDNA. The mutational frequency of genomic DNA is determined in the same manner. An increase in the mutational frequency of both mtDNA and genomic DNA obtained from the cells treated with the mutagenic agent, compared to the untreated cells, is an indication that the increase in mutational frequency of mtDNA can be correlated to an increase in the mutational frequency of genomic DNA. Thus, mutagenic agents that increase the mutational frequency of mtDNA are expected to increase the mutational frequency of genomic DNA.

EXAMPLE 8

Establishing a Correlation Between an Increase in MtDNA Mutational Frequency and Circumstances in which Genomic (Nuclear) Mutations are Increased In Vivo This example provides a description of one way in which the effect of mutagenic agents on mutational frequency is measured in cells expanded into clonal populations of cells from subjects of different age and/or medical history. For example, bone marrow specimens from children and umbilical cord blood from newborns are collected from normal donors, for example a healthy subject that has not been exposed to a mutagen, for which the prevalence of mtDNA mutations is very low. These specimens are compared to bone marrow specimens obtained from adults. Alternatively, bone marrow is collected from subjects before and after they have undergone cytotoxic chemotherapy or radiation. Bone marrow samples also are collected from subjects with genetic syndromes that are known to result in a high prevalence of mtDNA mutations, for example Pearson's syndrome.

To determine the correlation between mtDNA mutational frequency and circumstances which increase genomic mutations in vivo, mononuclear cells in bone marrow specimens obtained from subjects before and after chemotherapy treatment are separated from other hematopoietic cells in the samples by density gradient centrifugation. $CD34^+$ cells are sorted by single cell deposition into 96 well microtiter plates, using a phycoerythrin anti-CD34 monoclonal antibody, a MoFlo cytometer, and a CyClone automated cloner in the 0.5 single drop mode. After five days of culture in media containing stem cell factor, Flt-3, thrombopoietin, in the presence or absence of granulocyte-colony stimulating factor (G-CSF), each well of the microtiter plate is carefully examined microscopically. DNA is extracted, mtDNA and/or genomic DNA are amplified, for instance using the primers described in Example 1, and the amplified DNA is sequenced and compared to the 2001 Human mtDNA Revised Cambridge Reference sequence (Andrews et al., *Nat. Genet.* 23:147, 1999; Kogelnik et al., *Nucleic Acids Res.* 26:112, 1998) using the National Center for Biotechnology Information (NCBI) Blast2 program and the database search tool, MitoAnalyzer (National Institute of Standards and Technology, Gaithersburg, Md.), as described herein.

The mutational frequency of mtDNA or genomic DNA in chemotherapy-treated and -untreated cells in vivo is examined. For example, the number of clonal populations of cells with new mutations in mtDNA divided by the total number of clonal populations of cells studied (the set of clonal populations of cells), multiplied by 100, is the mutational frequency of the mtDNA. The mutational frequency of genomic DNA is determined in the same manner. An increase in the mutational frequency of both mtDNA and genomic DNA obtained from the chemotherapy-treated cells, compared to the chemotherapy-untreated cells, is an indication that the increase in mutational frequency of mtDNA can be correlated to an increase in the mutational frequency of genomic DNA. Thus, mutagenic agents that increase the mutational frequency of mtDNA in vivo are believed to increase the mutational frequency of genomic DNA in vivo.

EXAMPLE 9

Screening for the Mutagenic Effect of Agents

This example provides a description of one way of screening for agents that have a mutagenic effect on a cell, or screening for the mutagenic effect of agents.

Bone marrow or peripheral blood specimens are collected from normal donors and mononuclear cells are separated from other hematopoietic cells by density gradient centrifugation. $CD34^+$ cells are isolated as described herein and the cells are then cultured either in the presence or absence of a series of known or putative mutagenic agents for various lengths of time. The treated and untreated $CD34^+$ cells are sorted by single cell deposition into 96 well microtiter plates, using a phycoerythrin anti-CD34 monoclonal antibody, a MoFlo cytometer, and a CyClone automated cloner in the 0.5 single drop mode. The cells also can be cultured in media containing stem cell factor, Flt-3, thrombopoietin, in the presence or absence of granulocyte-colony stimulating factor (G-CSF). Following the culture period, each well of the microtiter plate is carefully examined microscopically, as described above in Example 1. DNA is then extracted from the treated and untreated cells, mtDNA and genomic DNA are amplified, for instance using the primers described in Example 1, and the amplified DNA is sequenced. The mutational frequency of mtDNA or genomic DNA in treated cells, compared to the untreated cells, is examined to screen for the mutagenic effect of the agents. An increase in the mutational frequency of mtDNA and/or genomic DNA obtained from treated cells, compared to the mtDNA and/or genomic DNA obtained from untreated cells, is an indication that the agent is a mutagen. In particular examples, the mutational frequency of mtDNA obtained from treated cells is compared to the mutational frequency of mtDNA from untreated cells.

EXAMPLE 10

Tracking a Set of MtDNA Mutations in Subjects Suffering from Disease

This example provides a description of one way to track a set of mtDNA mutations (a profile) in a subject having a disease. The subject's progress in overcoming the disease can be measured by the presence or absence of cells with the mtDNA mutation pattern in the subject following treatment.

To track the mtDNA mutation pattern in subjects undergoing treatment for a disease, bone marrow or peripheral blood is collected from subjects before and after they undergo treatment, for example cytotoxic chemotherapy or radiation. Multiple samples can be taken after or during treatment to track the subject's progress. Blood or bone marrow samples can be obtained from the subject at any time following treatment. Mononuclear cells are separated from other hematopoietic cells in the samples by density gradient centrifugation. $CD34^+$ cells are sorted by single cell deposition into 96 well microtiter plates, using a phycoerythrin anti-CD34 monoclonal antibody, a MoFlo cytometer, and a CyClone automated cloner in the 0.5 single drop mode. After five days of culture in media containing stem cell factor, Flt-3, thrombopoietin, in the presence or absence of G-CSF, each well of the microtiter plate is carefully examined microscopically. DNA is extracted, mtDNA is amplified, for instance using the primers described in Example 1, and the amplified DNA is sequenced. The mtDNA mutation pattern in cells obtained from the subject before and after treatment is examined to determine the effect of the treatment on eradicating the cells with the particular mtDNA mutation profile.

This disclosure provides methods of determining the mutation frequency in a cell, and more particularly in a hematopoietic cell, such as a $CD34^+$ cell or a cell in which the mutation frequency can be correlated to that measured in a $CD34^+$ cell. The disclosure further provides methods of screening various agents for their mutagenic effect on cells. It will be apparent that the precise details of the methods described may be varied or modified without departing from the spirit of the described invention. We claim all such modifications and variations that fall within the scope and spirit of the claims below.

We claim:

1. A method of measuring a mutational frequency of a mitochondrial DNA sequence in a subject, comprising:

isolating hematopoietic cells from the subject, wherein the hematopoietic cells each contain at least one mitochondrion comprising mitochondrial DNA;

separately sequencing the same regions of the mitochondrial DNA from individual, non-clonally expanded hematopoietic cells or from individual, clonal populations of the hematopoietic cells; and determining a proportion of the hematopoietic cells exhibiting mitochondrial DNA heterogeneity within the sequenced regions of the mitochondrial DNA, wherein the proportion corresponds to the mutational frequency of the mitochondrial DNA sequence in the subject.

2. The method of claim 1, wherein determining the proportion of the hematopoietic cells exhibiting mitochondrial DNA heterogeneity within the same regions comprises determining the proportion of clonal populations possessing at least one mitochondrial DNA mutation that distinguishes it from clonal populations with a mitochondrial DNA sequence containing only polymorphisms.

3. The method of claim 1, wherein the mitochondrial DNA is amplified prior to sequencing.

4. The method of claim 2, wherein the mitochondrial DNA from the clonal populations is extracted without amplification prior to sequencing.

5. The method of claim 1, wherein the hematopoietic cells comprise $CD34^+$ cells, granulocytes, monocytes, or macrophages.

6. The method of claim 1, wherein the hematopoietic cells are isolated from bone marrow, peripheral blood, or umbilical cord blood.

7. The method of claim 1, wherein isolating the hematopoietic cells comprises:

obtaining a biological sample from the subject;

contacting hematopoietic cells in the biological sample with a specific binding agent attached to a detectable label; and purifying the hematopoietic cells contacted with the specific binding agent.

8. The method of claim 7, wherein the biological sample comprises bone marrow, peripheral blood, or umbilical cord blood.

9. The method of claim 7, wherein the detectable label comprises a fluorescent agent, a chemiluminescent agent, or a radioisotope.

10. The method of claim 1, wherein the subject is a human.

11. The method of claim 1, wherein the subject has a disease that is or may be associated with a mitochondrial DNA mutation or a non-mitochondrial DNA mutation.

12. The method of claim 1, wherein the subject has been subjected to a mutagenic treatment.

13. The method of claim 12, wherein the mutagenic treatment comprises chemotherapy or radiation.

14. The method of claim 1, wherein the mitochondrial DNA sequence from the hematopoietic cells has at least one mutation that distinguishes it from hematopoietic cells with a mitochondrial DNA sequence containing only polymorphisms, and wherein the mutation is not present in the mitochondrial DNA sequence from a control hematopoietic cell.

15. The method of claim 14, wherein the mutation comprises a point mutation, a polymorphism, a frame-shift mutation, a missense mutation, a nonsense mutation, a silent mutation, or a deletion mutation.

16. The method of claim 14, wherein the mutation is in a homopolymeric C tract of a mitochondrial DNA control region or in a gene in a mitochondrial DNA coding region.

17. A method of measuring a mutational frequency of a mitochondrial DNA sequence in a subject, comprising:

isolating hematopoietic cells from the subject, wherein the hematopoietic cells each contain at least one mitochondrion comprising mitochondrial DNA;

expanding individual hematopoietic cells into individual clonal populations of hematopoietic cells;

extracting mitochondrial DNA from each of the clonal populations of hematopoietic cells;

separately sequencing the same regions of the mitochondrial DNA from each of the clonal populations; and determining a proportion of the clonal populations of hematopoietic cells exhibiting mitochondrial DNA heterogeneity within the sequenced regions of the mitochondrial DNA, wherein the proportion corresponds to the mutational frequency of the mitochondrial DNA sequence in the subject.

18. The method of claim 17, wherein the hematopoietic cells comprise $CD34^+$ cells, granulocytes, monocytes, or macrophages.

19. The method of claim 17, wherein the hematopoietic cells are isolated from bone marrow, peripheral blood, or umbilical cord blood.

20. The method of claim 17, wherein isolating the hematopoietic cells comprises:

obtaining a biological sample from the subject;

contacting hematopoietic cells in the biological sample with a specific binding agent attached to a detectable label; and purifying the hematopoietic cells contacted with the specific binding agent.

21. The method of claim 20, wherein the biological sample comprises bone marrow, peripheral blood, or umbilical cord blood.

22. The method of claim 20, wherein the detectable label comprises a fluorescent agent, a chemiluminescent agent, or a radioisotope.

23. The method of claim 17, wherein the mitochondrial DNA is amplified prior to sequencing.

24. The method of claim 17, wherein the subject is a human.

25. The method of claim 17, wherein the subject has a disease that is or that may be associated with a mitochondrial DNA mutation or a non-mitochondrial DNA mutation.

26. The method of claim 17, wherein the subject has been subjected to a mutagenic treatment.

27. The method of claim 26, wherein the mutagenic treatment comprises chemotherapy or radiation.

28. The method of claim 17, wherein determining the proportion of clonal populations of hematopoietic cells exhibiting mitochondrial heterogeneity within the same regions comprises determining the proportion of clonal populations of hematopoietic cells that has at least one mutation that distinguishes it from clonal populations of hematopoietic cells with a mitochondrial DNA sequence containing only polymorphisms, and wherein the mutation is not present in the mitochondrial DNA sequence from a control clonal population of hematopoietic cells.

29. The method of claim 28, wherein the mutation comprises a point mutation, a polymorphism, a frame-shift mutation, a missense mutation, a nonsense mutation, a silent mutation, or a deletion mutation.

30. The method of claim 28, wherein the mutation is in a homopolymeric C tract of a mitochondrial DNA control region or in a gene in a mitochondrial DNA coding region.

31. A method of estimating a mutational frequency of a genomic DNA sequence in a subject, comprising:

isolating hematopoietic cells from a subject, wherein the hematopoietic cells each contain at least one mitochondrion comprising mitochondrial DNA;

expanding individual hematopoietic cells into individual clonal populations of hematopoietic cells;

extracting mitochondrial DNA from each of the clonal populations of hematopoietic cells;

separately sequencing a region of the mitochondrial DNA from each of the clonal populations;

determining a proportion of the clonal populations of hematopoietic cells exhibiting mitochondrial DNA heterogeneity within the sequenced region; and correlating the proportion exhibiting mitochondrial DNA heterogeneity to an estimated mutational frequency of genomic DNA from the same subject, thereby estimating the mutational frequency of the genomic DNA sequence in the subject.

32. The method of claim 31, wherein the mitochondrial DNA is amplified prior to sequencing.

* * * * *

UNITED STATES PATENT AND TRADEMARK OFFICE

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

On the Cover, Section (56) OTHER PUBLICATIONS:

Page 1, left column, "Gattwemann" should read --Gattermann--.

Page 1, left column, "cytocrome" should read --cytochrome--.

Page 2, right column, "redmodeling" should read --remodeling--.

Page 2, right column, "mitotypingcom" should read --mitotyping.com--.

In the Figures:

Figure 3, "Total DNA extact" should read --Total DNA extract--.

In the Specification:

Column 1, line 15, "(mt DNA)" should read --(mtDNA)--.

Column 2, line 61, "or than an" should read --or that an--.

Column 6, line 13, "(though" should read --(through--.

Column 6, line 55, "antibody, (iv)" should read --antibody; (iv)--.

Column 9, line 1, "Fluorphores" should read --Fluorophores--.

Column 10, line 59, "cell's" should read --cells--.

Column 10, line 61, "of a cells" should read --of cells--.

Column 11, line 30, "B cell" should read --B cells--.

Column 12, line 11, "(HSV)" should read --(HVS)--.

Column 12, line 12, "HSV2" should read --HVS2--.

Column 12, line 45, "H-stand" should read --H-strand--.

Column 14, line 13, "cytopalsm" should read --cytoplasm--.

Column 15, line 2, "cell" should read --cells--.

Column 16, line 21, "tumor of different" should read --tumors of different--.

UNITED STATES PATENT AND TRADEMARK OFFICE

CERTIFICATE OF CORRECTION

PATENT NO. : 7,255,993 B2 
APPLICATION NO. : 10/704283
DATED : August 14, 2007
INVENTOR(S) : Young et al.

It is certified that error appears in the above-identified patent and that said Letters Patent is hereby corrected as shown below:

Column 20, line 67, “distinguishes it” should read --distinguishes them--.

Column 21, line 4, “distinguishes it” should read --distinguishes them--.

Column 21, line 19, “granuloctyes” should read --granulocytes--.

Column 23, line 61, “*Brain Res. Brain Res. Protoc.*,” should read --*Brain Res. Protoc.*,--.

Column 24, line 23, “*Biohphys.*” should read --*Biophys.*--.

Column 25, line 17, “pCR®02.1” should read --pCR® 2.1--.

Column 26, line 43, “1995)” should read --1995).--.

Column 29, line 59 (in Table 2), “A73G HV1 + 7S” should read --A73G HV2 + 7S--.

Column 30, line 15 (in Table 2), “A263C” should read --A263G--.

Column 30, line 11 (in Table 2), “A73G HV1 + 7S” should read --A73G HV2 + 7S--.

Column 35, line 4 (in Table 5), “b ne m rr w” should read --bone marrow--.

Column 36, line 4 (in Table 5), “b ne m rr w” should read --bone marrow--.

Column 36, line 55, “TI61 C/T” should read --TI61C/T--.

Column 38, line 36, “16, 193” should read --16,193--.

Column 39, line 28 (in Table 7), “A263C” should read --A263G--.

Column 46, line 40, “110 µl” should read --10 µl--.

Column 46, line 67, “CD34+ clones” should read --$CD34^+$ clones--.

Column 49, below Table 14, “planting efficiency” should read --plating efficiency--.

Column 53, Table 15 (sub-Column A), “ins 514CA*” should read --$ins514CA^{\#}$--.

Column 54, Table 15 (sub-Column C), “+16093T*” should read --$+16093T^{S}$--.

UNITED STATES PATENT AND TRADEMARK OFFICE

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Column 55, Table 15 (sub-Column A), "ins 514CA" should read --ins514CA$^{S}$--.

Column 55, Table 15 (sub-Column A), "ins 514CA*" should read --ins514CA$^{\#}$--.

Column 55, Table 15 (sub-Column A), "ins 514CA$^{5}$" should read --ins514CA$^{S}$--.

Column 55, Table 15 (sub-Column A), "ins 514CA$^{5}$" should read --ins 514CA$^{S}$--.

Column 56, Table 15 (sub-Column B), "+ins 515GA$^{5}$" should read --"+ins 515CA$^{S}$--.

Column 56, Table 15 (sub-Column B), "ins 514CA$^{5}$" should read --ins514CA$^{S}$--.

Column 56, Table 15 (sub-Column B), "ins 514$^{5}$." should read --ins 514$^{S}$--.

Column 56, Table 15 (sub-Column C), "+16093T$^{*}$." should read --+16093T$^{S}$--.

Column 57, below Table 15, "sequence, Unique" should read --sequence; Unique--.

Column 59, Table 17 (sub-Column A), the second occurrence of "His TS" should be omitted from the patent.

Column 59, Table 17 (sub-Column A), the second occurrence of "Asp TV" should be omitted from the patent.

Column 59, Table 17 (sub-Column A), the second occurrence of "Ala TS" should be omitted from the patent.

Column 59, Table 17 (sub-Column A), "+7022T" should read --+7022T$^{S}$--.

Column 59, Table 17 (sub-Column A), "+15607A" should read --+15607A$^{S}$--.

Column 60, Table 17 (sub-Column B), "+T1506T/C" should read --+T15067T/C--.

UNITED STATES PATENT AND TRADEMARK OFFICE

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

With regard to Several Tables in the Specification:

In addition to the text errors detailed above, the formatting of several tables is incorrect in the issued patent, particularly with regard to alignment of cells. (see attached page)

Signed and Sealed this

Seventeenth Day of November, 2009

David J. Kappos

David J. Kappos
*Director of the United States Patent and Trademark Office*

UNITED STATES PATENT AND TRADEMARK OFFICE

CERTIFICATE OF CORRECTION

PATENT NO. : 7,255,993 B2 
APPLICATION NO. : 10/704283
DATED : August 14, 2007
INVENTOR(S) : Young et al.

It is certified that error appears in the above-identified patent and that said Letters Patent is hereby corrected as shown below:

Col. 29, Lines 49 - Col. 30, Lines 1-57, Table 2 should read

Table 2. Nucleotide sequence changes of mtDNA control region from total bone marrow cells.

--

| Donor (Age/Sex) | Polymorphism (Mutation) | Affected mtDNA gene | Donor (Age/Sex) | Polymorphism (Mutation) | Affected mtDNA gene |
|---|---|---|---|---|---|
| 1 (47/F) | C150T | HV2 + 7S + OH | 4 (34/M) | G247A | HV2 + TFB1 |
| | A263G | HV2 + OH | | A263G | HV2 + OH |
| | 8C/6C* | HV2 + OH + CSB2 | | del C 514 | |
| | C16,192T | HV1 + 7S | | del A 515 | |
| | C16,270T | HV1 + 7S | | T16,093C | HV1 |
| 2 (38/F) | A73G | HV2 + 7S | | G16,129A | HV1 + 7S |
| | G185A | HV2 + 7S + OH | | C16,148T | HV1 + 7S |
| | A263G | HV2 + OH | | C16,168T | HV1 + 7S + TAS |
| | 7C/6C* | HV2 + OH + CSB2 | | T16,172C | HV1 + 7S + TAS |
| | (A478G) | | | C16,187T | HV1 + 7S |
| | T16,093C | HV1 | | C16,188G | HV1 + 7S |
| | A16,158G | HV1 + TAS | | T16,189C | HV1 + 7S |
| | T16,172C | HV1 + TAS | | C16,223T | HV1 + 7S |
| | A16,183C | HV1 + 7S | | A16,230G | HV1 + 7S |
| | T16,189C | HV1 + 7S | | C16,278T | HV1 + 7S |
| | A16,219G | HV1 + 7S | | A16,293G | HV1 + 7S |
| | C16,278T | HV1 + 7S | | T16,311C | HV1 + 7S |
| 3 (43/M) | A73G | HV2 + 7S | | C16,320T | HV1 + 7S |
| | T146C | HV2 + 7S + OH | 5 (54/M) | A73G | HV2 + 7S |
| | T152C | HV2 + 7S + OH | | A263G | HV2 + OH |
| | T195C | HV2 + OH | | 7C/6C | HV2 + OH + CSB2 |
| | A263G | HV2 + OH | | del 514C | |
| | 9C/6C | HV2 + OH + CSB2 | | del 515A | |
| | del 514 C | | | T16,126C | HV1 + 7S |
| | del 515 A | | | C16,294T | HV1 + 7S |
| | C16,223T | HV1 + 7S | | C16,296T | HV1 + 7S |
| | C16,278T | HV1 + 7S | | T16,519C | 7S |
| | C16,294T | HV1 + 7S | 6 (34/F) | A73G | HV2 + 7S |
| | G16,390A | 7S | | C150T | HV2 + 7S + OH |
| 4 (34/M) | A93G | HV2 + 7S | | A263G | HV2 + OH |
| | A95C | HV2 + 7S | | 8C/6C | HV2 + OH + CSB2 |
| | G185A | HV2 + 7S + OH | | (A517G) | |
| | A189G | HV2 + 7S + OH | | C16,270T | HV1 + 7S |
| | T236C | HV2 + OH | | C16,292T | HV1 + 7S |
| | 8C/6C | HV2 + OH + CSB2 | | T16,362C | HV1 + 7S |

--.

UNITED STATES PATENT AND TRADEMARK OFFICE
CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Col. 33, Lines 10-25, Table 4 should read

-- Table 4. The number of $CD34^+$ clones from bone marrow subjected to mtDNA sequencing analysis.

| Donor | 1 | | 2 | | 3 | | 4 | | 5 | | 6 | | Total No. |
|---|---|---|---|---|---|---|---|---|---|---|---|---|---|
| Grade \ G-CSF | + | - | + | - | + | - | + | - | + | - | + | - | |
| 1 | 14 | 14 | 13 | 10 | 15 | 15 | 13 | 13 | 12 | 14 | 14 | 11 | 158 |
| 2 | 8 | 12 | 1 | 2 | 15 | 15 | 14 | 14 | 15 | 13 | 15 | 15 | 139 |
| 3 | 16 | 14 | 1 | 3 | 15 | 15 | 15 | 13 | 15 | 15 | 15 | 15 | 152 |
| 4 | 35 | 2 | 6 | 0 | 25 | 5 | 15 | 14 | 25 | 5 | 15 | 15 | 162 |
| Subtotal No. | 73 | 42 | 21 | 15 | 70 | 50 | 57 | 54 | 67 | 47 | 59 | 56 | 611 |
| Total No. | 115 | | 36 | | 120 | | 111 | | 114 | | 115 | | |

--.

UNITED STATES PATENT AND TRADEMARK OFFICE
CERTIFICATE OF CORRECTION

PATENT NO. : 7,255,993 B2 
APPLICATION NO. : 10/704283
DATED : August 14, 2007
INVENTOR(S) : Young et al.

It is certified that error appears in the above-identified patent and that said Letters Patent is hereby corrected as shown below:

Col. 35, Lines 1 - Col. 36, Lines 1-22, Table 5 should read

Table 5. Summary of mtDNA heterogeneity among single CD34$^+$ clones from bone marrow

--

| Donor/Heteroplasmy pattern | | mtDNA gene | No. Clone | No. Total | % | Donor / Heteroplasmy pattern | | mtDNA gene | No. Clone | No. Total | % |
|---|---|---|---|---|---|---|---|---|---|---|---|
| | BM poly alone | | 85 | 85 | 73.9 | | + 7C/6C*+8C/6C* | HV2, OH, CSB2 | 2 | | |
| | + 8C/6C*+9C/6C | HV2, OH, CSB2 | 22 | | | | + 9C/6C*+10C/6C* | HV2, OH, CSB2 | 1 | | |
| | + 9C/6C* | HV2, OH, CSB2 | 2 | | | | + T89C | HV2, 7S | 1 | 16 | 14.4 |
| | + 7C/6C* | HV2, OH, CSB2 | 1 | | | 4 | + 8C/6C*+9C/6C* | HV2, OH, CSB2 | 1 | | |
| | + A189G/A | HV2, OH, 7S | 1 | | | | 16,093T | HV1 | | | |
| 1 | + T204C | HV2, OH | 1 | 30 | 26.1 | | Subtotal | | 111 | 111 | 100.0 |
| | + C277T | HV2, OH, TFB1 | 1 | | | | BM poly alone | | 62 | 62 | 54.4 |
| | + C514CAC | | 1 | | | | + 514C, 515A | | 19 | | |
| | + C16,114T | HV1, 7S | 1 | | | | + C264T | HV2, OH | 18 | | |
| | Subtotal | | 115 | 115 | 100.0 | | + C264T/C | HV2, OH | 3 | | |
| | BM poly alone | | 33 | 33 | 91.7 | | + 7C/6C*+8C/6C* | HV2, OH, CSB2 | 2 | | |
| | + T16,131C/T | HV1, 7S | 1 | | | | + T146C | HV2, OH, 7S | 2 | | |
| | + G16,145A | HV1, 7S | 1 | | | | 514C, 515A | | | | |
| | A191AA | HV2, OH, 7S | | | | | + T146C | HV2, OH, 7S | 1 | | |
| | C194T | HV2, OH | | | | | C264T/C | HV2, OH | | | |
| | T199C | HV2, OH | | | | | + T146C/T | HV2, OH, 7S | 1 | | |
| | G207A | HV2, OH | | | | 5 | 514C, 515A | | | 52 | 45.6 |
| 2 | A73G, 8C/6C* | HV2, OH, CSB2 | | 3 | 8.3 | | + T146C | HV2, OH, 7S | 1 | | |
| | A263G T489C | | 1 | | | | + A189G | HV2, OH, 7S | 1 | | |
| | C16,147T | HV1, 7S | | | | | + C264T/C | HV2, OH | 1 | | |
| | C16,173T | HV1, 7S | | | | | 514C, 515A | | | | |
| | C16,245T | HV1, 7S | | | | | + T161C/T | HV2, OH, 7S | | | |
| | T16,362C | HV1, 7S | | | | | C264T | HV2, OH | 1 | | |
| | Subtotal | | 36 | 36 | 100.0 | | 514C, 515A | | | | |
| | BM poly alone | | 96 | 96 | 80.0 | | + T16,189C | HV1, 7S | 1 | | |
| | + 9C/6C*+10C/6C* | HV2, OH, CSB2 | 11 | | | | + C16,296C/T | HV1 | 1 | | |
| | + 8C/6C*+9C/6C* | HV2, OH, CSB2 | 6 | | | | Subtotal | | 114 | 114 | 100.0 |
| | + 8C/6C* | HV2, OH, CSH2 | 2 | | | | BM poly alone | | 102 | 102 | 88.7 |
| | + C182T/C | HV2, OH, 7S | 2 | | | | + 8C/6C*+9C/6C* | HV2, OH, CSB2 | 5 | | |
| 3 | 8C/6C*+9C/6C* | HV2, OH, CSB2 | | 24 | 20.0 | | + A200G/A | HV2, OH | 3 | | |
| | + del 71G | HV2, 7S | 1 | | | | + A200G | HV2, OH | 2 | | |
| | 9C/6C*+10C/6C* | HV2, OH, CSB2 | | | | 6 | + A200G/A | HV2, OH | 1 | 13 | 11.3 |
| | + T279C/T | HV2, OH, TFB1 | 1 | | | | 7C/6C*+8C/6C* | HV2, OH, CSB2 | | | |
| | + G16,153A | HV1, 7S | 1 | | | | + A200G/A | HV2, OH | 1 | | |
| | Subtotal | | 120 | 120 | 100.0 | | 8C/6C*+9C/6C* | HV2, OH, CSB2 | | | |
| 4 | BM poly alone | | 95 | 95 | 85.6 | | + 7C/6C*+8C/6C* | HV2, OH, CSB2 | 1 | | |
| | + 8C/6C*+9C/6C* | HV2, OH, CSB2 | 11 | | | | Subtotal | | 115 | 115 | 100.0 |
| No and % of CD34$^+$ clones having 'the same as total BM polymorphism alone' (77.4±13.6 %, mean±SD) | | | | | | | | | | 473 | 77.4 |
| No and % of CD34$^+$ clones showing 'mtDNA heterogeneity' (**22.6±13.6** %, mean±SD) | | | | | | | | | | **138** | **22.6** |
| Total No of assayed CD34$^+$ clones | | | | | | | | | | 611 | 100.0 |

--.

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Col. 43, Lines 1-39, Table 10 should read

--

Table 10. Summary of mtDNA heterogeneity among single CD34$^+$ clones derived from cord blood

| CB donor | Heteroplasmy pattern | | No. of clones | Total | % |
|---|---|---|---|---|---|
| 1 | BM poly (+) alone | | 118 | 118 | 99.2 |
| | A73G<br>A263G<br>7C/6C<br>del 514-515CA<br>C16,223T<br>C16,354T<br>T16,519C | A153G<br>A183G<br>8C/6C<br>C325T<br>C463T<br>T485C<br>T489C<br>T16,198C<br>C16,268T<br>T16,381A | 1 | 1 | 0.8 |
| | Subtotal | | 119 | 119 | 100 |
| 2 | BM poly (+) alone | | 120 | 120 | 100.0 |
| | Subtotal | | 120 | 120 | 100.0 |
| 3 | BM poly (+) alone | | 100 | 100 | 96.2 |
| | + G316G/C | | 3 | 4 | 3.8 |
| | + CCC305-307CCC/AAA | | 1 | | |
| | Subtotal | | 104 | 104 | 100 |
| 4 | BM poly (+) alone | | 118 | 118 | 99.2 |
| | + 6C/6C<br>+ T16,022C | | 1 | 1 | 0.8 |
| | Subtotal | | 119 | 119 | 100.00 |
| 5 | BM poly (+) alone | | 114 | 114 | 97.4 |
| | + C16,193CCC (12C) | | 1 | 3 | 2.6 |
| | + del 16,189T | | 1 | | |
| | + C16,193CCCC (13C) | | 1 | | |
| | Subtotal | | 117 | 117 | 100.0 |
| Total (summary) | BM poly (+) alone | | 571 | 571 | 98.1 |
| | Total No. of heterogeneity | | 9 | 9 | 1.6 |
| | Unique heterogeneity | | | 7 | 1.2 |
| | | | 580 | 580 | 580 |

Abbreviations: BM poly, mtDNA polymorphism from total bone marrow cells; +, mtDNA nucleotide changes in addition to the polymorphisms detected in the respective bulk mtDNA; *, poly C tract localized between np 303 and np 315.

--.

Col. 43, Lines 56 - Col. 44, Lines 1-14, Table 11 should read

--

Table 11. Comparison of characteristics between CD34$^+$ clones derived from adult bone marrow and umbilical cord blood.

| | Adult BM CD34$^+$ | Cord Blood CD34$^+$ |
|---|---|---|
| Plating Efficiency | 30% | 78.6%* |
| Bulk cell analysis | Uniform pattern | Frequently heteroplasmic |
| Heteroplasmy | | |
| Total rate | 22.6% | 1.6% |
| Unique pattern | 8.6% | 1.2% |
| Substitution (S) | 10.6% (65/611) | 0.0% (0/580) |
| Poly C tract # | 10.8% (66/611) | 1.1% (7/580) |
| S+C | 1.1% (7/611) | 0.3% (2/580) |

statistically significant difference ($P<0.05$); *, mtDNA nucleotide sequence position at 303-315 and 16,183-16,193.

--.

UNITED STATES PATENT AND TRADEMARK OFFICE
CERTIFICATE OF CORRECTION

PATENT NO. : 7,255,993 B2 
APPLICATION NO. : 10/704283
DATED : August 14, 2007
INVENTOR(S) : Young et al.

It is certified that error appears in the above-identified patent and that said Letters Patent is hereby corrected as shown below:

Col. 47, Lines 56 - Col. 48, Lines 1-67, Table 13 should read

-- Table 13. Nucleotide sequence changes of mtDNA control region (A) and coding region (B) from total (bulk) bone marrow cells

A. Control region

| Donors (Age/Sex) | Polymorphism | Affected mtDNA gene | Donors (Age/Sex) | Polymorphism | Affected mtDNA gene |
|---|---|---|---|---|---|
| 1 (47/F) | A73G | *HV2, 7S* | 4 (34/M) | G247A | *HV2, OH, TFB1* |
| | C150T | *HV2, 7S, OH* | | A263G | *HV2, OH* |
| | A263G | *HV2, OH* | | del C 514 | |
| | 8CT6C* | *HV2, OH, CSB2* | | del A 515 | |
| | C16,192T | *HV1, 7S* | | T16,093C | *HV1* |
| | C16,270T | *HV1, 7S* | | G16,129A | *HV1, 7S* |
| 2 (38/F) | A73G | *HV2, 7S* | | C16,148T | *HV1, 7S* |
| | G185A | *HV2, 7S, OH* | | C16,168T | *HV1, 7S, TAS* |
| | A263G | *HV2 + OH* | | T16,172C | *HV1, 7S, TAS* |
| | 7CT6C* | *HV2, OH, CSB2* | | C16,187T | *HV1, 7S* |
| | **A478G**# | | | C16,188G | *HV1, 7S* |
| | T16,093C | *HV1* | | T16,189C | *HV1, 7S* |
| | A16,158G | *HV1, 7S, TAS* | | C16,223T | *HV1, 7S* |
| | T16,172C | *HV1, 7S, TAS* | | A16,230G | *HV1, 7S* |
| | A16,183C | *HV1, 7S* | | C16,278T | *HV1, 7S* |
| | T16,189C (12C) | *HV1, 7S* | | A16,293G | *HV1, 7S* |
| | A16,219G | *HV1, 7S* | | T16,311C | *HV1, 7S* |
| | C16,278T | *HV1, 7S* | | C16,320T | *HV1, 7S* |
| 3 (43/M) | A73G | *HV2, 7S* | | | |
| | T146C | *HV2, 7S, OH* | 5 (54/M) | A73G | *HV2, 7S* |
| | T152C | *HV2, 7S, OH* | | A263G | *HV2, OH* |
| | T195C | *HV2, OH* | | 7CT6C* | *HV2, OH, CSB2* |
| | A263G | *HV2, OH* | | del 514C | |
| | 9CT6C*, 8CT6C* | *HV2 + OH + CSB2* | | del 515A | |
| | del 514 C | | | T16,126C | *HV1, 7S* |
| | del 515 A | | | C16,294T | *HV1, OH* |
| | C16,223T | *HV1, 7S* | | C16,296T | *HV1, OH* |
| | C16,278T | *HV1, 7S* | | T16,519C | *7S* |
| | C16,294T | *HV1, 7S* | | | |
| | G16,390A | *7S* | 6 (34/F) | A73G | *HV2, 7S* |
| | | | | C150T | *HV2, 7S, OH* |
| 4 (34/M) | A93G | *HV2, 7S* | | A263G | *HV2, OH* |
| | A95C | *HV2, 7S* | | 8CT6C* | *HV2, OH, CSB2* |
| | G185A | *HV2, 7S, OH* | | **A517G**# | |
| | A189G | *HV2, 7S, OH* | | C16,270T | *HV1, 7S* |
| | T236C | *HV2, OH* | | C16,292T | *HV1, 7S* |
| | 8CT6C* | *HV2, OH, CSB2* | | T16,362C | *HV1, 7S* |

--.

UNITED STATES PATENT AND TRADEMARK OFFICE
CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Col. 49, Lines 1-29, Table 13 continued should read

-- B. coding region (CO1 and Cytb)

| Donors (Age/Sex) | MtDNA gene | Nucleotide change | Amino acid change | Polymorphism (P) /Mutation (M) |
|---|---|---|---|---|
| 1 (47/F) | CO1 | C7028T | No | P |
| | Cytb | A15326G | Thr -Ala | P |
| 3 (43/M) | CO1 | A6663G | Ile - Val | P |
| | CO1 | C7028T | No | P |
| | CO1 | T7175C | No | P |
| | CO1 | C7256T | No | P |
| | CO1 | C7274T | No | P |
| | Cytb | G15301A | No | P |
| | Cytb | A15326G | Thr -Ala | P |
| | Cytb | T15784C# | No | M |
| 5 (54/M) | CO1 | T7022C# | No | M |
| | CO1 | C7028T | No | P |
| | Cytb | C14766T | No | P |
| | Cytb | G14905A | No | P |
| | Cytb | A15326G | Thr -Ala | P |
| | Cytb | C15452A | Leu - Ile | P |
| | Cytb | A15607G | No | P |

Abbreviations: HV1, hypervariable segment 1; HV2, hypervariable segment 2; 7S, 7S DNA; OH, H-strand origin; CSB2, conserved sequence block II; TAS, termination-association sequence; TFB1, mitochondrial transcription factor 1 binding site; *, homopolymeric C tract localized between nucleotide 303 and 315 (for example, 8CT6C defined CCCCCCCCTCCCCCC); #, new mtDNA polymorphisms (not listed in accepted database); Ala, alanine; Ile, isoleucine; Leu, leucine; Thr, threonine; Val, valine. --.

CERTIFICATE OF CORRECTION

PATENT NO. : 7,255,993 B2

APPLICATION NO. : 10/704283
DATED : August 14, 2007
INVENTOR(S) : Young et al.

It is certified that error appears in the above-identified patent and that said Letters Patent is hereby corrected as shown below:

Col. 49 and 50, Lines 35-67; Col. 51 and 52, Lines 1-32, Table 14 continued should read

--Table 14. $CD34^+$ clones from peripheral blood and bone marrow, and single granulocyte for mtDNA analysis

A. Plating efficiency and grade of $CD34^+$ clones after 5 day-suspension culture, and nested mtDNA PCR efficiency from single granulocytes

| Samples / Donor | PB $CD34^+$ clone | | | | | | | BM $CD34^+$ clone | | | | | | | Single granulocyte mtDNA PCR | | |
|---|---|---|---|---|---|---|---|---|---|---|---|---|---|---|---|---|---|
| | Grade | | | | Subtotal | Microplate* | PEf (%) | Grade | | | | Subtotal | Microplate | PEf (%) | Granulocyte No | PCR efficiency | |
| | 1 | 2 | 3 | 4 | | | | 1 | 2 | 3 | 4 | | | | | Positive No | % |
| 1 (47/F) | 13 | 54 | 128 | 85 | 280 | 5 | 58.3 | 33 | 21 | 30 | 38 | 122 | 4 | 31.8 | 480 | 51 | 10.6 |
| 2 (38/F) | 33 | 61 | 64 | 34 | 192 | 4 | 50.0 | - | - | - | - | - | - | - | 1440 | 37 | 2.6 |
| 3 (43/M) | 24 | 20 | 23 | 26 | 93 | 3 | 32.3 | 279 | 149 | 91 | 127 | 646 | 20 | 33.6 | 480 | 50 | 10.4 |
| 4 (34/M) | 38 | 38 | 58 | 66 | 200 | 5 | 41.7 | - | - | - | - | - | - | - | 768 | 111 | 14.5 |
| 5 (54/M) | 35 | 50 | 61 | 36 | 182 | 5 | 37.9 | 306 | 177 | 119 | 140 | 742 | 20 | 38.6 | 768 | 42 | 5.5 |
| 6 (34/F) | 37 | 46 | 52 | 92 | 227 | 5 | 47.3 | - | - | - | - | - | - | - | 768 | 64 | 8.3 |
| Total | 180 | 269 | 386 | 339 | 1174 | 27 | 45.3 | 618 | 347 | 240 | 305 | 1510 | 44 | 35.7 | 4704 | 355 | 7.5 |

Abbreviations: PB, peripheral blood; BM, bone marrow; suspension culture media containing 100 ng/ml of each stem cell factor (SCF), Flt-3 and thrombopoietin (TPO), free-serum media and 50 ng/ml of G-CSF, PEf, plating efficiency, grade 1, less than 5 cells/well; grade 2, 6 to10 cells/well; grade 3, 11 to 20 cells/well; grade 4, more than 21 cells/well; *, No of 96 well microplates.

B. Assay number

| MtDNA / Donor | Control region | | | | | | | | | | | Coding region (CO1 and Cytb) | | | | | | | | | |
|---|---|---|---|---|---|---|---|---|---|---|---|---|---|---|---|---|---|---|---|---|---|
| | BM $CD34^+$ clone | | | | | PB $CD34^+$ clone | | | | | Single granulocyte | BM $CD34^+$ clone | | | | | PB $CD34^+$ clone | | | | |
| | G1 | G2 | G3 | G4 | Subtotal | G1 | G2 | G3 | G4 | Subtotal | | G1 | G2 | G3 | G4 | Subtotal | G1 | G2 | G3 | G4 | Subtotal |
| 1 (47/F) | 28 | 20 | 30 | 37 | 115 | 13 | 30 | 47 | 30 | 120 | 51 | 29 | 20 | 29 | 18 | 96 | 13 | 30 | 35 | 18 | 96 |
| 2 (38/F) | 23 | 3 | 4 | 6 | 36 | 23 | 24 | 23 | 24 | 94 | 37 | - | - | - | - | - | - | - | - | - | - |
| 3 (43/M) | 30 | 30 | 30 | 30 | 120 | 24 | 20 | 23 | 26 | 93 | 50 | 26 | 26 | 24 | 20 | 96 | 24 | 20 | 23 | 26 | 93 |
| 4 (34/M) | 26 | 28 | 28 | 29 | 111 | 24 | 24 | 24 | 24 | 96 | 111 | - | - | - | - | - | - | - | - | - | - |
| 5 (54/M) | 26 | 28 | 30 | 30 | 114 | 24 | 23 | 24 | 24 | 95 | 42 | 25 | 29 | 30 | 12 | 96 | 24 | 24 | 24 | 24 | 96 |
| 6 (34/F) | 25 | 30 | 30 | 30 | 115 | 24 | 24 | 24 | 24 | 96 | 64 | - | - | - | - | - | - | - | - | - | - |
| Total | 158 | 139 | 152 | 162 | 611 | 133 | 146 | 166 | 152 | 594 | 355 | 80 | 75 | 83 | 50 | 288 | 61 | 74 | 82 | 68 | 285 |

Abbreviations: G, grade; CO1, cytochrome c oxidase 1; Cytb, cytochrome b

--.

UNITED STATES PATENT AND TRADEMARK OFFICE
CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Col. 51 and 52, Lines 35-67; Col. 53 and 54, Lines 1-67; Col. 55 and 56, Lines 1-67; Col. 57 and 58, Lines 1-34, Table 15 should read

--

Table 15. Mutational spectra of mtDNA control region in individual CD34 clones and single granulocytes

A. BM CD34 clones | B. PB CD34 clones | C. single granulocyte

| Donor | A. MtDNA sequence | Clone No | Heterogeneity Frequency No | % | Unique No | % | B. MtDNA sequence | Clone No | Heterogeneity Frequency No | % | Unique No | % | C. MtDNA sequence | Clone No | Heterogeneity Frequency No | % | Unique No | % |
|---|---|---|---|---|---|---|---|---|---|---|---|---|---|---|---|---|---|---|
| | bulk sequence | 85 | | | | | bulk sequence | 90 | | | | | bulk sequence | 40 | | | | |
| | + 8CT6C*, 9CT6C* | 22 | | | | | + 8CT6C*, 9CT6C* | 23 | | | | | | | | | | 9.8 |
| | + 9CT6C* | 2 | | | | | + 9CT6C*, 10CT6C* | 4 | | | | | + 9CT6C*, 10CT6C* | 7 | | | | |
| | + 7CT6C* | 1 | | | | | | | | | | | + 7CT6C* | 1 | | | | |
| 1 (47/F) | + A189G/A | 1 | 30 | 26.1 | 8 | 7.0 | + G16129A/G | 1 | 30 | 25.0 | 5 | 4.2 | + 10CT6C*, 11CT6C | 1 | 11 | 21.6 | 5 | |
| | + T204C | 1 | | | | | + G16129A | 1 | | | | | + C349T/C(M), A368G(M) | 1 | | | | |
| | + C277T | 1 | | | | | + C16256T/C | 1 | | | | | + C369T (M) | 1 | | | | |
| | + ins 514CA | 1 | | | | | | | | | | | | | | | | |
| | + C16114T | 1 | | | | | | | | | | | | | | | | |
| | Subtotal | 115 | | | | | Subtotal | 120 | | | | | Subtotal | 51 | | | | |
| | bulk sequence | 27 | | | | | bulk sequence | 85 | | | | | bulk sequence | 24 | | | | |
| | + C16184CC (11C) | 5 | | | | | + C16184CC (11C) | 5 | | | | | + C16184CC (11C) | 11 | | | | |
| | + T16131C/T | 1 | | | | | + C16184CCCC (13C) | 3 | | | | | + C16184CCCC (13C) | 1 | | | | |
| | + G16145A | 1 | | | | | + A478G/A | 1 | | | | | + C16459T (M) | 1 | | | | |
| 2 (38/F) | + C16184CCCC (13C) | 1 | 9 | 25.0 | 5 | 13.9 | | | 9 | 9.6 | 3 | 3.2 | | | 13 | 35.1 | 3 | 8.1 |
| | A73G, A263G, A191AA, C194T, T199C, G207A, 8CT6C*, T489C, C16147T, C16173T, C16245T, T16362C | 1 | | | | | | | | | | | | | | | | |
| | Subtotal | 36 | | | | | Subtotal | 94 | | | | | Subtotal | 37 | | | | |

- continued -

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Table 15 continued

| | | | | | | | | | | | | | | | | | | |
|---|---|---|---|---|---|---|---|---|---|---|---|---|---|---|---|---|---|---|
| 3 (43/M) | 'bulk' sequence | 96 | | | | | 'bulk' sequence | 66 | | | | | 'bulk' sequence | 34 | | | | |
| | +9CT6C*,10CT6C* | 11 | 24 | 20.0 | 7 | 5.8 | +9CT6C*, 10CT5C* | 26 | 27 | 29.0 | 3 | 3.2 | +9CT6C*, 10CT6C* | 4 | 16 | 32.0 | 10 | 20.0 |
| | +9CT6C* | 6 | | | | | | | | | | | +8CT6C* | 5 | | | | |
| | +8CT6C* | 2 | | | | | +8CT6C*, 9CT6C*, T16124C/T | 1 | | | | | | | | | | |
| | +C182T/C,8CT6C*,9CT6C* | 2 | | | | | | | | | | | +8CT6C*,9CT6C*, C104T(M) | 1 | | | | |
| | +del 71G,9CT6C*,10CT6C* | 1 | | | | | | | | | | | +8CT6C*,9CT6C*, A181A/G(M) | 1 | | | | |
| | +T279C/T | 1 | | | | | | | | | | | +8CT6C*,9CT6C*, C296C/T(M) | 1 | | | | |
| | +G16153A | 1 | | | | | | | | | | | +8CT6C*,9CT6C*, C16339T(M) | 1 | | | | |
| | | | | | | | | | | | | | +8CT6C*,9CT6C*, T16352T/C | 1 | | | | |
| | | | | | | | | | | | | | +9CT6C*, 10CT6C*, G225A, T16263C | 1 | | | | |
| | | | | | | | | | | | | | +8CT6C*,9CT6C*, G16035A | 1 | | | | |
| | Subtotal | 120 | | | | | Subtotal | 93 | | | | | Subtotal | 50 | | | | |
| 4 (34/M) | 'bulk' sequence | 92 | | | | | 'bulk' sequence | 70 | | | | | 'bulk' sequence | 77 | | | | |
| | +8CT6C*,9CT6C* | 11 | 19 | 17.4 | 6 | 5.4 | +8CT6C*, 9CT6C* | 16 | 25 | 263 | 5 | 5.3 | +8CT6C*,9CT6C* | 6 | 34 | 30.6 | 16 | 14.4 |
| | +del514-515CA, ins 514CA | 3 | | | | | +7CT6C*, 8CT6C* | 3 | | | | | +7CT6C*, 8CT6C* | 3 | | | | |
| | +7CT6C*,9CT6C* | 2 | | | | | +T16093T/C | 4 | | | | | +9CT6C*, 10CT6C* | 6 | | | | |
| | +9CT6C*,10CT6C* | 1 | | | | | +8CT6C*, 9CT6C*, T16044C/T (M) | 1 | | | | | +9CT6C*, 10CT6C*, T16093T/C | 2 | | | | |
| | +T89C | 1 | | | | | +8CT6C*, 8CT7C | 1 | | | | | +T16093T/C | 3 | | | | |
| | +8CT6C*,9CT6C*, T16,093T | 1 | | | | | | | | | | | +16093T | 4 | | | | |
| | | | | | | | | | | | | | +16093T, G16208A (M) | 1 | | | | |
| | | | | | | | | | | | | | +A28 G/A (M) | 1 | | | | |
| | | | | | | | | | | | | | +8CT6C*, 9CT6C, G185G/A | 1 | | | | |
| | | | | | | | | | | | | | +T195T/C | 1 | | | | |
| | | | | | | | | | | | | | +T195C, A16175C (M) | 1 | | | | |
| | | | | | | | | | | | | | +C277T (M) | 1 | | | | |
| | | | | | | | | | | | | | +C315C/T | 1 | | | | |
| | | | | | | | | | | | | | +C411T (M) | 1 | | | | |
| | | | | | | | | | | | | | +del 452T (M) | 1 | | | | |
| | | | | | | | | | | | | | +C469T (M), T16093T/C | 1 | | | | |
| | Subtotal | 111 | | | | | Subtotal | 95 | | | | | Subtotal | 111 | | | | |

- continued -

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Table 15 continued

| | | | | | | | | | | | | | | | | | | |
|---|---|---|---|---|---|---|---|---|---|---|---|---|---|---|---|---|---|---|
| 5 (54/M) | 'bulk' sequence | 57 | | | | | 'bulk' sequence | 63 | | | | | 'bulk' sequence | 22 | | | | |
| | + ins 514CA | 19 | | | | | + ins 514CA | 11 | | | | | + C264T | 7 | | | | |
| | + C264T | 18 | | | | | + C264T | 11 | | | | | + T146C | 1 | | | | |
| | + del514-515CA, ins 514CA | 5 | | | | | + C264T/C | 2 | | | | | + 7CT6C*, 8CT6C* | 1 | | | | |
| | + C264T/C | 3 | | | | | + T146C/T, ins 514CA | 4 | | | | | + 8CT6C | 1 | | | | |
| | + 7CT6C*, 8CT6C* | 2 | | | | | | | | | | | | | | | | |
| | + T146C, 514-515CA | 2 | | | | | + G94A/G | 1 | 33 | 34.4 | 9 | 9.4 | + T321T/C (M) | 1 | | | | |
| | + T146C, C264T/C | 1 | | | | | + C320C/A | 1 | | | | | + A376G (M) | 1 | | | | |
| | + T146C/T, ins 514CA | 1 | 57 | 50.0 | 14 | 12.3 | + T16189C | 1 | | | | | + T582T/C (M), T16075C/T | 1 | 20 | 47.6 | 14 | 33.3 |
| | + T146C | 1 | | | | | + A16265G | 1 | | | | | + T1605C/T (M) | 1 | | | | |
| | + A189G | 1 | | | | | + A357AA (M), ins 514, T16136C/T | 1 | | | | | + A16098A/G | 1 | | | | |
| | + C264T/C, 514-515CA | 1 | | | | | | | | | | | + C16259G | 1 | | | | |
| | + T161C/T, C264T, ins 514CA | 1 | | | | | | | | | | | + G16274A, C16296T/C | 1 | | | | |
| | + T16,189C | 1 | | | | | | | | | | | + C16292T | 1 | | | | |
| | + C16,296C/T | 1 | | | | | | | | | | | + C16332T (M), C16366T | 1 | | | | |
| | | | | | | | | | | | | | + T16422C | 1 | | | | |
| | Sub total | 134 | | | | | Sub total | 96 | | | | | Sub total | 42 | | | | |
| 6 (34/F) | 'bulk' sequence | 102 | | | | | 'bulk' sequence | 69 | | | | | 'bulk' sequence | 55 | | | | |
| | + 5CT6C*, 9CT6C* | 5 | | | | | + 8CT6C*, 9CT6C* | 18 | | | | | + 8CT6C*, 9CT6C* + | 4 | | | | |
| | + A200G/A | 3 | | | | | + A200G/A | 4 | | | | | | | | | | |
| | + A200G | 2 | 13 | 11.3 | 6 | 5.6 | + A200G | 1 | | | | | + A28G (M) | 1 | | | | |
| | + A200G/A, 7CT6C*, 8CT6C* | 1 | | | | | + A200G/A, 8CT6C*, 9CT6C* | 2 | 27 | 28.1 | 6 | 6.3 | + C571A (M) | 1 | 9 | 14.1 | 6 | 9.4 |
| | + A200G/A, 8CT6C*, 9CT6C* | 1 | | | | | | | | | | | + A16080G/A | 1 | | | | |
| | + 7CT6C*, 8CT6C* | 1 | | | | | | | | | | | + A16116G (M) | 1 | | | | |
| | | | | | | | + A234G/A | 1 | | | | | + G16412G/A | 1 | | | | |
| | | | | | | | + C16111T/C | 1 | | | | | | | | | | |
| | Sub total | 115 | | | | | Sub total | 96 | | | | | Sub total | 64 | | | | |
| Total | | 611 | 152 | 24.9 | 46 | 7.5 | | 594 | 151 | 25.4 | 31 | 5.2 | | 355 | 103 | 29.0 | 54 | 15.2 |

Abbreviations: Different, different from bulk cell sequence; Unique, uniquely different heterogeneity; +, mtDNA nucleotide changes in comparison to bulk cell mtDNA sequence; BM, bone marrow; PB, peripheral blood; s, the same as the Cambridge Reference Sequence but different from the bulk sequence.

--.

UNITED STATES PATENT AND TRADEMARK OFFICE

CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Col. 57-58, Lines 35-55, Table 16 should read

--

Table 16. Summary of mtDNA neutral mutations in CD 34$^+$ clones and single granulocytes

| MtDNA genes | Specimens | Assay No (Donor No) | Heterogeneity (neutral mutation) | | | | | | | | |
|---|---|---|---|---|---|---|---|---|---|---|---|
| | | | Total rate (No) | Unique (No) | Substitution (No) | Poly C tract | | | AA change (No) | Interpretation | |
| | | | | | | np 303 - 315 | np 16184-16189 | NC | | P (No) | M (No) |
| Control region | CB CD34$^{+\#}$ | 580 (5) | 1.6% (9) | 1.2% (7) | 0.0% (0) | 0.0% (0) | 0.5% (3) | 0.7% (4) | | | |
| | Adult BM CD34$^{+\#}$ | 611 (6) | 24.9% (152) | 7.5% (46) | 10.5% (64) | 13.8% (66) | 1.1% (7) | 0.0% (0) | | | |
| | Adult PB CD34$^+$ | 594 (6) | 25.4% (151) | 5.2% (31) | 7.9% (47) | 15.3% (91) | 1.5% (9) | 0.0% (0) | | | |
| | Single granulocyte | 355 (6) | 29.0% (103) | 15.2% (54) | 11.8% (42) | 11.8% (42) | 2.0% (12) | 0.0% (0) | | | |
| COI, Cytb | Adult BM CD34$^+$ | 285 (3) | 3.9% (11) | 3.9% (11) | 3.9% (11) | | | | 61.5% (8/13*) | 30.8% (4/13) | 69.2% (9/13) |
| | Adult PB CD34$^+$ | 284 (3) | 6.7% (19) | 5.6% (16) | 6.7% (19) | | | | 43.5% (10/23*) | 56.5% (13/23) | 43.5% (10/23) |
| | Subtotal | 569 (6) | 5.3% (30) | 4.7% (27) | 5.3% (30) | | | | 50.0% (18/36*) | 47.2% (17/36) | 52.8% (19/36) |

Abbreviations: CB, cord blood; np, nucleotide position; AA, amino acid; NC, nucleotide change; P, polymorphism; M, mutation; *, total No of mutational events

--.

UNITED STATES PATENT AND TRADEMARK OFFICE
CERTIFICATE OF CORRECTION

PATENT NO. : 7,255,993 B2
APPLICATION NO. : 10/704283
DATED : August 14, 2007
INVENTOR(S) : Young et al.

It is certified that error appears in the above-identified patent and that said Letters Patent is hereby corrected as shown below:

Col. 59 and 60, Lines 5-67; Col. 61 and 62, Lines 1-15 Table 17 should read

--

Table 17. Mutational spectra of mtDNA CO1 and Cytb genes in individual CD34+ clones from BM and PB

A. BM CD34 clones | B. PB CD34 clones

| Donor | MtDNA sequence | Gene | Amino acid change | Interpretation | Clone No | Heterogeneity Frequency No | % | Unique No | % | MtDNA sequence | Gene | Amino acid change | Interpretation | Clone No | Heterogeneity Frequency No | % | Unique No | % |
|---|---|---|---|---|---|---|---|---|---|---|---|---|---|---|---|---|---|---|
| 1 (47/F) | 'bulk' sequence | | | | 91 | | | | | 'bulk' sequence | | | | 91 | | | | |
| | + T7071C/T | CO1 | Met - Thr | Mutation/ TS | 1 | 3 | 3.2 | 3 | 3.2 | + T6952C | CO1 | Val - Ala | Mutation/ TS | 1 | 4 | 4.2 | 4 | 4.2 |
| | + G7207G/A | CO1 | Gly - Gln | Mutation/ TS | 1 | | | | | + T7312C | CO1 | Phe - Ser | Mutation/ TS | 1 | | | | |
| | + T14924C | Cytb | Ser - Pro | Mutation/ TS | 1 | | | | | + C14832C/G | Cytb | Ala - Gly | Mutation/ TV | 1 | | | | |
| | | | | | | | | | | + A15098A/G | Cytb | Ile - Val | Mutation/ TS | 1 | | | | |
| | Subtotal | | | | 94 | | | | | Subtotal | | | | 95 | | | | |
| 3 (43/M) | 'bulk' sequence | | | | 92 | | | | | 'bulk' sequence | | | | 89 | | | | |
| | + G6955G/A | CO1 | Gly - Asp | Mutation/ TS | 1 | 3 | 3.2 | 3 | 3.2 | + G6955G/A | CO1 | Gly - Asp | Mutation/ TS | 1 | 4 | 4.3 | 4 | 4.3 |
| | + T6987C/T | CO1 | Ser - Pro | Mutation/ TS | 1 | | | | | + T14935C | Cytb | No | Mutation/ TS | 1 | | | | |
| | + T7110T/C | CO1 | Tyr - His | Mutation/ TS | 1 | | | | | + T15067T/C | Cytb | No | Polymorphism/ TS | 1 | | | | |
| | | | | | | | | | | + A15724G/A | Cytb | No | Polymorphism/ TS | 1 | | | | |
| | Subtotal | | | | 95 | | | | | Subtotal | | | | 93 | | | | |
| 5 (54/M) | 'bulk' sequence | | | | 91 | | | | | 'bulk' sequence | | | | 85 | | | | |
| | + T6711G/T | CO1 | Tyr - Asp | Mutation/ TV | 1 | 5 | 5.2 | 5 | 5.2 | + T7022T/C | CO1 | No | Polymorphism/ TS | 4 | 11 | 11.5 | 8 | 8.3 |
| | + G6899A/G | CO1 | No | Mutation/ TS | 1 | | | | | + G7075A/G | CO1 | No | Mutation/ TS | 1 | | | | |
| | + 7022T | CO1 | | | 1 | | | | | + T14864C | Cytb | Cys - Arg | Mutation/ TS | 1 | | | | |
| | + T7297C/T | CO1 | Val - Ala | Mutation/ TS | 1 | | | | | + T15067T/C | Cytb | No | Polymorphism/ TS | 1 | | | | |
| | + 15607A/, | Cytb | | | 1 | | | | | + T15132C | Cytb | Met - Thr | Mutation/ TS | 1 | | | | |
| | G14905G/A, | | No | Polymorphism/ TS | | | | | | + T15818C | Cytb | Tyr - His | Mutation/ TS | 1 | | | | |
| | T15067C | | No | Polymorphism/ TS | | | | | | + C15452C/A, | Cytb | Leu - Ile | Polymorphism/ TS | 1 | | | | |
| | | | | | | | | | | A15607A/G | | No | Polymorphism/ TS | | | | | |
| | | | | | | | | | | + G14905G/A, | Cytb | No | Polymorphism/ TS | 1 | | | | |
| | | | | | | | | | | T15067T/C, | | No | Polymorphism/ TS | | | | | |
| | | | | | | | | | | C15452C/A, | | Leu - Ile | Polymorphism/ TS | | | | | |
| | | | | | | | | | | A15607A/G | | No | Polymorphism/ TS | | | | | |
| | Subtotal | | | | 96 | | | | | Subtotal | | | | 96 | | | | |
| Total | | | | | 285 | 11 | 3.9 | 11 | 3.9 | | | | | 284 | 19 | 6.7 | 16 | 5.6 |
| Heterogeneity of mtDNA CO1 and Cytb genes in total CD34⁻ clones from BM and PB | | | | | | | | | | | | | | 569 | 30 | 5.3 | 27 | 4.7 |

--.

SEQUENCE LISTING

```
<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 1

cgcctacaca attctccgat c                                              21


<210> SEQ ID NO 2
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 2

acttgggtta atcgtgtgac c                                              21


<210> SEQ ID NO 3
<211> LENGTH: 20
<212> TYPE: DNA
<213> ORGANISM: Artificial Sequence
<220> FEATURE:
<223> OTHER INFORMATION: oligonucleotide primer
```

-continued

<400> SEQUENCE: 3
ttaactccac cattagcacc 20

<210> SEQ ID NO 4
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 4
gaaaggctag gaccaaacct a 21

<210> SEQ ID NO 5
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 5
cagtgtattg ctttgaggag g 21

<210> SEQ ID NO 6
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 6
catctggttc ctacttcagg gtc 23

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
ttaactccac cattagcacc 20

<210> SEQ ID NO 8
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 8
gcatggagag ctcccgtgag tgg 23

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
caccctatta accactcacg 20

<210> SEQ ID NO 10
<211> LENGTH: 22

-continued

<212> TYPE: DNA
<213> ORGANISM: Artificial Sequence
<220> FEATURE:
<223> OTHER INFORMATION: oligonucleotide primer

<400> SEQUENCE: 10
tacattactg ccagccacca tg 22

<210> SEQ ID NO 11
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 11
ccacaaaccc cattactaaa cccac 25

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
cggttgttga tgggtgagtc 20

<210> SEQ ID NO 13
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 13
gcatacatca ttattctcgc acgg 24

<210> SEQ ID NO 14
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 14
gggtggtacc caaatctgct tcc 23

<210> SEQ ID NO 15
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 15
gcaacctcaa caccaccttc ttcg 24

<210> SEQ ID NO 16
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 16

-continued gtagacctac ttgcgctgca tgtgc 25

<210> SEQ ID NO 17
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 17
ccattctata ccaacaccta ttctg 25

<210> SEQ ID NO 18
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 18
ccatggggtt ggcttgaaac cagc 24

<210> SEQ ID NO 19
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 19
cagtgtattg ctttgaggag g 21

<210> SEQ ID NO 20
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 20
ctacaaccac gaccaatgat atg 23

<210> SEQ ID NO 21
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 21
gctttgggtg ctaatggtgg ag 22

<210> SEQ ID NO 22
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 22
ctaccaggct tcggaataat ctccc 25

<210> SEQ ID NO 23
<211> LENGTH: 24
<212> TYPE: DNA
<213> ORGANISM: Artificial Sequence -continued

```
<220> FEATURE:
<223> OTHER INFORMATION: oligonucleotide primer

<400> SEQUENCE: 23

gttcttcgaa tgtgtggtag ggtg                                    24
```